US008541579B2

(12) United States Patent
Borthwick et al.

(10) Patent No.: US 8,541,579 B2
(45) Date of Patent: Sep. 24, 2013

(54) SUBSTITUTED DIKETOPIPERAZINES AS OXYTOCIN ANTAGONISTS

(71) Applicant: Glaxo Group Limited, Greenford (GB)

(72) Inventors: Alan David Borthwick, Stevenage (GB); Richard Jonathan Hatley, Stevenage (GB); Deirdre Mary Bernadette Hickey, Stevenage (GB); John Liddle, Stevenage (GB); David George Hubert Livermore, Harlow (GB); Andrew McMurtrie Mason, Stevenage (GB); Neil Derek Miller, Harlow (GB); Fabrizio Nerozzi, Stevenage (GB); Steven Leslie Sollis, Stevenage (GB); Anna Katrin Szardenings, San Diego, CA (US); Paul Graham Wyatt, Cambridge (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/715,522

(22) Filed: Dec. 14, 2012

(65) Prior Publication Data

US 2013/0131338 A1 May 23, 2013

Related U.S. Application Data

(63) Continuation of application No. 12/412,837, filed on Mar. 27, 2009, now Pat. No. 8,367,673, which is a continuation of application No. 10/499,177, filed as application No. PCT/EP02/14823 on Dec. 20, 2002, now Pat. No. 7,514,437.

(30) Foreign Application Priority Data

Dec. 21, 2001 (GB) ................. 0130677.8

(51) Int. Cl.
   *C07D 241/00* (2006.01)
   *C07D 241/02* (2006.01)
(52) U.S. Cl.
   USPC ......................................... 544/336

(58) Field of Classification Search
   USPC ......................................... 544/336
   See application file for complete search history.

(56) References Cited

U.S. PATENT DOCUMENTS

| 4,596,819 A | 6/1986 | Nicolaides et al. |
|---|---|---|
| 5,464,788 A | 11/1995 | Bock et al. |
| 5,817,751 A | 10/1998 | Szardenings et al. |
| 2007/0149524 A1 | 6/2007 | Liddle |
| 2007/0185162 A1 | 8/2007 | Borthwick et al. |
| 2007/0208031 A1 | 9/2007 | Borthwick et al. |
| 2007/0254888 A1 | 11/2007 | Borthwick et al. |

FOREIGN PATENT DOCUMENTS

| GB | 2326639 A | | 12/1998 |
|---|---|---|---|
| WO | WO 99/47549 | * | 3/1999 |
| WO | 9937304 A1 | | 7/1999 |
| WO | 9938844 A1 | | 8/1999 |
| WO | 9947549 A1 | | 9/1999 |
| WO | 2005000311 A1 | | 1/2005 |
| WO | 2006067462 A1 | | 6/2006 |

OTHER PUBLICATIONS

Pettibone et al.; Drug Development Research; 1993; vol. 30; pp. 129-142.
Stella; "Pro Drugs as Novel Drug Delivery Systems"; Pro Drugs: An Overview and Definition (ACS Symposium Series); 1975; pp. 1-115.
Grigorash et al.; Chem. Heterocycl. Compound; 1977; vol. 13; pp. 1280-1282.
Kolasa et al.; J. Org. Chem.; 1990; vol. 55; pp. 1711-1721.
Wyatt et al.; Bioorganic & Med. Chem. Letters; 2001; vol. 11; pp. 1301-1305.
Sarnyai et al.; "Role of Oxytocin in the Neuroadaptation to Drugs of Abuse"; Psychoneuroendocrinology; 1994; vol. 19, No. 1; pp. 85-117.
West; Solid State Chemistry and Its Applications; 1988; p. 358.
Sobocinska et al.; "Analogues of Arginine Vasopressin Modified in Position 2 or 3 with Naphthylalanine: Selective Antagonists of Oxytocin In-Vitro"; J. Pharm. Pharmacol.; 2000; vol. 52, pp. 1105-1112.

* cited by examiner

*Primary Examiner* — Erich A Leeser
(74) *Attorney, Agent, or Firm* — Kathryn L. Coulter

(57) ABSTRACT

A method of treating or preventing diseases or conditions mediated through the action of oxytocin which comprises administering to a human in need thereof of an effective amount of a compound of the formula (I) or a pharmaceutically acceptable salt thereof.

1 Claim, No Drawings

SUBSTITUTED DIKETOPIPERAZINES AS OXYTOCIN ANTAGONISTS

This application is a continuation of U.S. application Ser. No. 12/412,837, filed Mar. 27, 2009, now allowed; which is a continuation of U.S. application Ser. No. 10/499,177, filed Jan. 31, 2005, now U.S. Pat. No. 7,514,437; which is a 371 of International Application No. PCT/EP02/14823 filed Dec. 20, 2002; which claims priority to GB Application No. 0130677.8 filed Dec. 21, 2001.

This invention relates to the use of a class of diketopiperazine derivatives as potent and selective antagonists of oxytocin, to novel compounds within that class and to processes for their preparation.

U.S. Pat. No. 5,817,751 describes combinatorial and solid phase methods for the synthesis of diverse diketopiperazine derivatives and the use of these methods to create libraries of diverse diketopiperazine derivatives.

WO99/47549 describes diketopiperazine derivatives including 3-benzyl-2,5 diketopiperazine derivatives as inhibitors of fructose 1,6-bisphospate (FBPase).

WO99/38844 describes a method for preparing N-[aliphatic or aromatic) carbonyl]-2-aminoacetamide compounds and their cyclisation to give inter alia diketopiperazine derivatives.

WO99/37304 describes oxaheterocyclyl compounds including oxapiperazinyl compounds that are inhibitors of Factor Xa.

The hormone oxytocin is potent contractor of the uterus and is used for the induction or augmentation of labour. Also the density of uterine oxytocin receptors increases significantly by >100 fold during pregnancy and peaks in labour (pre-term and term). Pre-term births/labour (between 24 and 37 weeks) causes about 60% of infant mortality/morbidity and thus a compound which inhibits the uterine actions of oxytocin e.g. oxytocin antagonists, should be useful for the prevention or control of pre-term labour.

We have found a class of diketopiperazine derivatives which exhibit a particularly useful level of activity as selective antagonists at the oxytocin receptor.

The present invention thus a method of treating or preventing diseases or conditions mediated through the action of oxytocin which comprises administering to a mammal in need thereof of an effective amount of a compound of the formula (I)

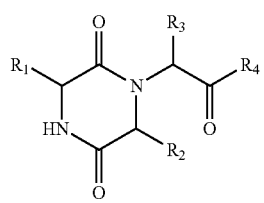

(I)

and/or a physiologically acceptable derivative thereof, wherein:

$R_1$ represents aryl ($C_{1-4}$) alkyl or a 5-7 membered cycloalkyl group optionally substituted with one or more hydroxyl groups which is fused to an optionally substituted benzene ring;

$R_2$ represents $C_{1-6}$alkyl (optionally substituted by a $C_{1-2}$alkoxy, $C_{1-2}$alklthio, di($C_{1-2}$alkyl) amino or a $C_{3-6}$ cycloalkyl group) or $C_{3-6}$cycloalkyl, or 5-6 membered heterocyclic group containing a single hetero atom selected from O, S or N, which nitrogen atom carries a hydrogen atom or a methyl or ethyl group;

$R_3$ represents optionally substituted phenyl, a 5 or 6 membered hetero aryl group or a fused bicyclic ring system containing 9-10 ring members which may be a carbocyclic group or it may contain up to 3 heteroatoms selected from O, S or N and one of the fused rings is benzene;

$R_4$ represents OH or $OC_{1-4}$ alkyl (optionally substituted with $C_{1-4}$alkylcarbonyloxy) or $NR_5R_6$;

$R_5$ represents hydrogen, $C_{1-6}$alkyl (optionally substituted with $C_{1-4}$alkoxy) or $C_{3-7}$cycloalkyl;

$R_6$ represents hydrogen, $C_{1-4}$alkoxy, $C_{3-7}$cycloalkyl, $C_{1-4}$alkyl [optionally substituted with one or more groups selected from, carboxyl, $C_{1-4}$alkylsulphonyl, or $C_{1-4}$alkoxycarbonyl], $C_{2-4}$alkyl [optionally substituted with one or more groups selected from halogen, hydroxy, $C_{1-4}$alkoxy or $NR_7R_8$ wherein $R_7$ and $R_8$ independently represent hydrogen or $C_{1-4}$alkyl or together with the nitrogen atom to which they are attached to form a 3-7 membered saturated heterocyclic ring which may contain an additional heteroatom selected from O, S or N (and which heterocyclic group may be substituted by 1 to 3 groups selected from $C_{1-3}$alkyl, hydroxy, $C_{1-3}$ alkoxy (optionally substituted by $C_{3-6}$ cycloalkyl or optionally substituted phenyl), $C_{3-6}$cycloalkyl or $NR_cR_d$ wherein $R_c$ and $R_d$ each independently represent a group selected from $C_{1-3}$alkyl (optionally substituted by $C_{3-6}$ cycloalkyl or optionally substituted phenyl) or $C_{3-6}$ cycloalkyl)] or $R_6$ represents a phenyl or benzyl group (optionally substituted by one or more methoxy or benzyloxy groups) or an optionally substituted heteroarylmethyl group or a heteroaryl group or $C_{3-7}$ cycloalkyl or the group $CH_2CONR_9R_{10}$ wherein $R_9$ represents hydrogen or $C_{1-4}$alkyl, $R_{10}$ represents hydrogen, $C_{1-4}$alkyl optionally substituted by a 5 or 6 membered heteroaryl group or $R_9$, $R_{10}$ and the nitrogen atom to which they are attached together form a 5 or 6 membered saturated heterocyclic ring and wherein the 6 membered heterocyclic group may contain an additional heteroatom selected from oxygen, sulphur or nitrogen and the additional nitrogen atom either carries a hydrogen atom or a $C_{1-4}$alkyl or $C_{1-4}$alkanoyl group; or $R_5$ and $R_6$ together with the nitrogen atom to which they are attached form a 3 to 7 membered saturated heterocyclic ring which heterocycle may contain an additional heteroatom selected from oxygen, sulphur and nitrogen and wherein the sulphur atom may be in an oxidised form e.g. $SO_2$ and the additional nitrogen atom either carries a hydrogen atom or a $C_{1-4}$alkyl or a $C_{1-4}$alkanoyl group or a $C_{1-4}$alkylsulphonyl group or a $C_{1-3}$ alkoxy$C_{2-4}$ alkyl [and which heterocyclic groups may be substituted by one or more halogen atoms or a group selected from $C_{1-3}$alkyl, hydroxy, oxo, $C_{3-6}$cycloalkyl or $NR_eR_f$ wherein $R_e$ and $R_f$ each independently represent a group selected from $C_{1-3}$alkyl (optionally substituted by $C_{3-6}$ cycloalkyl or optionally substituted phenyl) or $C_{3-6}$ cycloalkyl].

The invention also provides novel compounds of formula (I). A particularly useful class of novel compounds of formula (I) are those wherein $R_1$ is 2-indanyl optionally substituted by hydroxyl and more particularly a 2-indanyl group and $R_2$, $R_3$ and $R_4$ have the meanings defined above and/or physiologically acceptable derivatives thereof. A further useful class of novel compounds of formula (I) are those wherein $R_1$ is a 2-phenethyl and $R_2$, $R_3$ and $R_4$ have the meanings defined above and/or physiologically acceptable derivatives thereof.

The compounds of formula (I) contain at least three centers of asymmetry, namely the carbon atoms carrying the substituents $R_1$, $R_2$ and $R_3$ respectively and it is to be understood that formula (I) includes all possible stereoisomers and mixtures thereof. The substituent $R_3$ may exist in more than one tautomeric form and it is to be all understood that formula (I) includes all possible tautomeric forms and mixtures thereof.

The compounds of formula (I) wherein at least one of the groups $R_1$, $R_2$, $R_3$ or $R_4$ contains a basic or acidic grouping may form salts with physiologically acceptable acids or bases and reference to compounds of formula (I) herein includes such salts.

As used herein, the terms "physiologically acceptable derivative" or "pharmaceutically acceptable derivative", mean any pharmaceutically acceptable salt, solvate, or prodrug e.g. ester or carbamate, or salt or solvate of such a prodrug, of a compound of formula (I), which upon administration to the recipient is capable of providing (directly or indirectly) a compound of formula (I), or an active metabolite or residue thereof. Preferred pharmaceutically acceptable derivatives are salts and solvates.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. Esters may be active in their own right and/or be hydrolysable under in vivo conditions in the human body. Suitable pharmaceutically acceptable in vivo hydrolysable ester groups include those which break down readily in the human body to leave the parent acid or its salt. Examples of such esters include alkyl and 1-(acetyloxy)ethyl esters.

The term alkyl as a group or part of a group refers to a straight or branched alkyl group e.g. methyl, ethyl, propyl, isopropyl, n-butyl, 1-methylpropyl, 2-methylpropyl, t-butyl, pentyl or hexyl.

The term $C_{3-6}$ cycloalkyl as a group or part of a group includes cyclopropyl, cyclobutyl, cyclopentyl and cyclohexyl groups. The term $C_{3-7}$cycloalkyl also includes cycloheptyl.

The term halogen refers to fluorine, chlorine, bromine or iodine.

Unless otherwise specified the term optionally substituted phenyl refers to a phenyl group which may be substituted by 1 to 3 substituents which may be the same or different and selected from halogen, hydroxy, $C_{1-4}$alkyl (optionally substituted by 1-3 halogen atoms or $NR_gR_h$ [wherein $R_g$ is hydrogen or $C_{1-4}$ alkyl, $R_h$ is hydrogen, $C_{1-4}$ alkyl, or $R_g$ and $R_h$ together with the nitrogen atom to which they are attached to form a 5 to 7 membered ring, which ring is saturated and may contain an additional heteroatom selected from nitrogen, oxygen or sulphur]), $C_{1-4}$ alkylsulphonyl, carboxyl, $C_{1-4}$ alkoxycarbonyl, di($C_{1-4}$alkyl)aminocarbonyloxy, $C_{1-4}$alkoxy (optionally substituted by 1-3 halogen atoms, amino, $C_{1-4}$ alkylamino or di-($C_{1-4}$alkyl)amino), phenyl (optionally substituted by halogen or alkylaminosulphonyl), $C_{1-4}$alkoxy, $NR_aR_b$ [wherein $R_a$ is hydrogen or $C_{1-4}$ alkyl, $R_b$ is hydrogen, $C_{1-4}$ alkyl, $C_{1-4}$ alkanoyl or $C_{1-4}$ alkylsulphonyl or $R_a$ and $R_b$ together with the nitrogen atom to which they are attached to form a 5 to 7 membered ring, which ring is saturated and may be substituted by hydroxyl or 1 or 2 $C_{1-4}$alkyl groups or may be spiro-fused to a dioxalane ring or may contain an additional heteroatom selected from nitrogen, oxygen or sulphur and may be substituted by 1 or 2 $C_{1-4}$alkyl groups, or which ring is unsaturated and contains 1-3 additional nitrogen atoms], a 5 or 6 membered heteroaryl group, an optionally N-substituted aminocarbonyl or aminosulphonyl group (wherein the substituents may be 1 or 2 $C_{1-4}$ alkyl groups) or a dihydroxyboryl group).

The term 5 membered heteroaryl refers to a 5 membered ring which contains a heteroatom selected from oxygen, sulphur or nitrogen and which may also contain from 1 to 3 additional nitrogen atoms and which groups may be substituted by 1 or more groups selected from halogen, trifluoromethyl, $C_{1-4}$ alkyl, cycloalkyl, heteroaryl, saturated heterocyclic, or phenyl groups. Examples of such 5 membered heteroaryl groups include furanyl, thienyl, pyrrolyl, oxazolyl, isoxazolyl, thiazolyl, imidazolyl, pyrazolyl, oxadiazolyl, thiadiazolyl, triazolyl or tetrazolyl and these heterocycles may be substituted as described above.

The term 6-membered heteroaryl group refers to a 6-membered unsaturated ring which contains from 1 to 3 nitrogen atoms and which may be substituted by 1 to 3 $C_{1-4}$ alkyl groups, or trifluoromethyl, or alkoxy groups. Examples of such groups include pyridyl, methylpyridyl, trifluoromethylpyridyl, pyrimidinyl and triazinyl.

When $R_3$ is a 5 or 6 membered heteroaryl group this is linked to the rest of the molecule via a carbon atom in the ring.

When $R_3$ is a fused bicyclic carbocyclic ring system this may be for example a naphthyl, tetrahydronaphthyl, indanyl or indenyl group.

When $R_3$ is a fused bicyclic system containing up to 3 heteroatoms which may be the same or different, this is conveniently a 6,5 or 6,6 ring system wherein the heterocycle may be partially saturated or together with the benzene ring to which it is fused to form a heteroaryl group and the heterocycle may be substituted by 1 or 2 groups selected from $C_{1-4}$ alkyl or halogen or haloalkyl and or may contain a carbonyl group. The said $R_3$ group may be linked to the rest of the molecule via a carbon atom in the benzene ring or a carbon atom in the heterocyclic group.

When $R_3$ is a fused 6,6 heteroaryl group the hetero ring contains from 1 to 3 nitrogen atoms and examples of such heteroaryl groups include quinolinyl, isoquinolinyl, phthalazinyl, cinnolinyl, quinazolinyl, quinoxalinyl, 1,2,3 benzotriazinyl or 1,2,4 benzotriazinyl.

When $R_3$ is a 6,5 bicyclic heteroaryl group the 5 membered heterocycle contains a hetero atom selected from O, S or N and may in addition also contain a further 1 or 2 nitrogen atoms and the heterocyclic ring may also be substituted by 1 or 2 $C_{1-4}$ alkyl or halogen or haloalkyl and or may contain a carbonyl group. Examples of such 6,5 bicyclic heteroaryl groups include benzofuranyl, benzothienyl, indolyl, benzo-oxadiazolyl, benzothiadiazolyl, benzo-oxazolyl, benzothiazolyl, benzoisothiazolyl, benzoisoxazolyl, benzimidazolyl, indazolyl or benzotriazolyl and these groups may be substituted as described above.

When $R_3$ is a 6,6 or 6,5 bicyclic heterocyclic group and the heterocycle is partially saturated, this may contain 1 or 2 heteroatoms selected from O, S or N. Examples of such groups include indolinyl, isoindolinyl, dihydrobenzofuranyl, dihydrobenzothienyl, 1,3-benzodioxolyl, benzopyrrolyl, 1,3-benzodithiolyl 1,4-benzodioxanyl, phthalyl, thiophthalyl, chromanyl or chromenyl and the groups may be substituted by one or more halogen or $C_{1-4}$ alkyl groups, haloalkyl, or may contain a carbonyl group.

When $R_3$ is a fused bicyclic heteroaryl linked via the benzene ring therein then suitable examples of such a group include 6-quinolinyl, 4-isoindolinyl, 4-(N-methyl-isoindolinyl, benzimidazolyl, benzothiazolyl, benzofuranyl, benzothienyl, benzimidazolyl benzoxazolyl, 2 methyl-benzo-oxazolyl, benzothiadiazolyl, benzotriazolyl and 1-methyl benzotriazolyl.

When $R_3$ is a fused bicyclic heteroaryl group linked via the heteroaryl ring this may be for example a 2-benzofuranyl, 2-benzothienyl or 2-N-methylindolyl group.

When $R_3$ is a 6,6 or 6,5 heterocyclic group wherein the heterocycle is partially saturated this is conveniently linked via the benzene ring therein and suitable examples include dihydrobenzofuran, dihydrobenzopyrrole, 1,3-benzodioxolyl, 2,2-difluoro-1,3-benzodioxolyl, and 1,4-benzodioxanyl.

When $R_3$ is a substituted phenyl group the said group conveniently carries from 1 to 3 substituents which may be the same or different selected from fluorine, chlorine, bromine $C_{1-3}$ alkyl(methyl), $C_{1-3}$haloalkyl (trifluoromethyl), $C_{1-3}$ alkoxy (methoxy, ethoxy), haloalkoxy (trifluoromethoxy), aminoethoxy e.g. dimethylaminoethoxy, $C_{1-3}$alkoxycarbonyl, carboxy, hydroxy, phenyl or phenyl (substituted by halogen or alkylaminosulphonyl), $NR_aR_b$ [wherein $R_a$ is hydrogen or $C_{1-2}$alkyl and $R_b$ is $C_{1-2}$alkyl, $C_{1-4}$alkanoyl, $C_{1-4}$alkylsulphonyl, $C_{1-3}$alkylaminocarbonyl] or $NR_aR_b$ represents a pyrrolidino or piperidino ring, which ring may be substituted by a $C_{1-2}$alkyl, hydroxyl or a 2,2-1,3-dioxolane group or $NR_aR_b$ represents a morpholino or a piperazino group which groups may be substituted by 1 or 2 $C_{1-2}$alkyl groups or $NR_aR_b$ represents a 5 or 6 membered heteroaryl group containing from 1 to 4 nitrogen atoms (such as a 1-imidazolyl, 1,2-pyrazolyl, 1,2,3-triazolyl or 1,2,4-triazolyl substitutent), $C_{1-3}$alkylsulphonyl, $C_{1-3}$ alkylaminocarbonyl, $C_{1-3}$ alkylaminosulphonyl, dihydroxyboryl or a 5 or 6 membered atom heteroaryl group containing from 1 to 4 nitrogen atoms and which is linked to the phenyl group via a carbon atom in the heteroaryl group (for example pyridyl, pyrazolyl, imidazolyl or tetrazol 5-yl, which heteroaryl groups may be substituted by 1 or more $C_{1-4}$ alkyl groups.

Examples of suitable $R_3$ groups wherein $R_3$ is optionally substituted phenyl include phenyl, halophenyl such as 2-fluorophenyl, 3-fluorophenyl, 4-fluorophenyl, 4-chlorophenyl, 3-chlorophenyl, 2-chlorophenyl, 4-bromophenyl, 2,3-difluorophenyl, 3,4-difluorophenyl, 2,4-difluorophenyl, 3,5-difluorophenyl, 2,5-difluorophenyl, 2-chloro-4-fluorophenyl, 2,4-dichlorophenyl, 3,4-dichlorophenyl, 2 fluoro-4-bromophenyl, 4-chloro-3-fluorophenyl 2,3,4-trifluorophenyl 2,4,5-trifluorophenyl or 2,4,6-trifluorophenyl, 2-fluoro-4,5-dimethoxyphenyl, 3-fluoro-4-methoxyphenyl, 4-fluoro-3-methoxyphenyl, 2-fluoro-4 methoxyphenyl, 2-fluoro-4 hydroxyphenyl, 2-fluoro-4-dimethylaminomethylphenyl, 2-fluoro-4-hydroxymethylphenyl, 3-fluoro-4-(4-morpholino)phenyl, 3-fluoro-4-carboxymethyloxyphenyl, 3-fluoro-4-t-butyloxycarbonylmethyloxyphenyl, 3-fluoro-4-dimethylaminocarbonyloxyphenyl, 3-chloro-4 trifluoromethoxyphenyl, 2,3-difluoro-4-methyl-phenyl, 4-trifluoromethoxyphenyl, 4-trifluoromethylphenyl, 4-hydroxyphenyl, 4-methoxyphenyl, 4-methoxycarbonylphenyl, 3-methoxycarbonyphenyl, 4-methylsulphonylphenyl, 4-methylaminocarbonylphenyl, 4-aminocarbonylphenyl, 4-methylaminosulphonylphenyl, 3-(3-pyrazyolyl) phenyl, 4-(3-pyrazolyl)phenyl, 4-(4-pyrazolyl)phenyl, 4-(3-pyridyl)phenyl, 4-(2-pyridylphenyl), 4-(2-imidazolyl) phenyl, 3-(2-imidazolyl)phenyl, 4-(1-t-butyl-tetrazol-5-yl) phenyl, 4-methylaminophenyl, 4-dimethylaminophenyl, 4-diethylaminophenyl, 4-acetylaminophenyl, 3-acetylaminophenyl, 4-hydroxy-3-acetylaminophenyl, 4-methylsulphonylaminophenyl, 4-N-methylpiperazinophenyl, 4-N-pyrrolidinophenyl, 2-fluoro-4-(4-morpholino)phenyl, 4-(4-morpholino)phenyl, 4-(4-hydroxypiperidino)phenyl, 2-fluoro-4-(4-hydroxypiperidino)phenyl, 3-(1-pyrazolyl) phenyl, 4-(1-pyrazolyl)phenyl, 4-(1-3,5 di-t-butylpyrazolyl) phenyl, 3-(1-imidazolyl)phenyl, 4-(1-imidazolyl)phenyl, 4-(1-1,2,4-triazolyl)phenyl, 4-(1-1,2,3-triazolyl)phenyl, 4-(2-4,-t-butylthiazolyl)phenyl, 4-(5-2-t-butyltetrazolyl) phenyl, 4-(4 spiro-1,3-dioxolanyl)piperidinophenyl, 4-(4-fluorophenyl)phenyl, 4-(4-ethylaminosulphonylphenyl)phenyl, 4-dimethylaminoethoxyphenyl or 3-(dihydroxyboryl) phenyl.

When $R_3$ is a 5 or 6 membered heteroaryl group suitable examples of such groups include 2-furanyl, 3-thienyl, 3-furanyl, 2-thienyl, 4-bromo-2-thienyl, 5-bromo-2-thienyl, 5-chloro-2-thienyl, 3-fluoro-5-methyl-2-thienyl, 5-fluoro-2-thienyl, 5-methyl-2-thienyl, 5-methyl-2-furanyl, 5-bromo-2-furanyl, 4,5-dimethyl-2-furanyl, 2,3-dimethyl-5-thienyl, 5-trifluoromethyl-2-furanyl, 2-furanyl-4-carboxylic acid methylamide, 2-furanyl-5-carboxylic acid methylamide, 2-pyridyl, 6-methyl-2-pyridyl, 6-methyl-3-pyridyl, 6-hydroxy-3-pyridyl, 6-methoxy-3-pyridyl, 6-trifluoromethyl-3-pyridyl, 3-pyridyl, 4-pyridyl, 3,5-pyrimidinyl, 2-thiazolyl, 4-oxazolyl, 4-thiazolyl, 2-methyl-4-oxazolyl, 2-ethyl-4-oxazolyl, 2-cyclopropyl-4-oxazolyl, 2-trifluoromethyl-4-oxazolyl, 2,5-dimethyl-4-oxazolyl, 4-thiazolyl, 2-methyl-4-thiazolyl, 2-trifluoromethyl-4-thiazolyl, 2-trifluoromethyl-5-thiazolyl, 4-isoxazolyl, 1-methyl-4-pyrazolyl, 1,3-dimethyl-5-pyrazolyl, 5-(2-pyridyl)-2-thienyl, 2-(4-morpholino)-5-thiazolyl or 2-(4-methyl-1-piperazino)-5-thiazolyl.

When $R_3$ is an optionally substituted fused bicyclic ring system examples of suitable groups include 2,3-dihydro-1-benzofuran-5-yl, 1,3-benzodioxol-5-yl, 1H-1,2,3-benzotriazol-5-yl, 2,3-dihydro-1,4-benzodioxin-6-yl, 2,2-difluoro-1,3-benzodioxol-5-yl, 1,3-benzothiazol-6-yl, 1-methyl-1H-1,2,3-benzotriazol-5-yl, 1-methyl-1H-1,2,3-benzotriazol-6-yl, 1,2,3-benzothiadiazol-6-yl, 2-methyl-1,3-benzoxazol-5-yl, 2-methyl-1,3-benzoxazol-6-yl, 1-benzofuran-5-yl, 1-methyl-1H-lindol-5-yl, 1-benzothien-5-yl, 1-benzofuran-6-yl, 1H-indol-6-yl, 1-methyl-1H-benzimidazol-6-yl, 1-methyl-1H-benzimidazol-5-yl, 3-methyl-1,2-benzoisoxazol-5-yl, 2-fluoro-1-benzofuran-5-yl, 1H-indol-5-yl, 2-methyl-1H-benzofuran-5-yl, 1H-indazol-5-yl, 1H-indazol-6-yl, 1-benzofuran-2-yl or 1-methyl-1H-benzimidazol-2-yl.

When the group $R_1$ is a 5-7 membered cycloalkyl group which is fused to an optionally substituted benzene ring the optional substituents may be from 1 to 3 groups which may be the same or different and selected from halogen, alkyl, alkoxy, hydroxy, trifluoromethyl, nitro, carboxyl, alkoxycarbonyl or carboxamido.

When the group $R_1$ is aralkyl the aryl moiety is phenyl optionally substituted by 1 to 3 groups which may be the same or different and selected from halogen, alkyl, alkoxy, hydroxy, trifluoromethyl, nitro, carboxyl, alkoxycarbonyl or carboxamido.

Examples of suitable $R_1$ groups include phenethyl or indanyl optionally substituted by hydroxyl e.g. 2-indanyl, 1-hydroxy-2-indanyl, 5-hydroxy-2-indanyl.

Examples of suitable $R_2$ groups include $C_{3-4}$alkyl e.g. isopropyl, 1-methylpropyl or 2-methylpropyl, $C_{3-6}$ cycloalkyl e.g cyclopentyl.

Conveniently $R_4$ is hydroxy, $C_{1-4}$ alkoxy e.g. methoxy, propoxy, t-butoxy, 1-acetyloxyethoxy or $NR_5R_6$.

A preferred class of compounds of formula (I) are those wherein $R_4$ represents hydroxy or the group $NR_5R_6$ or more preferably $NR_5R_6$.

A further preferred class of compounds is represented by formula (1a)

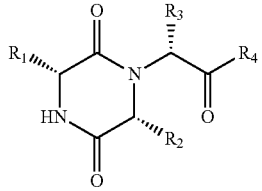

wherein the groups $R_1$, $R_2$, $R_3$ and $R_4$ have the meanings defined for formula (I) Conveniently $R_1$ is a group selected from 2-phenethyl or 2-indanyl optionally substituted by hydroxyl and more particularly 2-indanyl. Conveniently $R_2$ is a group selected from isopropyl, 1-methyl propyl, 2-methylpropyl or cyclopentyl and more preferably $R_2$ is a group selected from 1-methylpropyl, or 2-methylpropyl.

Conveniently $R_3$ is a group selected from phenyl, halophenyl such as 2-fluorophenyl, 3-fluorophenyl, 4-fluorophenyl, 4-chlorophenyl, 3-chlorophenyl, 2-chlorophenyl, 4-bromophenyl, 2,3-difluorophenyl, 3,4-difluorophenyl, 2,4-difluorophenyl, 3,5-difluorophenyl, 2,5-difluorophenyl, 2-chloro-4-fluorophenyl, 2,4-dichlorophenyl, 3,4-dichlorophenyl, 2 fluoro-4-bromophenyl, 4-chloro-3-fluorophenyl 2,3,4-trifluorophenyl 2,4,5-trifluorophenyl or 2,4,6-trifluorophenyl, 2-fluoro-4,5-dimethoxyphenyl, 3-fluoro-4-methoxyphenyl, 4-fluoro-3-methoxyphenyl, 2-fluoro-4 methoxyphenyl, 2-fluoro-4 hydroxyphenyl, 2-fluoro-4-dimethylaminomethylphenyl, 2-fluoro-4-hydroxymethylphenyl, 3-fluoro-4-(4-morpholino)phenyl, 3-fluoro-4-carboxymethyloxyphenyl, 3-fluoro-4-t-butyloxycarbonylmethyloxyphenyl, 3-fluoro-4-dimethylaminocarbonyloxyphenyl, 3-chloro-4 trifluoromethoxyphenyl, 2,3-difluoro-4-methyl-phenyl, 4-trifluoromethoxyphenyl, 4-trifluoromethylphenyl, 4-hydroxyphenyl, 4-methoxyphenyl, 4-methoxycarbonylphenyl, 3-methoxycarbonylphenyl, 4-methylsulphonylphenyl, 4-methylaminocarbonylphenyl, 4-aminocarbonylphenyl, 4-methylaminosulphonylphenyl, 3-(3-pyrazyolyl)phenyl, 4-(3-pyrazolyl)phenyl, 4-(4-pyrazolyl)phenyl, 4-(3-pyridyl)phenyl, 4-(2-pyridylphenyl), 4-(2-imidazolyl)phenyl, 3-(2-imidazolyl)phenyl, 4-(1-t-butyl-tetrazol-5-yl)phenyl, 4-methylaminophenyl, 4-dimethylaminophenyl, 4-diethylaminophenyl, 4-acetylaminophenyl, 3-acetylaminophenyl, 4-hydroxy-3-acetylaminophenyl, 4-methylsulphonylaminophenyl, 4-N-methylpiperazinophenyl, 4-N-pyrrolidinophenyl, 2-fluoro-4-(4-morpholino)phenyl, 4-(4-morpholino)phenyl, 4-(4-hydroxypiperidino)phenyl, 2-fluoro-4-(4-hydroxypiperidino)phenyl, 3-(1-pyrazolyl)phenyl, 4-(1-pyrazolyl)phenyl, 4-(1-3,5 di-t-butylpyrazolyl)phenyl, 3-(1-imidazolyl)phenyl, 4-(1-imidazolyl)phenyl, 4-(1-1,2,4-triazolyl)phenyl, 4-(1-1,2,3-triazolyl)phenyl, 4-(2-4,-t-butylthiazolyl)phenyl, 4-(5-2-t-butyltetrazolyl)phenyl, 4-(4 spiro-1,3-dioxolanyl) piperidinophenyl, 4-(4-fluorophenyl)phenyl, 4-(4-ethylaminosulphonylphenyl)phenyl, 4-dimethylaminoethoxyphenyl, 3-(dihydroxyboryl)phenyl, 2-furanyl, 3-thienyl, 3-furanyl, 2-thienyl, 4-bromo-2-thienyl, 5-bromo-2-thienyl, 5-chloro-2-thienyl, 3-fluoro-5-methyl-2-thienyl, 5-methyl-2-thienyl, 5-methyl-2-furanyl, 5-bromo-2-furanyl, 4,5-dimethyl-2-furanyl, 5-trifluoromethyl-2-furanyl, 2-furanyl-4-carboxylic acid methylamide, 2-furanyl-5-carboxylic acid methylamide, 2-pyridyl, 6-methyl-2-pyridyl, 6-methyl-3-pyridyl, 6-methoxy-3-pyridyl, 6-hydroxy-3-pyridyl, 6-trifluoromethyl-3-pyridyl, 3-pyridyl, 4-pyridyl, 3,5-pyrimidinyl, 2-thiazolyl, 2-methyl-4-oxazolyl, 2-ethyl-4-oxazolyl, 2-cyclopropyl-4-oxazolyl, 2-trifluoromethyl-4-oxazolyl, 2,5-dimethyl-4-oxazolyl, 4-thiazolyl, 2-methyl-4-thiazolyl, 2-trifluoromethyl-4-thiazolyl, 2-trifluoromethyl-5-thiazolyl, 1-methyl-4-pyrazolyl, 1,3-dimethyl-5-pyrazolyl, 5-(2-pyridyl)-2-thienyl, 2,3-dihydro-1-benzofuran-5-yl, 1,3-benzodioxol-5-yl, 1H-1,2,3-benzotriazol-5-yl, 2,3-dihydro-1,4-benzodioxin-6-yl, 2,2-difluoro-1,3-benzodioxin-5-yl, 1,3-benzothiazol-6-yl, 1-methyl-1H-1,2,3-benzotriazol-5-yl, 1-methyl-1H-1,2,3-benzotriazol-6-yl, 1,2,3-benzothiadiazol-6-yl, 2-methyl-1,3-benzoxazol-5-yl, 2-methyl-1,3-benzoxazol-6-yl, 1-benzofuran-5-yl, 1-methyl-1H-lindol-5-yl, 1-benzothien-5-yl, 1-benzofuran-6-yl, 1H-indol-6-yl, 1-methyl-1H-benzimidazol-6-yl, 1-methyl-1H-benzimidazol-5-yl, 3-methyl-1,2-benzoisoxazol-5-yl, 2-fluoro-1-benzofuran-5-yl, 1H-indol-5-yl, 2-methyl-1H-benzofuran-5-yl, 1H-indazol-5-yl, 1H-indazol-6-yl, 1-benzofuran-2-yl or 1-methyl-1H-benzimidazol-2-yl.

Conveniently the group $R_5$ is hydrogen, $C_{1-4}$alkyl e.g. methyl or $C_{1-4}$alkoxy$C_{2-4}$alkyl e.g. 2-methoxyethyl and $R_6$ is a group selected from hydrogen, $C_{1-4}$alkoxy e.g. methoxy, $C_{1-4}$alkyl e.g. methyl, n-propyl, isopropyl or t-butyl, $C_{1-4}$ alkyl substituted by 1 to 3 halogen atoms e.g. 2,2,2-trifluoroethyl or 2-fluoroethyl, $C_{1-4}$alkyl substituted by alkoxycarbonyl or carboxyl e.g. methoxycarbonylmethyl or carboxymethyl, alkyl substituted by alkoxy e.g methoxyethyl, 2,2-dimethoxyethyl, alkyl substituted by hydroxy e.g. hydroxyethyl or alkyl substituted by dialkylamino e.g. dimethylaminoethyl, 2-benzyloxyphenyl, dimethoxybenzyl, optionally substituted heteroarylmethyl e.g. 2-pyridylmethyl, 3-pyridylmethyl, 4-pyridylmethyl, 3-methylimidazolylmethyl, heteroaryl such as thiazolyl e.g. 2-1,3-thiazolyl, alkyl substituted by $NR_7R_8$ [wherein $NR_7R_8$ form a 6-membered heterocyclic ring (e.g. piperidinoethyl or morpholinoethyl)], cycloalkyl e.g. cyclopropyl or cyclohexyl, or $NR_5R_6$ represents, azetidino, 3-hydroxyazetidino, 3-methoxyazetidino, pyrrolidino, piperidino, 4-dimethylaminopiperidino, 4-methyl 1,4-diazepan-1-yl, morpholino, an optionally substituted piperazino ring e.g. N-methylpiperazino, N-methanesulphonylpiperazino, N-2-methoxyethylpiperazino, thiomorpholino or the sulphoxide or sulphone thereof.

A preferred class of compounds of the invention are those of formula (1a) wherein $R_1$ is 2-indanyl, $R_2$ is a group selected from 1-methylpropyl or 2-methylpropyl and $R_4$ is hydroxy and/or more particularly the group $NR_5R_6$.

A further preferred class of compounds of the invention are those of formula (1a) wherein $R_5$ is a group selected from hydrogen, $C_{1-4}$alkyl e.g. methyl or $C_{1-4}$alkoxy$C_{2-4}$alkyl e.g. 2-methoxyethyl and $R_6$ is a group selected from hydrogen, $C_{1-4}$alkoxy e.g. methoxy, $C_{1-4}$alkyl e.g. methyl, n-propyl, isopropyl or t-butyl, $C_{1-4}$ alkyl substituted by 1 to 3 halogen atoms e.g. 2,2,2-trifluoroethyl or 2-fluoroethyl, $C_{1-4}$alkyl substituted by alkoxycarbonyl or carboxyl e.g. methoxycarbonylmethyl or carboxymethyl, alkyl substituted by alkoxy e.g methoxyethyl, 2,2-dimethoxyethyl, alkyl substituted by hydroxy e.g. hydroxyethyl or alkyl substituted by dialkylamino e.g. dimethylaminoethyl, 2-benzyloxyphenyl, dimethoxybenzyl, optionally substituted heteroarylmethyl e.g. 2-pyridylmethyl, 3-pyridylmethyl, 4-pyridylmethyl, 3-methylimidazolylmethyl, heteroaryl such as thiazolyl e.g. 2-1,3-thiazolyl, alkyl substituted by $NR_7R_8$ [wherein $NR_7R_8$ form a 6-membered heterocyclic ring (e.g. piperidinoethyl or morpholinoethyl)], cycloalkyl e.g. cyclopropyl or cyclohexyl, or $NR_5R_6$ represents, azetidino, 3-hydroxyazetidino, 3-methoxyazetidino, pyrrolidino, piperidino, 4-dimethylaminopiperidino, 4-methyl 1,4-diazepan-1-yl, morpholino, an optionally substituted piperazino ring e.g. N-methylpiperazino, N-methanesulphonylpiperazino, N-2-methoxyethylpiperazino, thiomorpholino or the sulphoxide or sulphone thereof.

A yet further preferred class of compounds of the invention are those of formula (1a) wherein $R_3$ is a group selected from phenyl, halophenyl such as 2-fluorophenyl, 3-fluorophenyl, 4-fluorophenyl, 4-chlorophenyl, 3-chlorophenyl, 2-chlorophenyl, 4-bromophenyl, 2,3-difluorophenyl, 3,4-difluorophenyl, 2,4-difluorophenyl, 3,5-difluorophenyl, 2,5-difluorophenyl, 2-chloro-4-fluorophenyl, 2,4-dichlorophenyl, 3,4-dichlorophenyl, 2 fluoro-4-bromophenyl, 4-chloro-3-fluorophenyl 2,3,4-trifluorophenyl 2,4,5-trifluorophenyl or 2,4,6-trifluorophenyl, 2-fluoro-4,5-dimethoxyphenyl, 3-fluoro-4-methoxyphenyl, 4-fluoro-3-methoxyphenyl, 2-fluoro-4 methoxyphenyl, 2-fluoro-4-hydroxyphenyl, 2-fluoro-4-dimethylaminomethylphenyl, 2-fluoro-4-hydroxymethylphenyl, 3-fluoro-4-(4-morpholino)phenyl, 3-fluoro-4-carboxymethyloxyphenyl, 3-fluoro-4-t-butyloxycarbonylmethyloxyphenyl, 3-fluoro-4-dimethylaminocarbonyloxyphenyl, 3-chloro-4 trifluoromethoxyphenyl, 2,3-difluoro-4-methyl-phenyl, 4-trifluoromethoxyphenyl, 4-trifluoromethylphenyl, 4-hydroxyphenyl, 4-methoxyphenyl, 4-methoxycarbonylphenyl, 3-methoxycarbonylphenyl, 4-methylsulphonylphenyl, 4-methylaminocarbonylphenyl, 4-aminocarbonylphenyl, 4-methylaminosulphonylphenyl, 3-(3-pyrazyolyl)phenyl, 4-(3-pyrazolyl)phenyl, 4-(4-pyrazolyl)phenyl, 4-(3-pyridyl)phenyl, 4-(2-pyridylphenyl), 4-(2-imidazolyl)phenyl, 3-(2-imidazolyl)phenyl, 4-(1-t-butyl-tetrazol-5-yl)phenyl, 4-methylaminophenyl, 4-dimethylaminophenyl, 4-diethylaminophenyl, 4-acetylaminophenyl, 3-acetylaminophenyl, 4-hydroxy-3-acetylaminophenyl, 4-methylsulphonylaminophenyl, 4-N-methylpiperazinophenyl, 4-N-pyrrolidinophenyl, 2-fluoro-4-(4-morpholino)phenyl, 4-(4-morpholino)phenyl, 4-(4-hydroxypiperidino)phenyl, 2-fluoro-4-(4-hydroxypiperidino)phenyl, 3-(1-pyrazolyl)phenyl, 4-(1-pyrazolyl)phenyl, 4-(1-3,5 di-t-butylpyrazolyl)phenyl, 3-(1-imidazolyl)phenyl, 4-(1-imidazolyl)phenyl, 4-(1-1,2,4-triazolyl)phenyl, 4-(1-1,2,3-triazolyl)phenyl, 4-(2-4,-t-butylthiazolyl)phenyl, 4-(5-2-t-butyltetrazolyl)phenyl, 4-(4 spiro-1,3-dioxolanyl)piperidinophenyl, 4-(4-fluorophenyl)phenyl, 4-(4-ethylaminosulphonylphenyl)phenyl, 4-dimethylaminoethoxyphenyl, 3-(dihydroxyboryl)phenyl, 2-furanyl, 3-thienyl, 3-furanyl, 2-thienyl, 4-bromo-2-thienyl, 5-bromo-2-thienyl, 5-chloro-2-thienyl, 3-fluoro-5-methyl-2-thienyl, 5-methyl-2-thienyl, 5-methyl-2-furanyl, 5-bromo-2-furanyl, 4,5-dimethyl-2-furanyl, 5-trifluoromethyl-2-furanyl, 2-furanyl-4-carboxylic acid methylamide, 2-furanyl-5-carboxylic acid methylamide, 2-pyridyl, 6-methyl-2-pyridyl, 6-methyl-3-pyridyl, 6-methoxy-3-pyridyl, 6-hydroxy-3-pyridyl, 6-trifluoromethyl-3-pyridyl, 3-pyridyl, 4-pyridyl, 3,5-pyrimidinyl, 2-thiazolyl, 2-methyl-4-oxazolyl, 2-ethyl-4-oxazolyl, 2-cyclopropyl-4-oxazolyl, 2-trifluoromethyl-4-oxazolyl, 2,5-dimethyl-4-oxazolyl, 4-thiazolyl, 2-methyl-4-thiazolyl, 2-trifluoromethyl-4-thiazolyl, 2-trifluoromethyl-5-thiazolyl, 1-methyl-4-pyrazolyl, 1,3-dimethyl-5-pyrazolyl, 5-(2-pyridyl)-2-thienyl, 2,3-dihydro-1-benzofuran-5-yl, 1,3-benzodioxol-5-yl, 1H-1,2,3-benzotriazol-5-yl, 2,3-dihydro-1,4-benzodioxin-6-yl, 2,2-difluoro-1,3-benzodioxol-5-yl, 1,3-benzothiazol-6-yl, 1-methyl-1H-1,2,3-benzotriazol-5-yl, 1-methyl-1H-1,2,3-benzotriazol-6-yl, 1,2,3-benzothiadiazol-6-yl, 2-methyl-1,3-benzoxazol-5-yl, 2-methyl-1,3-benzoxazol-6-yl, 1-benzofuran-5-yl, 1-methyl-1H-indol-5-yl, 1-benzothien-5-yl, 1-benzofuran-6-yl, 1H-indol-6-yl, 1-methyl-1H-benzimidazol-6-yl, 1-methyl-1H-benzimidazol-5-yl, 3-methyl-1,2-benzoisoxazol-5-yl, 2-fluoro-1-benzofuran-5-yl, 1H-indol-5-yl, 2-methyl-1H-benzofuran-5-yl, 1H-indazol-5-yl, 1H-indazol-6-yl, 1-benzofuran-2-yl or 1-methyl-1H-benzimidazol-2-yl.

Particular preferred compounds of the invention include:
(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide
(2R)-2-(4-fluorophenyl)-2-[(3R,6R)-3-(2,3-dihydro-1H-inden-2-yl)-6-isobutyl-2,5-dioxopiperazin-1-yl]-N,N-dimethylethanamide
(2R)-2-(4-fluorophenyl)-2-[(3R,6R)-3-(2,3-dihydro-1H-inden-2-yl)-6-isobutyl-2,5-dioxopiperazin-1-yl]-morpholinamide
(2R)-2-(4-fluorophenyl)-2-[(3R,6R)-3-(2,3-dihydro-1H-inden-2-yl)-6-isobutyl-2,5-dioxopiperazin-1-yl]-N-isopropylethanamide.
(2R)—N-(tert-butyl)-2-[(3R,6R)-3-(2,3-dihydro-1H-inden-2-yl)-6-isobutyl-2,5-dioxopiperazin-1-yl]-2-[4-(4-hydroxypiperidin-1-yl)phenyl]ethanamide.
(2R)-2-{(3R,6R)-3-(2,3-dihydro-1H-inden-2-yl)-6-[(1R)-1-methylpropyl]-2,5-dioxopiperazin-1-yl}-2-(2-fluoro-4-morpholin-4-ylphenyl)-N-isopropylethanamide.
(2R)-2-[(3R,6R)-3-(2,3-dihydro-1H-inden-2-yl)-6-isobutyl-2,5-dioxopiperazin-1-yl]-2-(4-fluorophenyl)-N-(2,2,2-trifluoroethyl)ethanamide.
(2R)-2-(2,4-difluorophenyl)-2-[(3R,6R)-3-(2,3-dihydro-1H-inden-2-yl)-6-isobutyl-2,5-dioxopiperazin-1-yl]-N-isopropylethanamide.
(2R)—N-cyclopropyl-2-(2,4-difluorophenyl)-2-[(3R,6R)-3-(2,3-dihydro-1H-inden-2-yl)-6-isobutyl-2,5-dioxopiperazin-1-yl]ethanamide.
(2R)-2-(2,4-difluorophenyl)-2-[(3R,6R)-3-(2,3-dihydro-1H-inden-2-yl)-6-isobutyl-2,5-dioxopiperazin-1-yl]-N-methylethanamide
(2R)-2-(2,4-difluorophenyl)-2-[(3R,6R)-3-(2,3-dihydro-1H-inden-2-yl)-6-isobutyl-2,5-dioxopiperazin-1-yl]ethanamide
(3R,6R)-1-[(1R)-1-(2,4-difluorophenyl)-2-morpholin-4-yl-2-oxoethyl]-3-(2,3-dihydro-1H-inden-2-yl)-6-isobutylpiperazine-2,5-dione
(3R,6R)-1-[(1R)-1-(2,4-difluorophenyl)-2-(3-hydroxyazetidin-1-yl)-2-oxoethyl]-3-(2,3-dihydro-1H-inden-2-yl)-6-isobutylpiperazine-2,5-dione
(3R,6R)-1-[(1R)-2-azetidin-1-yl-1-(2,4-difluorophenyl)-2-oxoethyl]-3-(2,3-dihydro-1H-inden-2-yl)-6-isobutylpiperazine-2,5-dione
(2R)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyethyl)-N-methylethanamide
(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-[2-(methylsulfonyl)ethyl]ethanamide
(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-(2,2,2-trifluoroethyl)ethanamide
(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-(pyridin-2-ylmethyl)ethanamide
(3R,6R)-1-{(1R)-1-(2,4-difluorophenyl)-2-[4-(methylsulfonyl)piperazin-1-yl]-2-oxoethyl}-3-(2,3-dihydro-1H-inden-2-yl)-6-isobutylpiperazine-2,5-dione
(2R)-2-(2,4-difluorophenyl)-2-[(3R,6R)-3-(2,3-dihydro-1H-inden-2-yl)-6-isobutyl-2,5-dioxopiperazin-1-yl]-N-methoxy-N-methylethanamide
(2R)-(2,4-difluorophenyl)[(3R,6R)-3-(2,3-dihydro-1H-inden-2-yl)-6-isobutyl-2,5-dioxopiperazin-1-yl]ethanoic acid methyl (2R)-(2,4-difluorophenyl)[(3R,6R)-3-(2,3-dihydro-1H-inden-2-yl)-6-isobutyl-2,5 dioxopiperazin-1-yl]ethanoate propyl (2R)-(2,4-difluorophenyl)[(3R,6R)-3-(2,3-dihydro-1H-inden-2-yl)-6-isobutyl-2,5-dioxopiperazin-1-yl]ethanoate 1-(acetyloxy)ethyl (2R)-(2,4-difluorophenyl)[(3R,6R)-3-(2,3-dihydro-1H-inden-2-yl)-6-isobutyl-2,5-dioxopiperazin-1-yl]ethanoate (2R)—N-(tert-butyl)-2-(2,4-difluorophenyl)-2-{(3R,6R)-3-(2,3-dihydro-1H-inden-2-yl)-6-[(1R)-1-methylpropyl]-2,5-dioxopiperazin-1-yl}ethanamide (2R)—N-(tert-butyl)-2-(2,4-difluorophenyl)-2-{(3R,6R)-3-(2,3-dihydro-1H-inden-2-yl)-6-[(1S)-1-methylpropyl]-2,5-dioxopiperazin-1-yl}ethanamide (3R,6R)-1-[(1R)-1-(2,4-difluorophenyl)-2-morpholin-4-yl-2-oxoethyl]-3-(2,3-dihydro-1H-inden-2-yl)-6-[(1S)-1-methylpropyl]piperazine-2,5-dione.

(3R,6R)-1-[(1R)-1-(2,4-difluorophenyl)-2-morpholin-4-yl-2-oxoethyl]-3-(2,3-dihydro-1H-inden-2-yl)-6-[(1R)-1-methylpropyl]piperazine-2,5-dione.

(3R,6R)-1-[(1R)-1-(2,4-difluorophenyl)-2-(3-fluoroazetidin-1-yl)-2-oxoethyl]-3-(2,3-dihydro-1H-inden-2-yl)-6-isobutylpiperazine-2,5-dione.

(2R)-2-[(3R,6R)-3-(2,3-dihydro-1H-inden-2-yl)-6-isobutyl-2,5-dioxopiperazin-1-yl]-N-isopropyl-2-[5-(trifluoromethyl)-2-furyl]ethanamide.

(2S)-2-[(3R,6R)-3-(2,3-dihydro-1H-inden-2-yl)-6-isobutyl-2,5-dioxopiperazin-1-yl]-N-isopropyl-2-(5-methylthien-2-yl)ethanamide.

(2R)-2-[(3R,6R)-3-(2,3-dihydro-1H-inden-2-yl)-6-isobutyl-2,5-dioxopiperazin-1-yl]-N,N-dimethyl-2-[5-(trifluoromethyl)-2-furyl]ethanamide.

(2R)-2-[(3R,6R)-3-(2,3-dihydro-1H-inden-2-yl)-6-isobutyl-2,5-dioxopiperazin-1-yl]-N,N-dimethyl-2-(2-methyl-1,3-oxazol-4-yl)ethanamide.

(3R,6R)-3-(2,3-dihydro-1H-inden-2-yl)-6-isobutyl-1-[(1R)-1-(2-methyl-1,3-oxazol-4-yl)-2-morpholin-4-yl-2-oxoethyl]piperazine-2,5-dione.

(2S)-2-[(3R,6R)-3-(2,3-dihydro-1H-inden-2-yl)-6-isobutyl-2,5-dioxopiperazin-1-yl]-N,N-dimethyl-2-(5-methylthien-2-yl)ethanamide (2S)-2-[(3R,6R)-3-(2,3-dihydro-1H-inden-2-yl)-6-isobutyl-2,5-dioxopiperazin-1-yl]-2-(3-fluoro-5-methylthien-2-yl)-N,N-dimethylethanamide (2R)-2-(1-benzofuran-5-yl)-2-[(3R,6R)-3-(2,3-dihydro-1H-inden-2-yl)-6-isobutyl-2,5-dioxopiperazin-1-yl]-N-isopropylethanamide.

(2R)-2-(1,2,3-benzothiadiazol-6-yl)-N-(tert-butyl)-2-[(3R,6R)-3-(2,3-dihydro-1H-inden-2-yl)-6-isobutyl-2,5-dioxopiperazin-1-yl]ethanamide.

(2R)-2-(2,3-dihydro-1-benzofuran-5-yl)-2-[(3R,6R)-3-(2,3-dihydro-1H-inden-2-yl)-6-isobutyl-2,5-dioxopiperazin-1-yl]-N-isopropylethanamide.

(2R)-2-(1,3-benzodioxol-5-yl)-N-(tert-butyl)-2-[(3R,6R)-3-(2,3-dihydro-1H-inden-2-yl)-6-isobutyl-2,5-dioxopiperazin-1-yl]ethanamide.

(2R)-2-(benzofuran-5-yl)-2-[(3R,6R)-3-(2,3-dihydro-1H-inden-2-yl)-6-isobutyl-2,5-dioxopiperazin-1-yl]-N,N-dimethylethanamide.

(2R)-2-[(3R,6R)-3-(2,3-dihydro-1H-inden-2-yl)-6-isobutyl-2,5-dioxopiperazin-1-yl]-N,N-dimethyl-2-(2-methyl-1-benzofuran-5-yl)ethanamide.

(2R)-2-[(3R,6R)-3-(2,3-dihydro-1H-inden-2-yl)-6-isobutyl-2,5-dioxopiperazin-1-yl]-N-isopropyl-2-(2-methyl-1-benzofuran-5-yl)ethanamide.

(3R,6R)-3-(2,3-dihydro-1H-inden-2-yl)-6-isobutyl-1-[(1R)-1-(2-methyl-1-benzofuran-5-yl)-2-morpholin-4-yl-2-oxoethyl]piperazin-2,5-dione.

(2R)-2-[(3R,6R)-3-(2,3-dihydro-1H-inden-2-yl)-6-isobutyl-2,5-dioxopiperazin-1-yl]-2-(2-fluoro-1-benzofuran-5-yl)-N,N-dimethylethanamide.

(2R)-2-[(3R,6R)-3-(2,3-dihydro-1H-inden-2-yl)-6-isobutyl-2,5-dioxopiperazin-1-yl]-2-(2-fluoro-1-benzofuran-5-yl)-N-isopropylethanamide.

(3R,6R)-3-(2,3-dihydro-1H-inden-2-yl)-1-[(1R)-1-(2-fluoro-1-benzofuran-5-yl)-2-morpholin-4-yl-2-oxoethyl]-6-isobutylpiperazine-2,5-dione.

(2R)-2-[(3R,6R)-3-(2,3-dihydro-1H-inden-2-yl)-6-isobutyl-2,5-dioxopiperazin-1-yl]-2-(1H-indol-6-yl)-N,N-dimethylethanamide.

(2R)-2-(1-benzothien-5-yl)-2-[(3R,6R)-3-(2,3-dihydro-1H-inden-2-yl)-6-isobutyl-2,5-dioxopiperazin-1-yl]-N,N-dimethylethanamide.

The ability of the compounds of formula (I) to inhibit the actions of oxytocin may be determined using a variety of conventional procedures.

Thus, compounds of formula (I) have a high affinity for the oxytocin receptors on the uterus of rats and humans and this may be determined using conventional procedure. For example the affinity for the oxytocin receptors on the rat uterus may be determined by the procedure of Pettibone et al, Drug Development Research 30. 129-142 (1993). The compounds of the invention also exhibit high affinity at the human recombinant oxytocin receptor in CHO cells and this may be conveniently demonstrated using the procedure described by Wyatt et al. Bioorganic & Medicinal Chemistry Letters, 2001 (11) p 1301-1305.

The compounds of the invention are therefore useful in the treatment or prevention of diseases and/or conditions mediated through the action of oxytocin. Examples of such diseases and/or conditions include pre-term labour, dysmenorrhea and endometriosis.

The compounds may also be useful to delay labour prior to elective caesarean section or transfer of the patient to a tertiary care centre. The compounds of the invention may also be useful for improving fertility rates in animals, e.g. farm animals.

The invention therefore provides for the use of a compound of formula (I) and/or physiologically acceptable salts for use in therapy and in particular use as medicine for antagonising the effects of oxytocin upon the oxytocin receptor.

The invention also provides for the use of a compound of formula (I) and/or a physiologically acceptable salt thereof for the manufacture of a medicament for antagonising the effects of oxytocin on the oxytocin receptor.

According to a further aspect, the invention also provides for a method for antagonising the effects of oxytocin upon the oxytocin receptor, comprising administering to a patient in need thereof an antagonistic amount of a compound of formula (I) and/or a physiologically acceptable salt thereof.

It will be appreciated by those skilled in the art that reference herein to treatment extends to prophylactics as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 2 to 50 mg, preferably 5 to 25 mg per day. For oral administration a daily dose will typically be within the range 10 to 800 mg, e.g. 20 to 150 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable salt or non-toxic metabolically labile esters thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The compositions according to the invention may contain between 0.1-99% of the active ingredient, conveniently from 30-95% for tablets and capsules and 3-50% for liquid preparations.

Compounds of formula (I) wherein $R_4$ is the group $NR_5R_6$ may be prepared by cyclisation of the compound of formula (II)

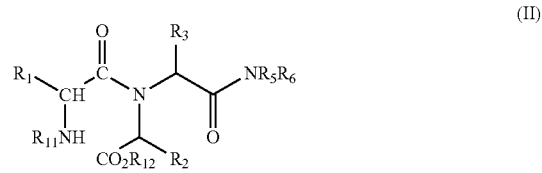

(II)

wherein $R_1$, $R_2$ and $R_3$ have the meanings defined in formula (I) $R_{11}$ is hydrogen and $R_{12}$ is a $C_{1-3}$alkyl group (e.g. methyl) in a suitable solvent such as an alkanol e.g. methanol and/or 2,2,2-trifluoroethanol, dioxan or a mixture thereof or a halohydrocarbon e.g. dichloromethane.

The compound of formula (II) wherein $R_{11}$ is hydrogen is conveniently prepared in-situ by treating a compound of formula (II) wherein $R_{11}$ is an acid labile nitrogen protecting group and $R_{12}$ is hydrogen or $C_{1-3}$alkyl, with an acid in a suitable solvent followed by treatment with a hydrohalic acid and methanol if $R_{12}$ in the starting material is hydrogen, and then addition of a suitable base e.g. triethylamine or by treating a compound of formula (II) wherein $R_{11}$ is an hydrogenolysable nitrogen protecting group and $R_{12}$ is $C_{1-3}$alkyl in a suitable solvent such as methanol or 2,2,2-trifluoroethanol with hydrogen in the presence of a suitable catalyst e.g. palladium on carbon.

Examples of suitable nitrogen protecting groups $R_{11}$ include alkoxycarbonyl e.g. t-butyloxycarbonyl or an optionally substituted benzyloxycarbonyl group.

When $R_{12}$ is $C_{1-3}$alkyl this is conveniently ethyl or more particularly methyl. Examples of suitable acids include mineral acids such as hydrohalic acids e.g. hydrochloric acid or organic acids such as trifluoroacetic acid. The reaction is conveniently carried out in a solvent such as 1,4-dioxan or an alkanol e.g. methanol or a mixture thereof, or halohydrocarbon e.g. dichloromethane.

The compounds of formula (II) may be prepared by reaction of the mixed anhydride (III)

(III)

wherein $R_1$ and $R_{11}$ have the meanings defined above and wherein $R_{13}$ is a $C_{1-6}$ straight or branched chain alkyl, optionally substituted phenyl or benzyl group, with the amine (IV)

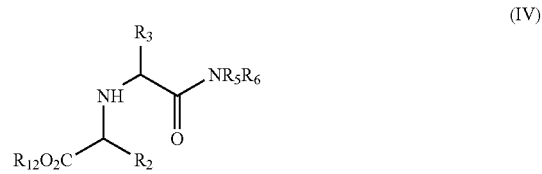

(IV)

wherein $R_2$, $R_3$, $R_5$ and $R_6$ have the meanings defined above, and $R_{12}$ is hydrogen.

The reaction is preferably carried out in an aprotic solvent such as an ether e.g. tetrahydrofuran or a tertiary amide such as N,N-dimethylformamide or a mixture thereof. The compounds of formula (III) may be prepared by treating the N-protected amino acid (V)

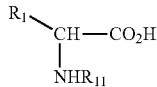
(V)

wherein $R_1$ and $R_{11}$ have the meanings defined above with the corresponding haloformate (VI; $R_{13}CO_2X$ wherein $R_{13}$ has the meaning defined in formula (III) and X is halogen e.g. chlorine, or bromine) in the presence of a suitable tertiary organic amine e.g. N-methylmorpholine and in an aprotic solvent e.g. an ether such as tetrahydrofuran or a hydrocarbon e.g. toluene.

The amine (IV) wherein $R_5$ is hydrogen may be prepared treating the amino acid (VII)

$$R_{12}O_2CCH(R_2)NH_2 \qquad (VII)$$

wherein $R_2$ has the meanings defined above and $R_{12}$ is hydrogen with the aldehyde (VIII; $R_3CHO$ wherein $R_3$ has the meaning defined in formula (I)) in a suitable solvent such as an alkanol e.g. methanol followed by reaction with the isonitrile (IX; $R_6N{=}C$ wherein $R_6$ has the meanings defined in formula I other than hydrogen). Alternatively, the compounds of formula (II) wherein $R_1$, $R_2$ and $R_3$ have the meanings given in formula (I) and $R_{11}$ is a nitrogen protecting group and $R_{13}$ is a carboxyl protecting group may be prepared by reacting the amino acid derivative (VII) wherein $R_2$ has the meaning given in formula (I) and $R_{12}$ is a carboxyl protecting group with the aldehyde (VIII) wherein $R_3$ has the meaning given in formula (I) in a solvent such as an alkanol e.g. methanol or 2,2,2-trifluoroethanol followed by the sequential addition of the amino acid (V) wherein $R_1$ has the meanings given in formula (I) and $R_{11}$ is a carboxyl protecting group and the isonitrile (IX) wherein $R_6$ has the meanings given in formula (I).

Compounds of formula (II) wherein $R_{12}$ is a $C_{1-3}$ alkyl group may also be prepared by reacting the carboxylic acid (X) or an activated derivative thereof

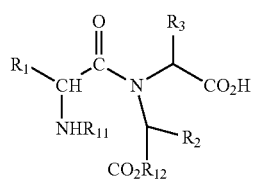
(X)

wherein $R_1$, $R_2$, $R_3$ and $R_{11}$ have the meanings defined above and $R_{12}$ is a $C_{1-3}$ alkyl group, with the amine $NHR_5R_6$ wherein $R_5$ and $R_6$ have the meanings defined in formula (I). Examples of a suitable activated derivative of the carboxylic acid (X) include those commonly used in peptide synthesis e.g. that derived from reaction of benzotriazol-1-yloxytripyrrolidinophosphonium hexafluorophosphate in the presence of a suitable amine such as diisopropylethylamine.

The carboxylic acid (X) may be prepared from the corresponding compound of formula (II) wherein $R_5$ represents hydrogen and $R_6$ represents the 2-hydroxyphenyl by reaction with carbonyldiimidazole or thiocarbonyldiimidazole in a suitable solvent such as dichloromethane and subsequent reaction of the product thus formed with aqueous acetone.

Compounds of formula (II) wherein $R_6$ represents 2-hydroxyphenyl are conveniently prepared by catalytic hydrogenolysis (e.g. $Pd/H_2$) of the corresponding compound wherein $R_6$ is a 2-benzyloxyphenyl group.

In a further aspect of the invention compounds of formula (I) as defined above may be converted into other compounds of formula (I). Thus compounds of formula (I) wherein $R_4$ is hydroxyl maybe prepared from a compound of formula (I) wherein $R_4$ is the group $NR_5R_6$ and $R_5$ is hydrogen $R_6$ is 2-hydroxyphenyl by reaction with carbonyldiimidazole or thiocarbonyldiimidazole in a suitable solvent such as dichloromethane and subsequent reaction of the product thus formed with aqueous acetone.

Compounds of formula (I) wherein $R_5$ is hydrogen and $R_6$ is 2-hydroxphenyl may be from the corresponding compound of formula (I) wherein $R_6$ is a 2-benzyloxyphenyl group by hydrogenolysis using hydrogen and a palladium catalyst.

Compounds of formula (I) wherein $R_4$ is the group $NR_5R_6$ may be prepared by reaction of the compound of formula (I) wherein $R_4$ is hydroxyl or an activated derivative thereof with the amino $NHR_5R_6$ wherein $R_5$ and $R_6$ have the meaning defined in formula (I) under the standard condition for preparing amides from a carboxylic acid and an amine such as $NHR_5R_6$.

Thus the amides may be prepared by treating the compound of formula (I) wherein $R_4$ is hydroxyl with an activating agent such as BOP (benzotriazol-1-yloxy-tris(dimethylamino)phosphonium hexafluorophosphate), TBTU (2-(1H-benzotriazol-1-yl)-1,1,3,3-tetramethyluronium tetrafluoroborate), BOP-Cl (bis(2-oxo-3-oxazolidinyl)phosphinic chloride) or oxalyl chloride in an aprotic solvent such as dichloromethane optionally in the presence of a tertiary amine such as triethylamine and subsequent reaction of the product thus formed with the amine $NHR_5R_6$.

Alternatively compounds of formula (I) wherein $R_4$ is the group $NR_5R_6$ may be prepared by reacting a compound of formula (I) wherein $R_5$ is hydrogen and $R_6$ is 2-hydroxyphenyl with carbonyldiimidazole or thiocarbonyldiimidazole in a suitable solvent such as dichloromethane and subsequent reaction of the product thus formed with the amine $NHR_5R_6$.

Compounds of formula (I) wherein $R_4$ is $OC_{1-4}$ alkyl (optionally substituted with $C_{1-4}$alkylcarbonyloxy) may be prepared by reacting the corresponding carboxylic acid ($R_4$ is OH) or an activated derivative thereof with the appropriate alcohol ($R_4OH$) or alkyl halide ($R_4$halide) under standard conditions for preparing such esters. Suitable activated derivatives include the acid halides, mixed anhydrides, those formed with coupling reagents commonly used in peptide synthesis e.g. carbonyldiimidazole and base salts of the acid e.g. alkali meatal salts.

Compounds of formula (IV) may be converted into other compounds of formula (IV) using standard procedures. Thus compound of formula (IV) wherein $R_5$ is hydrogen and $R_6$ is 2-benzyloxyphenyl may be converted into other compounds of formula (IV) wherein $R_5$ and $R_6$ have other meanings as defined in formula (I) using the same procedures as described above for carrying out analogous reactions on compounds of formula (I).

Compounds of formula (I) wherein the stereochemistry of any of the substituents $R_1$, $R_2$ and $R_3$ is as shown in formula (1a) may be prepared starting from the corresponding single isomers of the intermediates (III), (IV) and (VII) and/or the various isomeric mixtures may be separated by conventional procedures.

The intermediates (V), (VI), (VII), (VIII) and (IX) are either known compounds may be prepared by analogous methods to those known for preparing structurally related compounds.

Compounds of formula group (I) wherein $R_4$ is OH may be prepared by cyclisation of a corresponding compound of formula (II) under the conditions described above for preparing compounds of formula (I).

Physiologically acceptable salts of a compound of formula (I) wherein $R_4$ is OH or one of the groups $R_1$, $R_2$, $R_3$ or $NR_4R_5$ has a basic or acidic centre may be prepared by treating the said base or acid with the required physiologically acceptable acid or base and this reaction is conveniently carried out in a solvent for the said compound of formula (I). Physiologically acceptable derivatives of a compound of formula (I) may be prepared from the appropriate intermediate corresponding to formula (II) using the process described above for preparing compounds of formula (I) or directly from the compounds of formula (I) by conventional procedures for preparing such derivatives. Thus metabolically labile esters may be prepared by esterification of the free carboxyl or hydroxyl group using standard esterification techniques.

The following examples are illustrative, but not limiting of the embodiments of the present invention.

General Purification and Analytical Methods

Analytical HPLC was conducted on a Supelcosil LCABZ+ PLUS column (3.3 cm×4.6 mm ID), eluting with 0.1% $HCO_2H$ and 0.01 M ammonium acetate in water (solvent A), and 0.05% $HCO_2H$ 5% water in acetonitrile (solvent B), using the following elution gradient 0-0.7 minutes 0% B, 0.7-4.2 minutes 0%-100% B, 4.2-5.3 minutes 100% B, 5.3-5.5 minutes 0% B at a flow rate of 3 ml/minute. The mass spectra (MS) were recorded on a Fisons VG Platform spectrometer using electrospray positive [(ES+ve to give $MH^+$ and $M(NH_4)^+$ molecular ions] or electrospray negative [(ES-ve to give $(M-H)^-$ molecular ion] modes on a Micromass series 2 or a Waters ZQ mass spectrometer. $^1H$ NMR spectra were recorded using a Bruker DPX 400 MHz spectrometer using tetramethylsilane as the external standard. Biotage™ chromatography refers to purification carried out using equipment sold by Dyax Corporation (either the Flash 40i or Flash 150i) and cartridges pre-packed with KPSil. Mass directed autoprep refers to methods where the material was purified by high performance liquid chromatography on a HPLCABZ+5 μm column (5 cm×10 mm i d) with 0.1% $HCO_2H$ in water and 95% MeCN, 5% water (0.5% $HCO_2H$) utilising gradient elution at a flow rate of 8 ml minutes$^{-1}$. The Gilson 202-fraction collector was triggered by a VG Platform Mass Spectrometer on detecting the mass of interest.

Hydrophobic frits refer to filtration tubes sold by Whatman. SPE (solid phase extraction) refers to the use of cartridges sold by International Sorbent Technology Ltd. TLC (thin layer chromatography) refers to the use of TLC plates sold by Merck coated with silica gel 60 $F_{254}$. Oasis™ refers to Waters® Oasis™ HLB Extraction Cartridges, sold by Waters Corporation®.

METHOD 1

EXAMPLE 1

(2R)-2-(4-fluorophenyl)-2-[(3R,6R)-3-(2,3-dihydro-1H-inden-2-yl)-6-isobutyl-2,5-dioxopiperazin-1-yl]-N-isopropylethanamide To a solution of (D)-leucine methyl ester hydrochloride (300 mg) in methanol (4 ml) was added triethylamine (230 μl) and 4-fluorobenzaldehyde (177 μl). The mixture was stirred for 2.5 hours before (2R)-[(tert-butoxycarbonyl)amino](2,3-dihydro-1H-inden-2-yl)ethanoic acid (481 mg) and isopropylisocyanide (225 μl) were sequentially added. After stirring for 16 hr, the solvent was removed in vacuo and the residue was dissolved in chloroform. This solution was washed with a saturated aqueous sodium carbonate solution (×2), aqueous citric acid (0.5M, ×2) and brine (×1), dried over magnesium sulphate and evaporated in vacuo. The residue was dissolved in dichloromethane (2 ml) and trifluoroacetic acid (5 ml) and stirred for 3 hours at ambient temperature. After this time, the solvent was removed in vacuo and the residue co-evaporation with toluene (×3) and cyclohexane/ether (1:1, ×2). The residue was treated with a solution of triethylamine in dioxane (2% solution, 10 ml) and was left to stir overnight. After this time, the dioxane was removed in vacuo and the residue was dissolved in ethyl acetate. The solution was washed with citric acid solution (0.5M, ×2), saturated aqueous sodium bicarbonate solution (×1) and brine (×1). The liquors were then dried over magnesium sulphate and in vacuo and were then co-evaporated with cyclohexane:ether (1:1, ×2). This crude material was purified by Biotage™ (90 g, silica) eluting with toluene:ethyl acetate:cyclohexane (5:3:2) with 5% triethylamine to give (2R)-2-(4-fluorophenyl)-2-[(3R,6R)-3-(2,3-dihydro-1H-inden-2-yl)-6-isobutyl-2,5-dioxopiperazin-1-yl]-N-isopropylethanamide (149 mg)

HPLC Rt=3.42 minutes; m/z $[M+H]^+$=480.

$^1H$ NMR (CDCl$_3$) δ 7.44 (m, 2H), 7.22 (m, 2H), 7.16 (m, 2H), 7.11 (t, 2H), 6.50 (d, 1H), 5.60 (d, 1H), 5.11 (s, 1H), 4.10 (m, 1H), 3.96 (m, 2H), 3.16 (dd, 1H), 3.07 (d, 1H), 2.91 (m, 1H), 2.77 (m, 1H), 1.84 (m, 1H), 1.73 (m, 1H), 1.42 (m, 1H), 1.13 (d, 3H), 1.12 (d, 3H), 0.84 (d, 3H), 0.79 (d, 3H)

Similarly prepared

EXAMPLE 2

(2R)—N-(tert-butyl)-2-[(3R,6R)-3-(2,3-dihydro-1H-inden-2-yl)-6-isobutyl-2,5-dioxopiperazin-1-yl]-2-[4-(4-hydroxypiperidin-1-yl)phenyl]ethanamide HPLC Rt=3.27 minutes; m/z $[M+H]^+$=575.

(CDCl$_3$) δ 7.3 (d, 2H), 7.2 (m, 2H), 7.15 (m, 2H), 6.9 (d, 2H), 6.1 (d, 1H), 5.5 (s, 1H), 5.15 (s, 1H), 3.95 (m, 2H), 3.9 (m, 1H), 3.6 (m, 2H), 3.15 (m, 1H), 3.1 (m, 2H), 3.0 (m, 2H), 2.9 (m, 1H), 2.75 (m, 1H), 2.0 (m, 2H), 1.75 (m, 1H), 1.65 (m, 3H), 1.45 (m, 1H), 1.3 (s, 9H), 0.8 (d, 3H), 0.7 (d, 3H).

EXAMPLE 3

(2R)-2-{(3R,6R)-3-(2,3-dihydro-1H-inden-2-yl)-6-[(1R)-1-methylpropyl]-2,5-dioxopiperazin-1-yl}-2-(2-fluoro-4-morpholin-4-ylphenyl)-N-isopropylethanamide HPLC Rt=3.34 minutes; m/z $[M+H]^+$=565

$^1H$ NMR (CDCl$_3$) δ 7.52 (t, 1H), 7.22-7.11 (m, 4H), 7.04 (br s, 1H), 6.66 (dd, 1H), 6.56 (dd, 1H), 5.07 (s, 1H), 4.19-4.08 (m, 2H), 3.98 (dd, 1H), 3.86-3.81 (4H, m), 3.21-2.91 (m, 8H), 2.80-2.73 (m, 1H), 1.96-1.86 (m, 1H), 1.72-1.61 (m, 1H), 1.51-1.40 (m, 1H), 1.19 (d, 3H), 1.16 (d, 3H), 1.06 (d, 3H), 0.92 (t, 3H).

METHOD 2

EXAMPLE 4

(2R)-2-[(3R,6R)-3-(2,3-dihydro-1H-inden-2-yl)-6-isobutyl-2,5-dioxopiperazin-1-yl]-2-(4-fluorophenyl)-N-(2,2,2-trifluoroethyl)ethanamide Methyl (2R)-2-{[(1R,S)-2-{[2-(benzyloxy)phenyl]amino}-1-(4-fluorophenyl)-2-oxoethyl][(2R)-2-[(tert-butoxycarbonyl)amino]-2-(2,3-dihydro-1H-inden-2-yl)ethanoyl]amino}-4-methylpentanoate A mixture of 4-fluorobenzaldehyde (1.2 g), (D)-leucine methyl ester hydrochloride (1.7 g), triethylamine and methanol (56 ml) was stirred at room temperature for 3 hours. 2-Benzyloxyphenylisocynanide (2.0 g) and N-tert-butoxycarbonyl-(D)-indanyl glycine (2.77 g) were then added sequentially. After 40 hours the reaction mixture was partitioned between 2M hydrochloric acid and ethyl acetate. The separated organic layer was washed with a saturated aqueous sodium bicarbonate solution and brine, dried over magnesium sulphate and evaporated in vacuo. The resultant crude material was purified by column chromatography (eluting with 0.5% and 0.2% methanol/dichloromethane) to afford methyl (2R)-2-{[(1R,S)-2-{[2-(benzyloxy)phenyl]amino}-1-1-(4-fluorophenyl)-2-oxoethyl][(2R)-2-[(tert-butoxycarbonyl)amino]-2-(2,3-dihydro-1H-inden-2-yl)ethanoyl]amino}-4-methylpentanoate (4.3 g)

HPLC Rt=4.34 minutes, m/z [M+H]$^+$=752

Methyl N-[(2R)-2-[(tert-butoxycarbonyl)amino]-2-(2,3-dihydro-1H-inden-2-yl)ethanoyl]-N-{(1R,S)-1-(4-fluorophenyl)-2-[(2-hydroxyphenyl)amino]-2-oxoethyl}-D-leucinate A mixture of methyl (2R)-2-{[(1R,S)-2-{[2-(benzyloxy)phenyl]amino}-1-(4-fluorophenyl)-2-oxoethyl][(2R)-2-[(tert-butoxycarbonyl)amino]-2-(2,3-dihydro-1H-inden-2-yl)ethanoyl]amino}-4-methylpentanoate (560 mg), palladium on carbon (70 mg) and ethanol (15 ml) was stirred under an atmosphere of hydrogen for 5 hours. The mixture was filtered through Celite and the filtrate was evaporated in vacuo. The crude product was purified by column chromatography (silica) eluting with ethyl acetate:cyclohexane (10% to 15%) to give methyl N-[(2R)-2-[(tert-butoxycarbonyl)amino]-2-(2,3-dihydro-1H-inden-2-yl)ethanoyl]-N-{(1R,S)-1-(4-fluorophenyl)-2-[(2-hydroxyphenyl)amino]-2-oxoethyl}-D-leucinate.

HPLC Rt=4.06 minutes, m/z [M+H]$^+$=662

(2R)-{[(2R)-2-[(tert-butoxycarbonyl)amino]-2-(2,3-dihydro-1H-inden-2-yl)ethanoyl][(1R)-1-(methoxycarbonyl)-3-methylbutyl]amino}(4-fluorophenyl)ethanoic acid Carbonyldiimidazole (558 mg) was added to a solution of methyl N-[(2R)-2-[(tert-butoxycarbonyl)amino]-2-(2,3-dihydro-1H-inden-2-yl)ethanoyl]-N-{(1R,S)-1-(4-fluorophenyl)-2-[(2-hydroxyphenyl)amino]-2-oxoethyl}-D-leucinate (2.0 g) in dichloromethane (20 ml) and the resultant mixture was stirred at room temperature for 24 hours. The reaction was then concentrated to dryness, dissolved in a mixture of acetone:water (60 ml:40 ml) and stirred for 17 hours at room temperature. The solution was then partitioned between 2M aqueous hydrochloric acid and ethyl acetate. The separated organic layer was washed with saturated aqueous sodium bicarbonate solution and brine before being dried over magnesium sulphate and evaporated in vacuo. Half of the material was taken to be used crude in further experiments. The second half was purified by Biotage™ (silica, 90 g) eluting with methanol:dichloromethane:ammonia (1:98.5:0.5 to 2.5:86.5:1). Evaporation of the appropriate fractions gave (2R)-{[(2R)-2-[(tert-butoxycarbonyl)amino]-2-(2,3-dihydro-1H-inden-2-yl)ethanoyl][(1R)-1-(methoxycarbonyl)-3-methylbutyl]amino}(4-fluorophenyl)ethanoic acid. (173 mg).

HPLC Rt=3.91 minutes, m/z [M+H]$^+$=571

(2R)-2-[(3R,6R)-3-(2,3-dihydro-1H-inden-2-yl)-6-isobutyl-2,5-dioxopiperazin-1-yl]-2-(4-fluorophenyl)-N-(2,2,2-trifluoroethyl)ethanamide A solution of (2R)-{[(2R)-2-[(tert-butoxycarbonyl)amino]-2-(2,3-dihydro-1H-inden-2-yl)ethanoyl][(1R)-1-(methoxycarbonyl)-3-methylbutyl]amino}(4-fluorophenyl)ethanoic acid (73 mg) in N,N-dimethylformamide (2 ml) was sequentially treated with diisopropylethylamine (51 µl), phosphorus$^I$ (1-hydroxy-1H-benzotriazolato-O)tri-1-pyrrolidinyl-(T-4)-hexafluorophosphate (80 mg) and then after 2 minutes, 2,2,2-trifluoroethylamine (25 µl). This reaction mixture was stirred for 2 hours before being partitioned between 2M aqueous hydrochloric acid and ethyl acetate. The organic layer was washed with saturated aqueous sodium bicarbonate solution and brine before being dried over magnesium sulphate and evaporated in vacuo. The residue was dissolved in 4M hydrogen chloride in dioxane and stirred for 7 hours at room temperature. The reagent was removed in vacuo and the residue partitioned between ethyl acetate and saturated aqueous sodium bicarbonate solution. The separated organic fraction was washed with brine before being dried over magnesium sulphate and evaporated in vacuo. The crude material was purified by column chromatography (silica) eluting with methanol:dichloromethane (1% to 3%) to furnish ((2R)-2-[(3R,6R)-3-(2,3-dihydro-1H-inden-2-yl)-6-isobutyl-2,5-dioxopiperazin-1-yl]-2-(4-fluorophenyl)-N-(2,2,2-trifluoroethyl)ethanamide (10 mg)

HPLC Rt=3 4 minutes, m/z [M+H]$^+$=520

$^1$H NMR (CDCl$_3$) δ 7.42 (m, 2H), 7.34 (d, 1H), 7.20-7.10 (m, 6H), 6.61 (t, 1H), 5.28 (s, 1H), 4.08-3.96 (m, 3H), 3.88 (m, 1H), 3.14 (dd, 1H), 3.02 (m, 2H), 2.95-2.77 (m, 2H), 1.88-1.70 (m, 2H), 1.40 (ddd, 1H), 0.85 (d, 3H), 0.79 (d, 3H).

The following compounds were prepared in a similar manner

EXAMPLE 5

(2R)-2-(4-fluorophenyl)-2-[(3R,6R)-3-(2,3-dihydro-1H-inden-2-yl)-6-isobutyl-2,5-dioxopiperazin-1-yl]-N,N-dimethylethanamide HPLC Rt=3.37 minutes, m/z [M+H]$^+$=466

1H NMR (CDCl$_3$); δ 7.47-7.40 (m, 2H), 7.25-7.12 (m, 6H), 6.50 (d, 1H), 6.47 (s, 1H), 4.15 (dd, 1H), 3.98 (dd, 1H), 3.21-3.01 (m, 3H), 2.99 (s, 3H), 2.92-2.73 (m, 2H), 2.83 (m, 3H), 1.59-1.49 (m, 1H), 1.42 (dt, 1H), 0.66-0.57 (m, 1H), 0.62 (d, 3H), 0.40 (d, 3H).

EXAMPLE 6

(2R)-2-(4-fluorophenyl)-2-[(3R,6R)-3-(2,3-dihydro-1H-inden-2-yl)-6-isobutyl-2,5-dioxopiperazin-1-yl]-morpholinamide HPLC Rt=3.32 minutes, m/z [M+H]$^+$=508

1H NMR (CDCl$_3$); δ 7.44-7.39 (m, 2H), 7.26-7.12 (m, 6H), 6.87 (d, 1H), 6.51 (s, 1H), 4.12 (dd, 1H), 4.00 (dd, 1H), 3.73-3.62 (m, 3H), 3.60-3.54 (m, 2H), 3.37 (m, 1H), 3.23 (m, 1H), 3.20-3.02 (m, 4H), 2.91-2.75 (m, 2H), 1.60-1.50 (m, 1H), 1.45 (dt, 1H), 0.63 (d, 3H), 0.62-0.55 (m, 1H), 0.42 (d, 3H).

The 2-fluoro-4-(morpholino)-benzaldehyde used in this synthesis was prepared by the following procedure.

2-Fluoro-4-(morpholino)-benzonitrile

A solution of 2,4-difluorobenzonitrile (6.03 g, 43.35 mmol) and morpholine (8.3 ml, 95.17 mmol) in tetrahydrofuran (27 ml) was stirred at room temperature for 24 hr. The mixture was evaporated and the white solid purified by Biotage™ column (90 g, silica) eluting with cyclohexane:ethyl acetate: (4:1) to give 2-fluoro-4-(morpholino)-benzonitrile as a white solid (5.81 g, 65%).

HPLC Rt=2.83 minutes; m/z [M+H]$^+$=207.

2-Fluoro-4-(morpholino)-benzaldehyde

To a solution of 2-fluoro-4-(morpholino)-benzonitrile (2.82 g, 13.7 mmol) in tetrahydrofuran (27 ml) under a nitrogen atmosphere was added dropwise a 1.5 M solution of DIBAL-H in toluene (18.3 ml, 27.3 mmol) during 13 minutes and the resulting mixture stirred for 23.5 hr at room temperature. The mixture was cooled to −50° C. and the excess DIBAL-H deastoyed by careful addition of methanol (27 ml). The mixture was then stirred at room temperature for 10 mins, saturated ammonium chloride (27 ml) added and the resulting mixture stirred at room temperature for 40 mins., and then evaporated under reduced pressure to a yellow solid. This solid was partitioned between dichloromethane (120 ml) and water (120 ml) and solid potassium carbonate added until the aqueous phase was pH10. The phases were separate via a hyrophobic frit and the organic phase evaporated and the residue purified by a Biotage™ column (40 g, silica) eluting with cyclohexane:ethyl acetate: (7:3) to give 2-fluoro-4-(morpholino)-benzaldehyde (1.96 g, 68%) as a white solid.

HPLC Rt=2.63 minutes; m/z [M+H]$^+$=210.

METHOD 3

EXAMPLE 7

(2R)-2-(2,4-difluorophenyl)-2-[(3R,6R)-3-(2,3-dihydro-1H-inden-2-yl)-6-isobutyl-2,5-dioxopiperazin-1-yl]-N-isopropylethanamide

Methyl N-[(1R)-1-(2,4-difluorophenyl)-2-(isopropylamino)-2-oxoethyl]-L-leucinate To a stirred suspension of (L)-Leucine (1.3 g) in methanol (100 ml) under a nitrogen atmosphere was added 2,4-difluorobenzaldehyde (1.42 g). After stirring at ambient temperature for 3 days, the suspension was cooled to −30° C. and a solution of isopropylisocyanide (0.691 g) in methanol (5 ml) was added. After 3 hours at −30° C. the reaction was allowed to warm to room temperature and was stirred for a further 20 hours. The solvent was removed in vacuo, the residue purified using a Biotage™ column (40 g, silica) eluting with cyclohexane:ethyl acetate (gradient from 8:1 to 1:1). The required fractions were combined and concentrated in vacuo to furnish methyl N-[(1R)-1-(2,4-difluorophenyl)-2-(isopropylamino)-2-oxoethyl]-L-leucinate (1.326 g). $^1$H NMR (CDCl$_3$) d 7.32 (m, 1H), 6.88 (m, 1H), 6.82 (m, 1H), 6.78 (m, 1H), 4.42 (s, 1H), 4.07 (m, 1H), 3.69 (s, 3H), 3.18 (t, 1H), 1.66 (m, 1H), 1.49 (t, 2H), 1.18 (d, 3H), 1.15 (d, 3H), 0.88 (d, 3H), 0.77 (d, 3H)

N-[(1R)-1-(2,4-difluorophenyl)-2-(isopropylamino)-2-oxoethyl]-L-leucine

To a solution of methyl N-[(1R)-1-(2,4-difluorophenyl)-2-(isopropylamino)-2-oxoethyl]-L-leucinate (1.32 g) in methanol (15 ml) was added a solution of lithium hydroxide (294 mg) in water (15 ml). The reaction was rapidly stirred for 1.5 hours and then evaporated in vacuo. The residue was dissolved in water and neutralised using 2N hydrochloric acid. The resulting solid was collected by filtration and dried in vacuo. The filtrate was applied to 4 Oasis cartridges (6 g), which were eluted with water (×2) and methanol (×2). The required fractions were combined and concentrated in vacuo to afford N-[(1R)-1-(2,4-difluorophenyl)-2-(isopropylamino)-2-oxoethyl]-L-leucine (1.01 g).

HPLC Rt=2.51 minutes; m/z [M+H]$^+$=343.

(2R)-2-(2,4-difluorophenyl)-2-[(3R,6R)-3-(2,3-dihydro-1H-inden-2-yl)-6-isobutyl-2,5-dioxopiperazin-1-yl]-N-isopropylethanamide To a solution of (2R)-[(tert-butoxycarbonyl)amino](2,3-dihydro-1H-inden-2-yl)ethanoic acid (291 mg) in dry tetrahydrofuran (5 ml) under a nitrogen atmosphere at −20° C. was added N-methylmorpholine (101 mg) and a solution of isopropylchloroformate in toluene (1.0M, 1 ml). After 10 minutes, a solution of N-[(1R)-1-(2,4-difluorophenyl)-2-(isopropylamino)-2-oxoethyl]-L-leucine (342 mg) in N,N-dimethylformamide/tetrahydrofuran (5 ml/10 ml) was added and the resultant mixture was stirred at room temperature for 4 hours. The solvent was then removed in vacuo and the residue was treated with 4N hydrochloric acid in dioxane (2 ml). After 4 hours, methanol (5 ml) was added to the reaction mixture and this was left to stand for 18 hours. The solvent was then removed in vacuo and the residue was purified on an SPE cartridge (50 g, silica) eluting with cyclohexane/ethyl acetate (gradient from 4:1 to neat ethyl acetate), which furnished the two diastereomers as white solids (2R)-2-(2,4-difluorophenyl)-2-[(3R,6R)-3-(2,3-dihydro-1H-inden-2-yl)-6-isobutyl-2,5-dioxopiperazin-1-yl]-N-isopropylethanamide; (0.137 g)

HPLC Rt=3.47 minutes, m/z [M+H]$^+$=498

$^1$H NMR (CDCl$_3$) δ 7.68 (m, 1H), 7.21 (m, 2H), 7.17 (m, 2H), 6.95 (m, 1H), 6.89 (m, 1H), 6.79 (d, 1H), 5.91 (d, 1H), 5.33 (s, 1H), 4.12 (m, 1H), 4.02 (m, 1H), 3.92 (dd, 1H), 3.16 (m, 1H), 3.05 (m, 2H), 2.90 (m, 1H), 2.78 (m, 1H), 1.85 (m, 1H), 1.79 (m, 1H), 1.49 (m, 1H), 1.17 (m, 6H), 0.88 (d, 3H), 0.82 (d, 3H)

METHOD 4

EXAMPLE 8

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide

Methyl N-[(1R)-2-{[2-(benzyloxy)phenyl]amino}-1-(2,4-difluorophenyl)-2-oxoethyl]-L-leucinate To a suspension of L-leucine (2.33 g) in methanol (200 ml) at −30° C. under nitrogen was added a solution of 2,4-difluorobenzaldehyde (2.52 g) in methanol (10 ml) and a suspension of 2-benzyloxyphenylisonitrile (3.7 g) in methanol (40 ml). The reaction was stirred at −30° C. for 2.5 hours and then allowed to warm to room temperature and stirred for a further 6 days. The solvent was removed in vacuo and the residue was passed through a Biotage™ column (90 g) eluting with cyclohexane:ethyl acetate (8:1 and 7:1) to afford after evaporation of the appropriate fractions methyl N-[(1R)-2-{[2-(benzyloxy)phenyl]amino}-1-(2,4-difluorophenyl)-2-oxoethyl]-L-leucinate (5.06 g).

HPLC Rt=4.0 minutes, m/z [M−H]⁻=495

Methyl N-{(1R)-1-(2,4-difluorophenyl)-2-[(2-hydroxyphenyl)amino]-2-oxoethyl}-L-leucinate A mixture of palladium on carbon (10%, 300 mg), methyl N-[(1R)-2-{[2-(benzyloxy)phenyl]amino}-1-(2,4-difluorophenyl)-2-oxoethyl]-L-leucinate (2.88 g) and ethyl acetate (30 ml) was stirred under a hydrogen atmosphere for 3 hours. The reaction was then filtered through Celite and the filter pad was washed with further portions of ethyl acetate. The combined organic fractions were evaporated to give methyl N-{(1R)-1-(2,4-difluorophenyl)-2-[(2-hydroxyphenyl)amino]-2-oxoethyl}-L-leucinate (2.179 g).

HPLC Rt=3.52 min, m/z [M−H]⁻=405

Methyl N-[1-(2,4-difluorophenyl)-2-(dimethylamino)-2-oxoethyl]-L-leucinate

A solution of methyl N-{(1R)-1-(2,4-difluorophenyl)-2-[(2-hydroxyphenyl)amino]-2-oxoethyl}-L-leucinate (203 mg) and 1,1'-thiocarbonyldiimidazole (100 mg) in dichloromethane (5 ml) was left to stand for 18 hours. Water (10 l) was added to the reaction mixture and this was then stirred rapidly for 30 minutes. After this, 1H-Benzotriazolium, 1-[bis(dimethylamino)methylene]-, tetrafluoroborate (1-), 3-oxide (TBTU, 321 mg) and a solution of dimethylamine in tetrahydrofuran (0.5 ml of 2M solution) were added. The reaction mixture was stirred for a further 18 hours and was then passed down an SPE (5 g, silica) eluting with a gradient (8:1 to 1:2 cyclohexane:ethyl acetate). The required fractions were combined and evaporated to furnish methyl N-[1-(2,4-difluorophenyl)-2-(dimethylamino)-2-oxoethyl]-L-leucinate (100 mg).

HPLC Rt=3.16 minutes m/z [M+H]⁺=343

N-[1-(2,4-difluorophenyl)-2-(dimethylamino)-2-oxoethyl]-L-leucine

To a solution of methyl N-[1-(2,4-difluorophenyl)-2-(dimethylamino)-2-oxoethyl]-L-leucinate (100 mg) in methanol (3 ml) was added a solution of lithium hydroxide (15.4 mg) in water (1 ml). After stirring vigorously for 4 hours the solvent was removed in vacuo. The residue was diluted with water (10 ml) then neutralised with 2N hydrochloric acid. This solution was applied to an Oasis™ cartridge (6 g) and eluted with water (×2) and methanol (×2). The required fractions were combined and evaporated to afford N-[1-(2,4-difluorophenyl)-2-(dimethylamino)-2-oxoethyl]-L-leucine (95 mg).

HPLC Rt=2.23 minutes m/z [M+H]⁺=329

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide To a solution of (2R)-[(tert-butoxycarbonyl)amino](2,3-dihydro-1H-inden-2-yl)ethanoic acid (84 mg) in dry tetrahydrofuran (6 ml) at −20° C. under a nitrogen atmosphere was added N-methylmorpholine (32 l) and a solution of isopropylchloroformate in toluene (1.0M, 290 l). After 10 minutes, a solution of N-[1-(2,4-difluorophenyl)-2-(dimethylamino)-2-oxoethyl]-L-leucine (95 mg) in tetrahydrofuran (10 ml) was added and the reaction was allowed to warm to room temperature. After 20 hours, the solvent was removed in vacuo and the residue was dissolved in 4N hydrochloric acid in dioxan (4 ml). After 4 hours methanol (5 ml) was added and the reaction was left to stand for a further 18 hours. The solvent was then removed in vacuo and the residue was dissolved in dioxan (5 ml) and to this was added triethylamine (0.5 ml). After 1 hour, the solvent was removed and the residue was applied to an SPE (10 g, silica). The product was eluted using methanol. A second SPE was used to further purify the material (2 g, silica) using an ethyl acetate:methanol gradient (20:1 to 1:1) to afford (2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide (38 mg).

HPLC Rt=3.5 minutes, m/z [M+H]⁺=484

¹H NMR (CDCl₃) δ 7.42 (m, 1H), 7.22 (m, 2H), 7.17 (m, 2H), 7.02-6.90 (m, 2H), 6.62 (s, 1H), 6.37 (m, 1H), 4.09 (m, 1H), 3.98 (dd, 1H), 3.20-3.02 (m, 3H), 2.99 (s, 3H), 2.87 (m, 1H), 2.85 (s, 3H), 2.74 (m, 1H), 1.55 (m, 2H), 0.70 (m, 1H), 0.67 (d, 3H), 0.41 (d, 3H)

Similarly prepared

EXAMPLE 9

(2R)—N-cyclopropyl-2-(2,4-difluorophenyl)-2-[(3R,6R)-3-(2,3-dihydro-1H-inden-2-yl)-6-isobutyl-2,5-dioxopiperazin-1-yl]ethanamide HPLC Rt=3.41 minutes, m/z [M+H]⁺=496.

¹H NMR (CDCl₃) δ 7.67 (dt, 1H), 7.59 (1H, d), 7.21-7.11 (m, 4H), 6.99-6.92 (m, 1H), 6.92-6.84 (m, 1H), 6.35 (d, 1H), 5.43 (s, 1H), 3.99 (dd, 1H), 3.93 (dd, 1H), 3.17-2.71 (m, 6H), 1.88-1.70 (m, 2H), 1.48-1.38 (m, 1H), 0.86 (s, 3H), 0.81-0.74 (m, 5H), 0.51-0.45 (m, 2H).

EXAMPLE 10

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide (2RS)-2-(2,4-difluorophenyl)-2-[(3R,6R)-3-(2,3-dihydro-1H-inden-2-yl)-6-isobutyl-2,5-dioxopiperazin-1-yl]-N-(2-benzyloxyphenyl)ethanamide A mixture of 2,4-difluorobenzaldehyde (1.421 g), (D)-leucine methyl ester hydrochloride (1.817 g), triethylamine (1.391 ml) and methanol (20 ml) was stirred at room temperature for 16 hours. N-tert-butoxycarbonyl-(D)-indanylglycine (2.914 g) and 2-benzyloxy-phenylisocyanide (2.090 g) were then added sequentially. After 24 hours the solvent was removed under reduced pressure and the reaction mixture was taken up in dichloromethane (ca. 20 ml) and purified by Biotage™ flash column chromatography (2×90 g silica cartridges on a Biotage Quad 3 system eluted with 1:9 ethyl acetate:cyclohexane) to afford methyl (2R)-2-{[(1R,S)-2-{[2-(benzyloxy)phenyl]amino}-1-(2,4-difluorophenyl)-2-oxoethyl][(2R)-2-[(tert-butoxycarbonyl)amino]-2-(2,3-dihydro-1H-inden-2-yl)ethanoyl]amino}-4-methylpentanoate (5.100 g) (HPLC Rt=4.40 minutes m/z [M+H]⁺=770). This was taken up in 4M hydrogen chloride in 1,4-dioxane (20 ml) and the mixture was left at room temperature for 3 hours. The solvent and hydrogen chloride were blown off using a stream of nitrogen overnight. The crude material was taken up in methanol (90 ml) containing triethylamine (10 ml). After 30 minutes, the methanol and excess of triethylamine were removed under reduced pressure. The crude product was purified by Biotage™ flash column chromatography (2×90 g silica cartridges on a Biotage Quad 3 system eluted with 1:2 ethyl acetate:cyclohexane) to yield (2RS)-2-(2,4-difluorophenyl)-2-[(3R,6R)-3-(2,3-dihydro-1H-inden-2-yl)-6-isobutyl-2,5-dioxopiperazin-1-yl]-N-(2-benzyloxyphenyl)ethanamide (3.381 g).

HPLC Rt=3.99 minutes, m/z [M+H]$^+$=638

(2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (2RS)-2-(2,4-difluorophenyl)-2-[(3R,6R)-3-(2,3-dihydro-1H-inden-2-yl)-6-isobutyl-2,5-dioxopiperazin-1-yl]-N-(2-benzyloxyphenyl)ethanamide (3.381 g) was dissolved in ethyl acetate (200 ml) and hydrogenated at atmospheric pressure over 10% palladium on carbon catalyst (0.980 g of 10% Pd/C:water 1:1 w/w) at room temperature for five hours. The reaction mixture was filtered through Celite and the solvent was removed under reduced pressure to give the (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide as a cream-coloured foam (2.650 g).

HPLC Rt=3.61 minutes, m/z [M−H$^+$]$^-$=546 (no [M+H]$^+$ visible)

(2RS)-2-(2,4-difluorophenyl)-2-[(3R,6R)-3-(2,3-dihydro-1H-inden-2-yl)-6-isobutyl-2,5-dioxopiperazin-1-yl]-ethanoic acid (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (2.650 g) was stirred in dichloromethane (20 ml) and carbonyldiimidazole (1.178 g) was added. the mixture was left at room temperature for 16 hours then the solvent was removed under reduced pressure. The residue was then taken up in 1:1 acetone:water (v/v) (80 ml) and left at room temperature for 30 minutes. The bulk of the acetone was then removed under reduced pressure and the residue was partitioned between dichloromethane and 0.5M hydrochloric acid. The organic phase was separated (hydrophobic frit) and evaporated under reduced pressure. The crude product was purified (Biotage™ flash chromatography column, 90 g silica cartridge eluted with (i) 1:1 ethyl acetate:cyclohexane (ii) ethyl acetate (iii) ethyl acetate:methanol 9:1) to afford (2RS)-2-(2,4-difluorophenyl)-2-[(3R,6R)-3-(2,3-dihydro-1H-inden-2-yl)-6-isobutyl-2,5-dioxopiperazin-1-yl]-ethanoic acid as a colourless solid 1.524 g as a mixture of epimers.

HPLC Rt=3.44 and 3.58 minutes, both m/z [M+H$^+$]=457

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide The acid (2RS)-2-(2,4-difluorophenyl)-2-[(3R,6R)-3-(2,3-dihydro-1H-inden-2-yl)-6-isobutyl-2,5-dioxopiperazin-1-yl]-ethanoic acid (0.747 g) prepared as described above was dried over P$_4$O$_{10}$ in vacuo for five hours to give 0.724 g drier material; this was dissolved in anhydrous dichloromethane:acetonitrile (1:1 v/v, 6 ml) and treated with triethylamine (0.223 ml) and BOP—Cl (bis(2-oxo-3-oxazolidinyl)phosphinic chloride, dissolved in anhydrous dichloromethane:acetonitrile (1:1 v/v, 6 ml) and treated with triethylamine (0.223 ml) and BOP—Cl (bis(2-oxo-3-oxazolidinyl)phosphinic chloride, 0.450 g) and the mixture was sonicated for ca. 1 min to give a gelatinous mass. After 10 minutes at room temperature a solution of dimethylamine in tetrahydrofuran (10 ml of 2M solution) was added to give a clear solution; this was left for 16 hours at room temperature. The solvents were removed under reduced pressure and the mixture was partitioned between dichloromethane and 0.1M hydrochloric acid. The organic phase was separated (hydrophobic frit) and evaporated under reduced pressure. The crude product was purified by flash column chromatography (12 g Biotage™ silica cartridge eluted with (i) 1:1 ethyl acetate:cyclohexane (ii) ethyl acetate (iii) ethyl acetate:methanol 9:1) to give the (2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide as a colourless solid 0.285 g.

HPLC Rt=3.43 minutes, m/z [M+H]$^+$=484

$^1$H NMR (CDCl$_3$) δ 7.47-7.40 (m, 1H), 7.24-7.11 (m, 4H), 7.01-6.91 (m, 3H), 6.62 (s, 1H), 4.09 (dd, 1H), 3.98 (dd, 1H), 3.19-3.01 (m, 3H), 2.99 (3, 3H), 2.92-2.75 (m, 5H), 1.64-1.51 (m, 2H), 0.76-0.66 (m, 4H), 0.43 (d, 3H).

METHOD 5

EXAMPLE 11

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide

(2R)-[(benzyloxycarbonyl)amino](2,3-dihydro-1H-inden-2-yl)ethanoic acid

R-Indanylglycine (1.91 g) was suspended in dioxane (10 ml) and water (10 ml). To this was added triethylamine (1.7 ml) and N-(benzyloxycarbonyloxy)succinimide (2.54 g) and the reaction mixture was stirred rapidly at room temperature for 2 days. The reaction mixture was poured into water (50 ml) and extracted with chloroform (100 ml). The organic phase was washed with 1N hydrochloric acid (50 ml) and water (50 ml). This was dried over magnesium sulphate and the solvent removed in vacuo to give (2R)-[(benzyloxycarbonyl)amino](2,3-dihydro-1H-inden-2-yl)ethanoic acid (3.06 g).

HPLC Rt=3.35 minutes; m/z [M+H]$^+$=326.

$^1$H NMR (CDCl$_3$) δ 7.40-7.29 (m, 5H), 7.21-7.11 (m, 4H), 5.28 (d, 1H), 5.11 (s, 2H), 4.57 (m, 1H), 3.14-2.79 (m, 5H).

(2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide To a solution of (D)-leucine methyl ester hydrochloride (1.45 g) in methanol (10 ml) was added triethylamine (1.12 ml) and 2,4-difluorobenzaldehyde (0.875 ml). The mixture was stirred for 3 days before (2R)-[(benzyloxycarbonyl)amino](2,3-dihydro-1H-inden-2-yl)ethanoic acid (2.6 g) and 2-benzyloxyphenylisocyanide (1.76 g) were sequentially added. The reaction mixture was left to stand for 24 hours. The solvent was removed in vacuo and the residue was separated between ethyl acetate (200 ml) and water (200 ml). The organic phase was washed with brine. To this solution was added palladium on carbon (2.0 g) and acetic acid (10 ml) and the reaction mixture was stirred under an atmosphere of hydrogen for 2 hours. The mixture was filtered through Celite and washed with water (3×100 ml), saturated sodium bicarbonate solution, brine and dried over magnesium sulphate.

The solvent was evaporated in vacuo. The crude product was purified by column chromatography (silica) eluting with ethyl acetate:cyclohexane (50% to 66%) to give (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (2.0 g).

HPLC Rt=3.59 minutes; m/z [M+H]$^+$=548.

(2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide Carbonyldiimidazole (4.80 g, 1.54 equiv.) was suspended in anhydrous dichloromethane (40 mL) and the suspension was left at room temperature for 15 minutes. (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (10.50 g, pre-dried in vacuo over $P_4O_{10}$ for 24 hours) was then added with stirring and the resultant solution was stirred at room temperature for 6 hours. The resulting yellow solution was then treated with a 2.0M solution of dimethylamine in tetrahydrofuran (54 mL, 5.6 equiv.) and the resulting mixture was stirred at room temperature for 16 hours. The solvents plus residual dimethylamine were removed under reduced pressure and the reaction mixture was taken up in dichloromethane (200 mL) and washed with 1M hydrochloric acid (200 mL). The organic phase was separated using a hydrophobic frit and was evaporated under reduced pressure to ca. 50 mL. The crude product was applied to 4×90 g silica Biotage™ columns on a Quad 3 system; each column being eluted with (i) 2:1 v/v ethyl acetate:cyclohexane (12× 50 mL fractions), (ii) ethyl acetate (12×50 mL fractions), (iii) 9:1 v/v ethyl acetate:methanol to give (2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide (5.753 g, 62%) as a colourless solid.

HPLC Rt=3.41 minutes, m/z [M+H]$^+$=484
$^1$H NMR (CDCl$_3$) δ 7.48-7.38 (m, 2H), 7.24-7.11 (m, 4H), 7.01-6.90 (m, 2H), 6.62 (s, 1H), 4.09 (dd, 1H), 3.98 (dd, 1H), 3.19-3.01 (m, 3H), 2.99 (3, 3H), 2.92-2.75 (m, 5H), 1.64-1.51 (m, 2H), 0.76-0.66 (m, 4H), 0.43 (d, 3H).

Similarly prepared:

EXAMPLE 12

(2R)-2-(2,4-difluorophenyl)-2-[(3R,6R)-3-(2,3-dihydro-1H-inden-2-yl)-6-isobutyl-2,5-dioxopiperazin-1-yl]-N-methylethanamide colourless solid, 41%

HPLC Rt=3.4 minutes, m/z [M+H]$^+$=470

EXAMPLE 13

(2R)-2-(2,4-difluorophenyl)-2-[(3R,6R)-3-(2,3-dihydro-1H-inden-2-yl)-6-isobutyl-2,5-dioxopiperazin-1-yl]ethanamide colourless solid, 36%

HPLC Rt=3.3 minutes, m/z [M+H]$^+$=456

EXAMPLE 14

(3R,6R)-1-[(1R)-1-(2,4-difluorophenyl)-2-morpholin-4-yl-2-oxoethyl]-3-(2,3-dihydro-1H-inden-2-yl)-6-isobutylpiperazine-2,5-dione colourless solid, 61%

HPLC Rt=3.4 minutes, m/z [M+H]$^+$=526

EXAMPLE 15

(3R,6R)-1-[(1R)-1-(2,4-difluorophenyl)-2-(3-hydroxyazetidin-1-yl)-2-oxoethyl]-3-(2,3-dihydro-1H-inden-2-yl)-6-isobutylpiperazine-2,5-dione colourless solid, 45%

HPLC Rt=3.2 minutes, m/z [M+H]$^+$=512
(azetidin-3-ol prepared by the method of S S Chatterjee and D J Triggle; J Chem. Soc. Chem. Comm. (2) 93 (1968)

EXAMPLE 16

(3R,6R)-1-[(1R)-2-azetidin-1-yl-1-(2,4-difluorophenyl)-2-oxoethyl]-3-(2,3-dihydro-1H-inden-2-yl)-6-isobutylpiperazine-2,5-dione colourless solid, 46%

HPLC Rt=3.4 minutes, m/z [M+H]$^+$=496

EXAMPLE 17

(2R)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyethyl)-N-methylethanamide colourless solid, 59%

HPLC Rt=3.3 minutes, m/z [M+H]$^+$=514

EXAMPLE 18

(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-[2-(methylsulfonyl)ethyl]ethanamide colourless solid, 22%

HPLC Rt=3.2 minutes, m/z [M+H]$^+$=576

EXAMPLE 19

(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-(2,2,2-trifluoroethyl)ethanamide colourless solid, 11%

HPLC Rt=3.5 minutes, m/z [M+H]$^+$=552
(2,2,2-trifluoroethylmethylamine hydrochloride was prepared by the method of E R Bissell and M Finger; J. Org. Chem. 24 1256-1259 (1959))

EXAMPLE 20

(2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-(pyridin-2-ylmethyl)ethanamide tan foam, 19%

HPLC Rt=3.5 minutes, m/z [M+H]$^+$=561

EXAMPLE 21

(2R)-2-(2,4-difluorophenyl)-2-[(3R,6R)-3-(2,3-dihydro-1H-inden-2-yl)-6-isobutyl-2,5-dioxopiperazin-1-yl]-N-methoxy-N-methylethanamide HPLC Rt=3.4 minutes, m/z [M+H]$^+$=500

EXAMPLE 22

(2R)-(2,4-difluorophenyl)[(3R,6R)-3-(2,3-dihydro-1H-inden-2-yl)-6-isobutyl-2,5-dioxopiperazin-1-yl]ethanoic acid Carbonyldiimidazole (1.42 g, 1.6 equiv.) was suspended in anhydrous dichloromethane (10 mL) and the suspension was left at room temperature for 15 minutes. (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (3.00 g) was then added and the resultant solution was stirred at room temperature for 16 hours. The resulting yellow solution was then evaporated under reduced pressure and the residue was treated with a 1:1 (v/v) mixture of water and acetone (10 mL). The mixture was stirred for 2 hours, then the acetone was removed under reduced pressure and the residue was partitioned between dichloromethane and 0.1M HCl aq. The organic phase was separated using a hydrophobic frit then evaporated to low volume and purified by chromatography on a Biotage Quad 3 system (90 g silica column) eluted with 1:1 (v/v) ethyl acetate:cyclohexane, then ethyl acetate, then 1:1 (v/v) ethyl acetate:methanol to give a mixture of diastereomers (2.61 g). These were separated on a chiral reverse-phase column (Chiralcel OD, eluted with 15% propan-2-ol/heptane containing 0.1% TFA) to give: (2R)-(2,4-difluorophenyl)[(3R,6R)-3-(2,3-dihydro-1H-inden-2-yl)-6-isobutyl-2,5-dioxopiperazin-1-yl]ethanoic acid (1.60 g)

HPLC Rt=3.4 minutes, m/z [M+H]$^+$=457

EXAMPLE 23 methyl (2R)-(2,4-difluorophenyl)[(3R,6R)-3-(2,3-dihydro-1H-inden-2-yl)-6-isobutyl-2,5-dioxopiperazin-1-yl]ethanoate Carbonyldiimidazole (0.324 g, 1.6 equiv.) was suspended in anhydrous dichloromethane (4 mL) and the suspension was left at room temperature for 15 minutes. (2RS)-2-(2,4-difluorophenyl)-2-[(3R,6R)-3-(2,3-dihydro-1H-inden-2-yl)-6-isobutyl-2,5-dioxopiperazin-1-yl]-N-(2-hydroxyphenyl)ethanamide (0.800 g) was then added with stirring and the resultant solution was left at room temperature for 16 hours. The mixture was then treated with methanol (10 mL) and left at room temperature overnight. The solvents were removed under reduced pressure and the residue was purified by preparative plate chromatography on silica (20×20 cm plates×4 eluted with 1:3 ethyl acetate:cyclohexane×5) to give: methyl (2R)-(2,4-difluorophenyl)[(3R,6R)-3-(2,3-dihydro-1H-inden-2-yl)-6-isobutyl-2,5-dioxopiperazin-1-yl]ethanoate (0.453 g, 66%)

HPLC Rt=3.42 minutes, m/z [M+H]$^+$=471
Similarly prepared:

EXAMPLE 24 propyl (2R)-(2,4-difluorophenyl)[(3R,6R)-3-(2,3-dihydro-1H-inden-2-yl)-6-isobutyl-2,5-dioxopiperazin-1-yl]ethanoate HPLC Rt=3.71 minutes, m/z [M+H]$^+$=499

EXAMPLE 25

1-(acetyloxy)ethyl (2R)-(2,4-difluorophenyl)[(3R,6R)-3-(2,3-dihydro-1H-inden-2-yl)-6-isobutyl-2,5-dioxopiperazin-1-yl]ethanoate (2R)-(2,4-difluorophenyl)[(3R,6R)-3-(2,3-dihydro-1H-inden-2-yl)-6-isobutyl-2,5-dioxopiperazin-1-yl]ethanoic acid (example 22) (0.130 g) was stirred in anhydrous DMF (1 mL) and anhydrous potassium carbonate (0.020 g, 0.5 eq.) was added. The mixture was stirred at room temperature for 1 hour then cooled to −10° C. (ice-salt bath). The heterogeneous mixture was treated with 1-bromoethyl acetate (0.120 mL, excess) and stirred for 3.5 hours keeping the bath temperature between −10 and −5° C. It was then partitioned between DCM and 1M HCl aq. (20 mL each). The organic phase was separated (hydrophobic frit) and evaporated under reduced pressure to give a purple gum; this was purified by SPE cartridge (5 g, silica eluted with (i) cyclohexane×2, (ii) DCM×2, (iii) diethyl ether×2, (iv) ethyl acetate×2, (v) methanol×2 to give 1-(acetyloxy)ethyl (2R)-(2,4-difluorophenyl)[(3R,6R)-3-(2,3-dihydro-1H-inden-2-yl)-6-isobutyl-2,5-dioxopiperazin-1-yl]ethanoate (0.081 g) as a yellow foam.

HPLC Rt=3.5 minutes, m/z [M+H]$^+$=543
Similarly prepared:

In the table below, Examples 26, 54-55, 66-104, 107-117, 124-131 were prepared via method 1. The t-butyl ester Example 39 was prepared via perchloric acid-catalysed transesterification of the corresponding acid (Example 22) with t-butyl acetate by the procedure of T Kolasa and M J Miller; Journal of Organic Chemistry (1990), 55(6), 1711-21. Other Examples in the table below were prepared via method 5.

| Eg No. | Regno | Mwt | Rt/min | +ve ion | −ve ion | name |
|---|---|---|---|---|---|---|
| 26 | F | 511.6 | 3.6 | 512 | 510 | (2R)-N-(tert-butyl)-2-(2,4-difluorophenyl)-2-[(3R,6R)-3-(2,3-dihydro-1H-inden-2-yl)-6-isobutyl-2,5-dioxopiperazin-1-yl]ethanamide |

-continued

| Eg No. | Regno | Mwt | Rt/ min | +ve ion | −ve ion | name |
|---|---|---|---|---|---|---|
| 27 | | 537.5 | 3.4 | 538 | 536 | (2R)-2-(2,4-difluorophenyl)-2-[(3R,6R)-3-(2,3-dihydro-1H-inden-2-yl)-6-isobutyl-2,5-dioxopiperazin-1-yl]-N-(2,2,2-trifluoroethyl)ethanamide |
| 28 | | 543.6 | 3.2 | 544 | 542 | (2R)-2-(2,4-difluorophenyl)-2-[(3R,6R)-3-(2,3-dihydro-1H-inden-2-yl)-6-isobutyl-2,5-dioxopiperazin-1-yl]-N-(2,2-dimethoxyethyl)ethanamide |
| 29 | | 513.6 | 3.3 | 513 | 511 | (2R)-2-(2,4-difluorophenyl)-2-[(3R,6R)-3-(2,3-dihydro-1H-inden-2-yl)-6-isobutyl-2,5-dioxopiperazin-1-yl]-N-(2-methoxyethyl)ethanamide |
| 30 | | 527.6 | 3.4 | 528 | none | (2R)-2-(2,4-difluorophenyl)-2-[(3R,6R)-3-(2,3-dihydro-1H-inden-2-yl)-6-isobutyl-2,5-dioxopiperazin-1-yl]-N-(2-methoxyethyl)-N-methylethanamide |

-continued

| Eg No. | Regno | Mwt | Rt/ min | +ve ion | −ve ion | name |
|---|---|---|---|---|---|---|
| 31 | | 571.7 | 3.3 | 572 | none | (2R)-2-(2,4-difluorophenyl)-2-[(3R,6R)-3-(2,3-dihydro-1H-inden-2-yl)-6-isobutyl-2,5-dioxopiperazin-1-yl]-N,N-bis(2-methoxyethyl)ethanamide |
| 32 | | 528.6 | 2.7 | 529 | none | (2R)-2-(2,4-difluorophenyl)-N-[2-(dimethylamino)ethyl]-2-[(2R,5R)-2-isobutyl-3,6-dioxo-5-(2-phenylethyl)piperazin-1-yl]-N-methylethananmide |
| 33 | | 654.7 | 2.7 | 541 | 539 | (2R)-2-(2,4-difluorophenyl)-2-[(3R,6R)-3-(2,3-dihydro-1H-inden-2-yl)-6-isobutyl-2,5-dioxopiperazin-1-yl]-N-[2-(dimethylamino)ethyl]-N-methylethanamide trifluoroacetate |
| 34 | | 511.6 | 3.6 | 512 | none | (2R)-2-(2,4-difluorophenyl)-2-[(3R,6R)-3-(2,3-dihydro-1H-inden-2-yl)-6-isobutyl-2,5-dioxopiperazin-1-yl]-N-isopropyl-N-methylanamide |

| Eg No. | Regno | Mwt | Rt/min | +ve ion | −ve ion | name |
|---|---|---|---|---|---|---|
| 35 | | 471.6 | 3.2 | 472 | 470 | (2R)-2-(2,4-difluorophenyl)-2-[(2R,5R)-2-isobutyl-3,6-dioxo-5-(2-phenylethyl)piperazin-1-yl]-N,N-dimethylethanamide |
| 36 | | 497.6 | 3.5 | 498 | none | (2R)-2-(2,4-difluorophenyl)-2-[(3R,6R)-3-(2,3-dihydro-1H-inden-2-yl)-6-isobutyl-4-methyl-2,5-dioxopiperazin-1-yl]-N,N-dimethylethanamide |
| 37 | | 554.7 | 2.7 | 555 | none | (2R)-2-(2,4-difluorophenyl)-2-{(3R,6R)-3-(2,3-dihydro-1H-inden-2-yl)-4-[2-(dimethylamino)ethyl]-6-isobutyl-2,5-dioxopiperazin-1-yl}-N,N-dimethylethanamide |
| 38 | | 527.6 | 3.3 | 528 | 526 | [{(2R)-2-(2,4-difluorophenyl)-2-[(3R,6R)-3-(2,3-dihydro-1H-inden-2-yl)-6-isobutyl-2,5-dioxopiperazin-1-yl]ethanoyl}(methyl)amino]acetic acid |

| Eg No. | Regno | Mwt | Rt/ min | +ve ion | −ve ion | name |
|---|---|---|---|---|---|---|
| 39 | | 512.6 | 3.7 | 513 | 511 | tert-butyl (2R)-(2,4-difluorophenyl)[(3R,6R)-3-(2,3-dihydro-1H-inden-2-yl)-6-isobutyl-2,5-dioxopiperazin-1-yl]ethanoate |
| 40 | | 583.7 | 3.6 | 584 | none | tert-butyl [{(2R)-2-(2,4-difluorophenyl)-2-[(3R,6R)-3-(2,3-dihydro-1H-inden-2-yl)-6-isobutyl-2,5-dioxopiperazin-1-yl]ethanoyl}(methyl)amino]acetate |
| 41 | | 525.6 | 3.3 | 526 | 524 | (3R,6R)-1-[(1R)-1-(2,4-difluorophenyl)-2-(3-methoxyazetidin-1-yl)-2-oxoethyl]-3-(2,3-dihydro-1H-inden-2-yl)-6-isobutylpiperazine-2,5-dione |
| 42 | | 509.6 | 3.5 | 510 | none | (3R,6R)-1-[(1R)-1-(2,4-difluorophenyl)-2-oxo-2-pyrrolidin-1-ylethyl]-3-(2,3-dihydro-1H-inden-2-yl)-6-isobutylpiperazine-2,5-dione |

-continued

| Eg No. | Regno | Mwt | Rt/min | +ve ion | −ve ion | name |
|---|---|---|---|---|---|---|
| 43 | 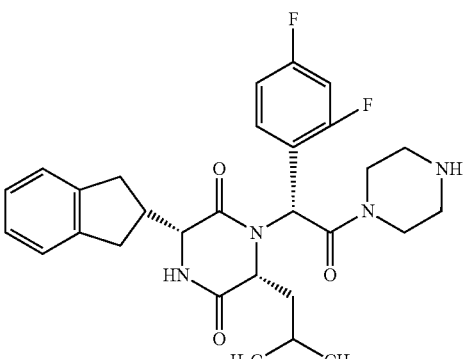 ClH | 561.1 | 2.7 | 525 | none | (3R,6R)-1-[(1R)-1-(2,4-difluorophenyl)-2-oxo-2-piperazin-1-ylethyl]-3-(2,3-dihydro-1H-inden-2-yl)-6-isobutylpiperazine-2,5-dione hydrochloride |
| 43a | 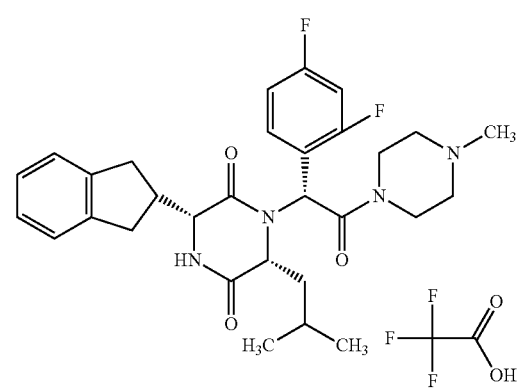 | 652.7 | 2.7 | 539 | 583 (M + 45) | (3R,6R)-1-[(1R)-1-(2,4-difluorophenyl)-2-(4-methylpiperazin-1-yl)-2-oxoethyl]-3-(2,3-dihydro-1H-inden-2-yl)-6-isobutylpiperazine-2,5-dione trifluoroacetate |
| 44 | 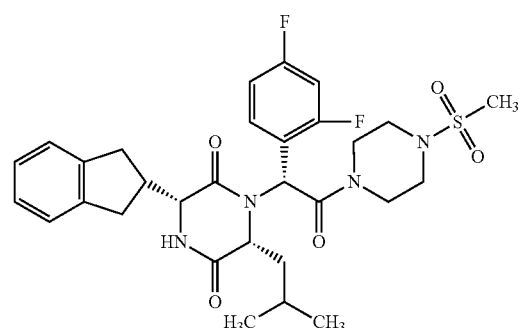 | 602.7 | 3.3 | 603 | 601 | (3R,6R)-1-{(1R)-1-(2,4-difluorophenyl)-2-[4-(methylsulfonyl)piperazin-1-yl]-2-oxoethyl}-3-(2,3-dihydro-1H-inden-2-yl)-6-isobutylpiperazine-2,5-dione |
| 45 | 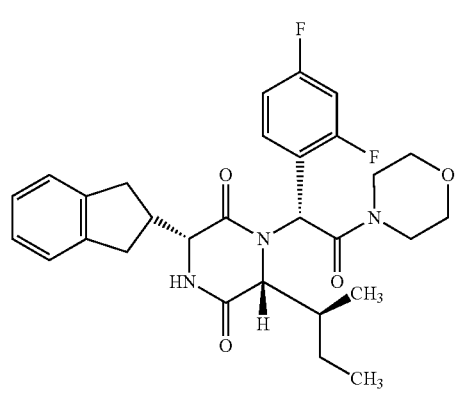 [SMILES: CC[C@H](C)[C@@H]1C(=O)N[C@H](C2Cc3ccccc3C2)C(=O)N1[C@@H](C(=O)N1CCOCC1)c1ccc(F)cc1F] | 525.6 | 3.2 | 526 | 524 | (3R,6R)-1-[(1R)-1-(2,4-difluorophenyl)-2-morpholin-4-yl-2-oxoethyl]-3-(2,3-dihydro-1H-inden-2-yl)-6-[(1S)-1-methylpropyl]piperazine-2,5-dione |

| Eg No. | Regno | Mwt | Rt/ min | +ve ion | −ve ion | name |
|---|---|---|---|---|---|---|
| 46 | | 525.6 | 3.2 | 526 | 524 | (3R,6R)-1-[(1R)-1-(2,4-difluorophenyl)-2-morpholin-4-yl-2-oxoethyl]-3-(2,3-dihydro-1H-inden-2-yl)-6-[(1R)-1-methylpropyl]piperazine-2,5-dione |
| 47 | | 541.7 | 3.6 | 542 | 540 | (3R,6R)-1-[(1R)-1-(2,4-difluorophenyl)-2-oxo-2-thiomorpholin-4-ylethyl]-3-(2,3-dihydro-1H-inden-2-yl)-6-isobutylpiperazine-2,5-dione |
| 48 | | 573.7 | 3.3 | 574 | 572 | (3R,6R)-1-[(1R)-1-(2,4-difluorophenyl)-2-(1,1-dioxidothiomorpholin-4-yl)-2-oxoethyl]-3-(2,3-dihydro-1H-inden-2-yl)-6-isobutylpiperazine-2,5-dione |
| 49 | | 557.7 | 3.1 | 558 | 556 | (3R,6R)-1-[(1R)-1-(2,4-difluorophenyl)-2-(1-oxidothiomorpholin-4-yl)-2-oxoethyl]-3-(2,3-dihydro-1H-inden-2-yl)-6-isobutylpiperazine-2,5-dione |

-continued

| Eg No. | Regno | Mwt | Rt/ min | +ve ion | −ve ion | name |
|---|---|---|---|---|---|---|
| 50 | | 560.6 | 3 | 561 | none | (2R)-2-(2,4-difluorophenyl)-2-[(3R,6R)-3-(2,3-dihydro-1H-inden-2-yl)-6-isobutyl-2,5-dioxopiperazin-1-yl]-N-methyl-N-(pyridin-4-ylmethyl)ethanamide |
| 51 | | 605.7 | 3.5 | 606 | 604 | (2R)-2-(2,4-difluorophenyl)-2-[(3R,6R)-3-(2,3-dihydro-1H-inden-2-yl)-6-isobutyl-2,5-dioxopiperazin-1-yl]-N-(3,4-dimethoxybenzyl)ethanamide |
| 52 | | 605.7 | 3.5 | 606 | 604 | (2S)-2-(2,4-difluorophenyl)-2-[(3R,6R)-3-(2,3-dihydro-1H-inden-2-yl)-6-isobutyl-2,5-dioxopiperazin-1-yl]-N-(3,4-dimethoxybenzyl)ethanamide |
| 53 | | 538.6 | 3.4 | 539 | 537 | (2R)-2-(2,4-difluorophenyl)-2-[(3R,6R)-3-(2,3-dihydro-1H-inden-2-yl)-6-isobutyl-2,5-dioxopiperazin-1-yl]-N-(1,3-thiazol-2-yl)ethanamide |

-continued

| Eg No. | Regno | Mwt | Rt/ min | +ve ion | −ve ion | name |
|---|---|---|---|---|---|---|
| 54 | | 511.6 | 3.6 | 512 | 510 | (2R)-N-(tert-butyl)-2-(2,4-difluorophenyl)-2-{(3R,6R)-3-(2,3-dihydro-1H-inden-2-yl)-6-[(1R)-1-methylpropyl]-2,5-dioxopiperazin-1-yl}ethanamide |
| 55 | | 511.6 | 3.6 | 512 | 510 | (2R)-N-(tert-butyl)-2-(2,4-difluorophenyl)-2-{(3R,6R)-3-(2,3-dihydro-1H-inden-2-yl)-6-[(1S)-1-methylpropyl]-2,5-dioxopiperazin-1-yl}ethanamide |
| 56 | | 437.5 | 3.3 | 438 | 436 | (2R)-2-[(3R,6R)-3-(2,3-dihydro-1H-inden-2-yl)-6-isobutyl-2,5-dioxopiperazin-1-yl]-2-(4-fluorophenyl)ethanamide |
| 57 | | 481.6 | 3 | 482 | 480 | (2R)-2-[(3R,6R)-3-(2,3-dihydro-1H-inden-2-yl)-6-isobutyl-2,5-dioxopiperazin-1-yl]-2-(4-fluorophenyl)-N-(2-hydroxyethyl)ethanamide |

| Eg No. | Regno | Mwt | Rt/ min | +ve ion | −ve ion | name |
|---|---|---|---|---|---|---|
| 58 | | 509.6 | 3.4 | 510 | 508 | [[(2R)-2-[(3R,6R)-3-(2,3-dihydro-1H-inden-2-yl)-6-isobutyl-2,5-dioxopiperazin-1-yl]-2-(4-fluorophenyl)ethanoyl](methyl)amino]acetic acid |
| 59 | | 509.6 | 3.4 | 510 | 508 | methyl {[(2R)-2-[(3R,6R)-3-(2,3-dihydro-1H-inden-2-yl)-6-isobutyl-2,5-dioxopiperazin-1-yl]-2-(4-fluorophenyl)ethanoyl]amino}acetate |
| 60 | | 564.7 | 2.6 | 565 | 563 | (3R,6R)-3-(2,3-dihydro-1H-inden-2-yl)-1-{(1R)-1-(4-fluorophenyl)-2-[4-(2-methoxyethyl)piperazin-1-yl]-2-oxoethyl}-6-isobutyl-piperazine-2,5-dione |
| 61 | | 534.7 | 2.6 | 535 | 533 | (3R,6R)-3-(2,3-dihydro-1H-inden-2-yl)-1-[(1R)-1-(4-fluorophenyl)-2-(4-methyl-1,4-diazapan-1-yl)-2-oxoethyl]-6-isobutylpiperazine-2,5-dione |

-continued

| Eg No. | Regno | Mwt | Rt/ min | +ve ion | −ve ion | name |
|---|---|---|---|---|---|---|
| 62 | | 548.7 | 2.6 | 549 | 547 | (3R,6R)-3-(2,3-dihydro-1H-inden-2-yl)-1-[(1R)-2-[4-(dimethylamino)piperidin-1-yl]-1-(4-fluorophenyl)-2-oxoethyl]-6-isobutylpiperazine-2,5-dione |
| 63 | | 550.7 | 2.7 | 551 | 549 | (2R)-2-[(3R,6R)-3-(2,3-dihydro-1H-inden-2-yl)-6-isobutyl-2,5-dioxopiperazin-1-yl]-2-(4-fluorophenyl)-N-(2-morpholin-4-ylethyl)ethanamide |
| 64 | | 548.7 | 2.8 | 549 | 547 | (2R)-2-[(3R,6R)-3-(2,3-dihydro-1H-inden-2-yl)-6-isobutyl-2,5-dioxopiperazin-1-yl]-2-(4-fluorophenyl)-N-(2-piperidin-1-ylethyl)ethanamide |
| 65 | | 619.7 | 3.9 | 620 | 618 | (2R)-N-[2-(benzyloxy)phenyl]-2-[(3R,6R)-3-(2,3-dihydro-1H-inden-2-yl)-6-isobutyl-2,5-dioxopiperazin-1-yl]-2-(4-fluorophenyl)ethanamide |

Similarly prepared:

| Eg No. | Regno | Mwt | Rt/ min | +ve ion | −ve ion | name |
|---|---|---|---|---|---|---|
| 66 | | 529.6 | 3.8 | 530 | 528 | (2R)-2-[(3R,6R)-3-(2,3-dihydro-1H-inden-2-yl)-6-isobutyl-2,5-dioxopiperazin-1-yl]-N-isopropyl-2-[4-(trifluoromethyl)phenyl]ethanamide |
| 67 | | 475.6 | 3.6 | 476 | 474 | (2R)-2-[(3R,6R)-3-(2,3-dihydro-1H-inden-2-yl)-6-isobutyl-2,5-dioxopiperazin-1-yl]-N-isopropyl-2-(4-methylphenyl)ethanamide |
| 68 | | 510.1 | 3.8 | 510 | 508 | (2R)-N-(tert-butyl)-2-(4-chlorophenyl)-2-[(3R,6R)-3-(2,3-dihydro-1H-inden-2-yl)-6-isobutyl-2,5-dioxopiperazin-1-yl]ethanamide |
| 69 | | 505.7 | 3.5 | 506 | 504 | (2R)-N-(tert-butyl)-2-[(3R,6R)-3-(2,3-dihydro-1H-inden-2-yl)-6-isobutyl-2,5-dioxopiperazin-1-yl]-2-(4-methoxyphenyl)ethanamide |

| Eg No. | Regno | Mwt | Rt/min | +ve ion | −ve ion | name |
|---|---|---|---|---|---|---|
| 70 | | 559.7 | 3.8 | 560 | 558 | (2R)-N-(tert-butyl)-2-[(3R,6R)-3-(2,3-dihydro-1H-inden-2-yl)-6-isobutyl-2,5-dioxopiperazin-1-yl]-2-(4-(trifluoromethoxy)phenyl]ethanamide |
| 71 | | 490.6 | 3.4 | 491 | 489 | (2R)-2-[(3R,6R)-3-(2,3-dihydro-1H-inden-2-yl)-6-isobutyl-2,5-dioxopiperazin-1-yl]-N-isopropyl-2-[4-(methylamino)phenyl]ethanamide |
| 72 | | 504.7 | 3.6 | 505 | 503 | (2R)-2-[(3R,6R)-3-(2,3-dihydro-1H-inden-2-yl)-6-isobutyl-2,5-dioxopiperazin-1-yl]-2-[4-(dimethylamino)phenyl]-N-isopropylethanamide |
| 73 | | 530.7 | 3.7 | 553 (M + Na) | 529 | (2R)-2-[(3R,6R)-3-(2,3-dihydro-1H-inden-2-yl)-6-isobutyl-2,5-dioxopiperazin-1-yl]-N-isopropyl-2-(4-pyrrolidin-1-ylphenyl)ethanamide |

-continued

| Eg No. | Regno | Mwt | Rt/ min | +ve ion | −ve ion | name |
|---|---|---|---|---|---|---|
| 74 | | 532.7 | 3.7 | 533 | 531 | (2R)-2-[4-(diethylamino)phenyl]-2-[(3R,6R)-3-(2,3-dihydro-1H-inden-2-yl)-6-isobutyl-2,5-dioxopiperazin-1-yl]-N-isopropylethanamide |
| 75 | | 504.6 | 3.1 | 505 | 503 | 4-[(1R)-1-[(3R,6R)-3-(2,3-dihydro-1H-inden-2-yl)-6-isobutyl-2,5-dioxopiperazin-1-yl]-2-(isopropylamino)-2-oxoethyl]benzamide |
| 76 | | 518.6 | 3.0 | 519 | 517 | (2R)-2-[4-(acetylamino)phenyl]-2-[(3R,6R)-3-(2,3-dihydro-1H-inden-2-yl)-6-isobutyl-2,5-dioxopiperazin-1-yl]-N-isopropylethanamide |
| 77 | | 532.7 | 3.2 | 533 | 531 | (2R)-2-[3-(acetylamino)phenyl]-N-(tert-butyl)-2-[(3R,6R)-3-(2,3-dihydro-1H-inden-2-yl)-6-isobutyl-2,5-dioxopiperazin-1-yl]ethanamide |

-continued

| Eg No. | Regno | Mwt | Rt/ min | +ve ion | −ve ion | name |
|---|---|---|---|---|---|---|
| 78 | | 539.7 | 3.3 | 540 | 538 | (2R)-2-[(3R,6R)-3-(2,3-dihydro-1H-inden-2-yl)-6-isobutyl-2,5-dioxopiperazin-1-yl]-N-isopropyl-2-[4-(methylsulfonyl)phenyl]ethanamide |
| 79 | | 532.7 | 3.3 | 533 | 531 | 4-{(1R)-2-(tert-butylamino)-1-[(3R,6R)-3-(2,3-dihydro-1H-inden-2-yl)-6-isobutyl-2,5-dioxopiperazin-1-yl]-2-oxoethyl}-N-methylbenzamide |
| 80 | | 568.7 | 3.4 | 569 | 567 | (2R)-N-(tert-butyl)-2-{(3R,6R)-3-(2,3-dihydro-1H-inden-2-yl)-6-[(1R)-1-methylpropyl]-2,5-dioxopiperazin-1-yl}-2-{4-[(methylamino)sulfonyl]phenyl}ethanamide |
| 81 | | 533.7 | 3.6 | 532 | 534 | methyl 4-{(1R)-2-(tert-butylamino)-1-[(3R,6R)-3-(2,3-dihydro-1H-inden-2-yl)-6-isobutyl-2,5-dioxopiperazin-1-yl]-2-oxoethyl}benzoate |

| Eg No. | Regno | Mwt | Rt/min | +ve ion | −ve ion | name |
|---|---|---|---|---|---|---|
| 82 | 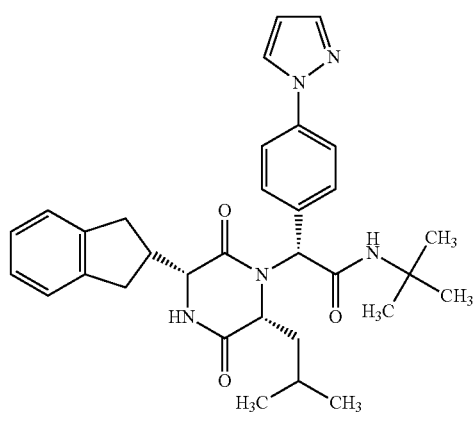 [SMILES: CC(C)C[C@@H]1C(=O)N[C@H](C2Cc3ccccc3C2)C(=O)N1[C@@H](C(=O)NC(C)(C)C)c1ccc(-n2cccn2)cc1] | 541.8 | 3.3 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[4-(1H-pyrazol-1-yl)phenyl]ethanamide |
| 83 | 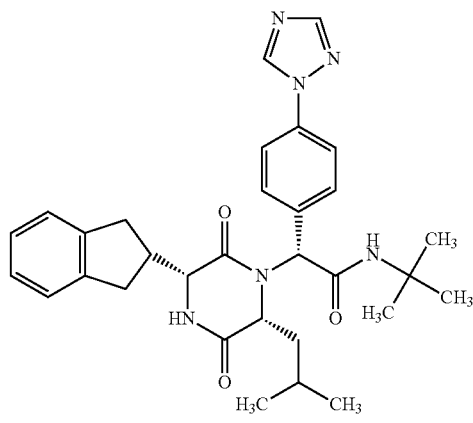 [SMILES: CC(C)C[C@@H]1C(=O)N[C@H](C2Cc3ccccc3C2)C(=O)N1[C@@H](C(=O)NC(C)(C)C)c1ccc(-n2cncn2)cc1] | 542.8 | 3.3 | 543 | 541 | (2R)-N-(tert-butyl)-2-[(3R,6R)-3-(2,3-dihydro-1H-inden-2-yl)-6-isobutyl-2,5-dioxopiperazin-1-yl]-2-[4-(1H-1,2,4-triazol-1-yl)phenyl]ethanamide |
| 84 | 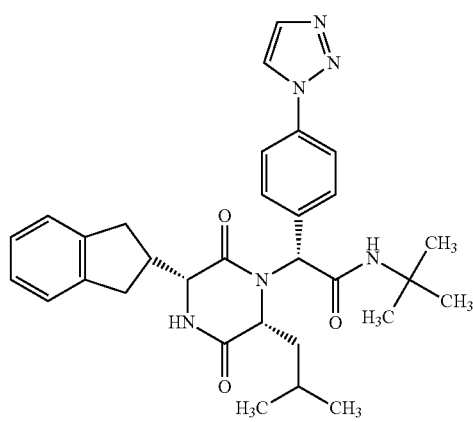 [SMILES: CC(C)C[C@@H]1C(=O)N[C@H](C2Cc3ccccc3C2)C(=O)N1[C@@H](C(=O)NC(C)(C)C)c1ccc(-n2ccnn2)cc1] | 542.8 | 3.2 | 543 | 541 | (2R)-N-(tert-butyl)-2-[(3R,6R)-3-(2,3-dihydro-1H-inden-2-yl)-6-isobutyl-2,5-dioxopiperazin-1-yl]-2-[4-(1H-1,2,3-triazol-1-yl)phenyl]ethanamide |

-continued

| Eg No. | Regno | Mwt | Rt/ min | +ve ion | −ve ion | name |
|---|---|---|---|---|---|---|
| 85 | | 541.7 | 3.5 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[3-(1H-pyrazol-3-yl)phenyl]ethanamide |
| 86 | | 541.8 | 3.3 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[4-(1H-pyrazol-3-yl)phenyl]ethanamide |
| 87 | | 519.4 | 3.4 | 520 | 518 | 3-{(1R)-2-(tert-butylamino)-1-[(3R,6R)-3-(2,3-dihydro-1H-inden-2-yl)-6-isobutyl-2,5-dioxopiperazin-1-yl]-2-oxoethyl}phenylboronic acid |
| 88 | | 541.7 | 3.0 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[4-(1H-imidazol-2-yl)phenyl]ethanamide |

| Eg No. | Regno | Mwt | Rt/min | +ve ion | −ve ion | name |
|---|---|---|---|---|---|---|
| 89 | 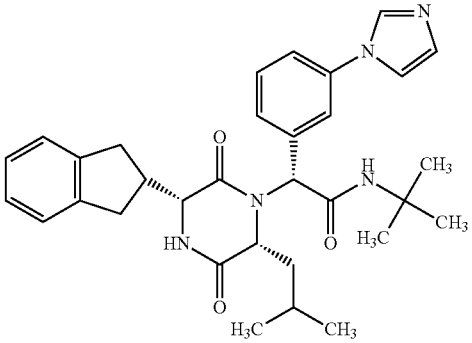 [SMILES: CC(C)C[C@@H]1C(=O)N[C@H](C2Cc3ccccc3C2)C(=O)N1[C@@H](C(=O)NC(C)(C)C)c1cccc(-n2ccnc2)c1] | 541.7 | 3.1 | 542.0 | 540 | (2R)-N-(tert-butyl)-2-[(3R,6R)-3-(2,3-dihydro-1H-inden-2-yl)-6-isobutyl-2,5-dioxopiperazin-1-yl]-2-[3-(1H-imidazol-1-yl)phenyl]ethanamide |
| 90 | 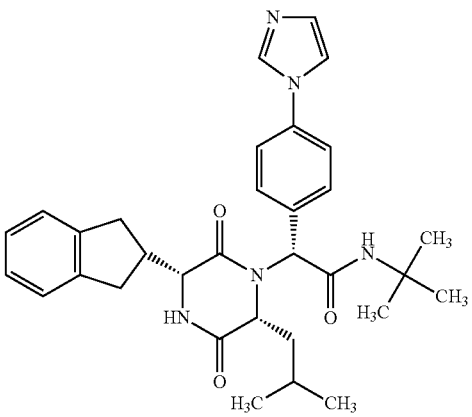 [SMILES: CC(C)C[C@@H]1C(=O)N[C@H](C2Cc3ccccc3C2)C(=O)N1[C@@H](C(=O)NC(C)(C)C)c1ccc(-n2ccnc2)cc1] | 541.7 | 3.0 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[4-(1H-imidazol-1-yl)phenyl]ethanamide |
| 91 | 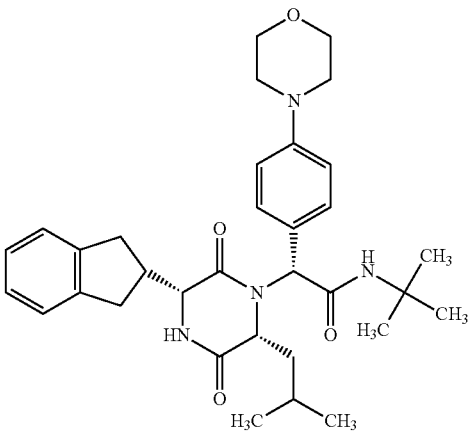 [SMILES: CC(C)C[C@@H]1C(=O)N[C@H](C2Cc3ccccc3C2)C(=O)N1[C@@H](C(=O)NC(C)(C)C)c1ccc(N2CCOCC2)cc1] | 560.8 | 3.4 | 561 | 559 | (2R)-N-(tert-butyl)-2-[(3R,6R)-3-(2,3-dihydro-1H-inden-2-yl)-6-isobutyl-2,5-dioxopiperazin-1-yl]-2-(4-morpholin-4-ylphenyl)ethanamide |

-continued

| Eg No. | Regno | Mwt | Rt/ min | +ve ion | −ve ion | name |
|---|---|---|---|---|---|---|
| 92 | | 541.7 | 3.3 | 542 | 540 | (2R)-N-(tert-butyl)-2-[(3R,6R)-3-(2,3-dihydro-1H-inden-2-yl)-6-isobutyl-2,5-dioxopiperazin-1-yl]-2-[4-(1H-pyrazol-4-yl)phenyl]ethanamide |
| 93 | | 599.8 | 3.9 | 600 | 598 | (2R)-N-(tert-butyl)-2-[4-(2-tert-butyl-2H-tetraazol-5-yl)phenyl]-2-[(3R,6R)-3-(2,3-dihydro-1H-inden-2-yl)-6-isobutyl-2,5-dioxopiperazin-1-yl]ethanamide |
| 94 | | 562.7 | 2.9 | 563 | none | (2R)-N-(tert-butyl)-2-[(3R,6R)-3-(2,3-dihydro-1H-inden-2-yl)-6-isobutyl-2,5-dioxopiperazin-1-yl]-2-{4-[2-(dimethylamino)ethoxy]phenyl}ethanamide trifluoroacetate |

| Eg No. | Regno | Mwt | Rt/ min | +ve ion | −ve ion | name |
|---|---|---|---|---|---|---|
| 95 | 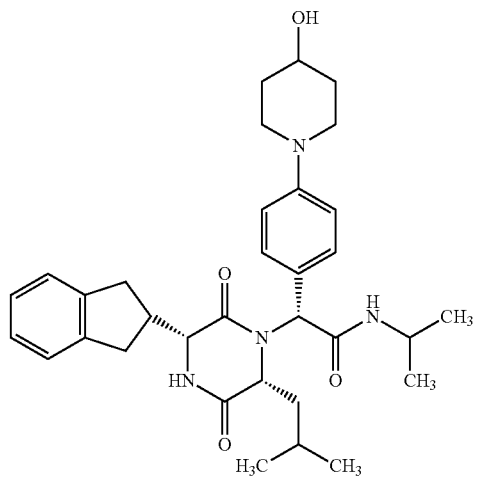 [SMILES: CC(C)C[C@@H]1C(=O)N[C@H](C2Cc3ccccc3C2)C(=O)N1[C@@H](C(=O)NC(C)C)c1ccc(N2CCC(O)CC2)cc1] | 560.8 | 3.0 | 561 | 559 | (2R)-2-[(3R,6R)-3-(2,3-dihydro-1H-inden-2-yl)-6-isobutyl-2,5-dioxopiperazin-1-yl]-2-[4-(4-hydroxypiperidin-1-yl)phenyl]-N-isopropylethanamide |
| 96 | 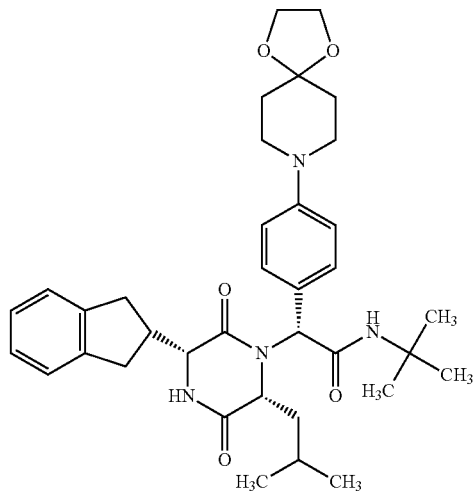 [SMILES: CC(C)C[C@@H]1C(=O)N[C@H](C2Cc3ccccc3C2)C(=O)N1[C@@H](C(=O)NC(C)(C)C)c1ccc(N2CCC3(CC2)OCCO3)cc1] | 616.9 | 3.5 | 617 | none | (2R)-N-(tert-butyl)-2-[(3R,6R)-3-(2,3-dihydro-1H-inden-2-yl)-6-isobutyl-2,5-dioxopiperazin-1-yl]-2-[4-(1,4-dioxa-8-azaspiro[4.5]dec-8-yl)phenyl]ethanamide |
| 97 | 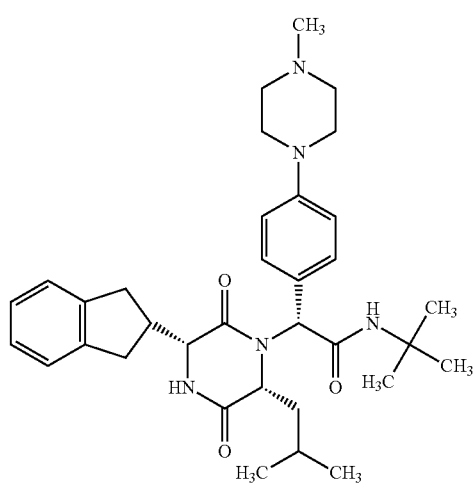 [SMILES: CC(C)C[C@@H]1C(=O)N[C@H](C2Cc3ccccc3C2)C(=O)N1[C@@H](C(=O)NC(C)(C)C)c1ccc(N2CCN(C)CC2)cc1] | 573.8 | 2.9 | 574 | none | (2R)-N-(tert-butyl)-2-[(3R,6R)-3-(2,3-dihydro-1H-inden-2-yl)-6-isobutyl-2,5-dioxopiperazin-1-yl]-2-[4-(4-methylpiperazin-1-yl)phenyl]ethanamide |

| Eg No. | Regno | Mwt | Rt/ min | +ve ion | −ve ion | name |
|---|---|---|---|---|---|---|
| 98 | 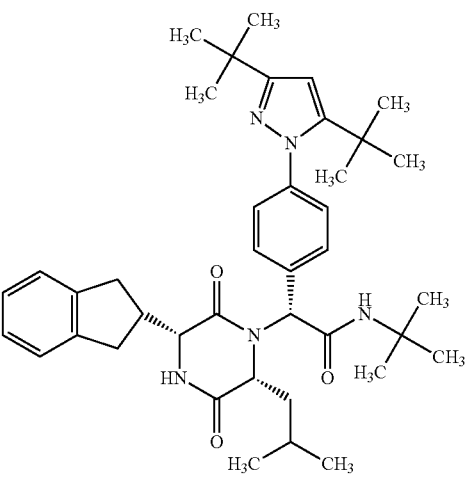 [SMILES: CC(C)C[C@@H]1C(=O)N[C@H](C2Cc3ccccc3C2)C(=O)N1[C@@H](C(=O)NC(C)(C)C)c1ccc(-n2nc(C(C)(C)C)cc2C(C)(C)C)cc1] | 654.0 | 4.1 | 654 | 652 | (2R)-N-(tert-butyl)-2-[4-(3,5-ditert-butyl-1H-pyrazol-1-yl)phenyl]-2-[(3R,6R)-3-(2,3-dihydro-1H-inden-2-yl)-6-isobutyl-2,5-dioxopiperazin-1-yl]ethanamide |
| 99 | 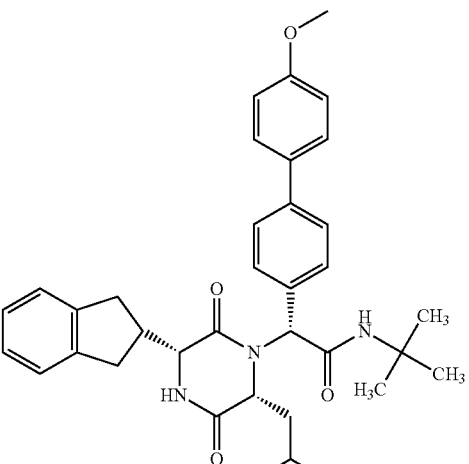 | 581.7 | 4.0 | 582 | 580 | (2R)-N-(tert-butyl)-2-[(3R,6R)-3-(2,3-dihydro-1H-inden-2-yl)-6-isobutyl-2,5-dioxopiperazin-1-yl]-2-(4'-methoxy-1,1'-biphenyl-4-yl)ethanamide |
| 100 | 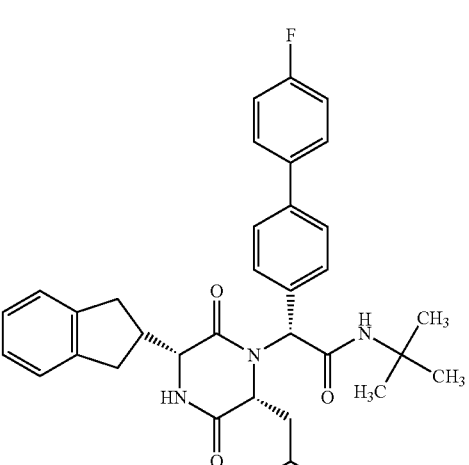 | 569.8 | 3.9 | none | 568 | (2R)-N-(tert-butyl)-2-[(3R,6R)-3-(2,3-dihydro-1H-inden-2-yl)-6-isobutyl-2,5-dioxopiperazin-1-yl]-2-(4'-fluoro-1,1'-biphenyl-4-yl)ethanamide |

-continued

| Eg No. | Regno | Mwt | Rt/ min | +ve ion | −ve ion | name |
|---|---|---|---|---|---|---|
| 101 | | 614.8 | 4.3 | 615 | 613 | (2R)-N-(tert-butyl)-2-[4-(4-tert-butyl-1,3-thiazol-2-yl)phenyl]-2-[(3R,6R)-3-(2,3-dihydro-1H-inden-2-yl)-6-isobutyl-2,5-dioxopiperazin-1-yl] ethanamide |
| 102 | | 658.9 | 3.6 | 659 | 657 | (2R)-N-(tert-butyl)-2-[(3R,6R)-3-(2,3-dihydro-1H-inden-2-yl)-6-isobutyl-2,5-dioxopiperazin-1-yl]-2-{4'-[(ethylamino)sulfonyl]-1,1'-biphenyl-4-yl} ethanamide |
| 103 | | 552.8 | 3.6 | 553 | 551 | (2R)-N-(tert-butyl)-2-[(3R,6R)-3-(2,3-dihydro-1H-inden-2-yl)-6-isobutyl-2,5-dioxopiperazin-1-yl]-2-(4-pyridin-2-ylphenyl)ethanamide |

-continued

| Eg No. | Regno | Mwt | Rt/ min | +ve ion | −ve ion | name |
|---|---|---|---|---|---|---|
| 104 | | 552.8 | 3.3 | 553 | 551 | (2R)-N-(tert-butyl)-2-[(3R,6R)-3-(2,3-dihydro-1H-inden-2-yl)-6-isobutyl-2,5-dioxopiperazin-1-yl]-2-(4-pyridin-3-ylphenyl)ethanamide |
| 105 | | 522.7 | 2.4 | 523 | none | (2R)-2-[(3R,6R)-3-(2,3-dihydro-1H-inden-2-yl)-6-isobutyl-2,5-dioxopiperazin-1-yl]-2-{4-[(dimethylamino)methyl]-2-fluorophenyl}-N,N-dimethylethanamide |
| 106 | | 495.6 | 2.9 | 496 | none | (2R)-2-[(3R,6R)-3-(2,3-dihydro-1H-inden-2-yl)-6-isobutyl-2,5-dioxopiperazin-1-yl]-2-[2-fluoro-4-(hydroxymethyl)phenyl]-N,N-dimethylethanamide |
| 107 | | | 3.4 | 498 | 496 | (2R)-2-(2,5-difluorophenyl)-2-[(3R,6R)-3-(2,3-dihydro-1H-inden-2-yl)-6-isobutyl-2,5-dioxopiperazin-1-yl]-N-isopropylethanamide |

-continued

| Eg No. | Regno | Mwt | Rt/ min | +ve ion | −ve ion | name |
|---|---|---|---|---|---|---|
| 108 | | | 3.6 | 512 | 510 | (2R)-N-(tert-butyl)-2-(3,4-difluorophenyl)-2-[(3R,6R)-3-(2,3-dihydro-1H-inden-2-yl)-6-isobutyl-2,5-dioxopiperazin-1-yl]ethanamide |
| 109 | | | 3.6 | 512 | 510 | (2R)-N-(tert-butyl)-2-(3,5-difluorophenyl)-2-[(3R,6R)-3-(2,3-dihydro-1H-inden-2-yl)-6-isobutyl-2,5-dioxopiperazin-1-yl]ethanamide |
| 110 | | | 3.6 | 512 | 510 | (2R)-N-(tert-butyl)-2-(2,3-difluorophenyl)-2-[(3R,6R)-3-(2,3-dihydro-1H-inden-2-yl)-6-isobutyl-2,5-dioxopiperazin-1-yl]ethanamide |
| 111 | | | 3.7 | 530 | 528 | (2R)-N-(tert-butyl)-2-[(3R,6R)-3-(2,3-dihydro-1H-inden-2-yl)-6-isobutyl-2,5-dioxopiperazin-1-yl]-2-(2,4,5-trifluorophenyl)ethanamide |

| Eg No. | Regno | Mwt | Rt/ min | +ve ion | −ve ion | name |
|---|---|---|---|---|---|---|
| 112 | 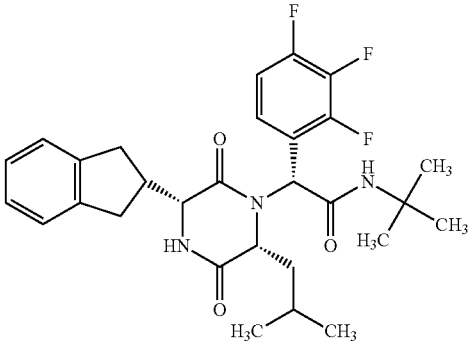 [SMILES: CC(C)C[C@@H]1C(=O)N[C@H](C2Cc3ccccc3C2)C(=O)N1[C@@H](C(=O)NC(C)(C)C)c1ccc(F)c(F)c1F] | | 3.7 | 530 | 528 | (2R)-N-(tert-butyl)-2-[(3R,6R)-3-(2,3-dihydro-1H-inden-2-yl)-6-isobutyl-2,5-dioxopiperazin-1-yl]-2-(2,3,4-trifluorophenyl)ethanamide |
| 113 | 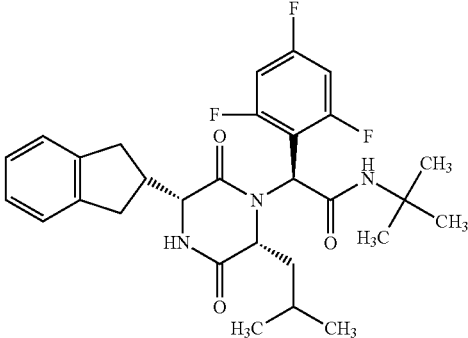 [SMILES: CC(C)C[C@@H]1C(=O)N[C@H](C2Cc3ccccc3C2)C(=O)N1[C@H](C(=O)NC(C)(C)C)c1c(F)cc(F)cc1F] | | 3.6 | 530 | 528 | (2S)-N-(tert-butyl)-2-[(3R,6R)-3-(2,3-dihydro-1H-inden-2-yl)-6-isobutyl-2,5-dioxopiperazin-1-yl]-2-(2,4,6-trifluorophenyl)ethanamide |
| 114 | 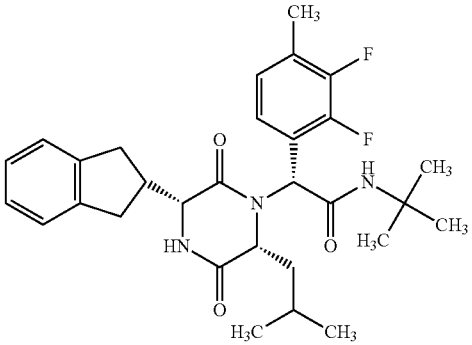 [SMILES: Cc1ccc([C@H](C(=O)NC(C)(C)C)N2C(=O)[C@@H](C3Cc4ccccc4C3)NC(=O)[C@H]2CC(C)C)c(F)c1F] | | 3.8 | 526 | 524 | (2R)-N-(tert-butyl)-2-(2,3-difluoro-4-methylphenyl)-2-[(3R,6R)-3-(2,3-dihydro-1H-inden-2-yl)-6-isobutyl-2,5-dioxopiperazin-1-yl]ethanamide |
| 115 | 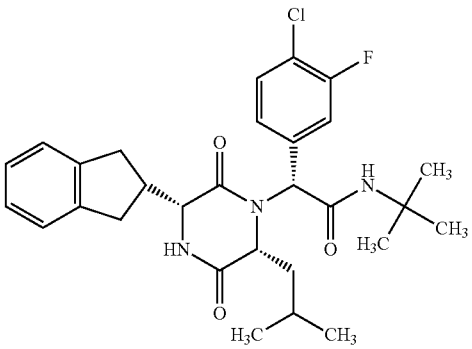 [SMILES: CC(C)C[C@@H]1C(=O)N[C@H](C2Cc3ccccc3C2)C(=O)N1[C@@H](C(=O)NC(C)(C)C)c1ccc(Cl)c(F)c1] | | 3.8 | 528 | 526 | (2R)-N-(tert-butyl)-2-(4-chloro-3-fluorophenyl)-2-[(3R,6R)-3-(2,3-dihydro-1H-inden-2-yl)-6-isobutyl-2,5-dioxopiperazin-1-yl]ethanamide |

-continued

| Eg No. | Regno | Mwt | Rt/ min | +ve ion | −ve ion | name |
|---|---|---|---|---|---|---|
| 116 | | | 3.7 | 530 | 528 | (2R)-2-(3,4-dichlorophenyl)-2-{(3R,6R)-3-(2,3-dihydro-1H-inden-2-yl)-6-[(1S)-1-methylpropyl]-2,5-dioxopiperazin-1-yl}-N-isopropylethanamide |
| 117 | | | 3.7 | 580 | 578 | (2R)-2-[3-chloro-4-(trifluoromethoxy)phenyl]-2-[(3R,6R)-3-(2,3-dihydro-1H-inden-2-yl)-6-isobutyl-2,5-dioxopiperazin-1-yl]-N-isopropylethanamide |
| 118 | | | 3.0 | 482 | 480 | (2R)-2-[(3R,6R)-3-(2,3-dihydro-1H-inden-2-yl)-6-isobutyl-2,5-dioxopiperazin-1-yl]-2-(3-fluoro-4-hydroxyphenyl)-N,N-dimethylethanamide |
| 119 | | | 3.3 | 496 | 494 | (2R)-2-[(3R,6R)-3-(2,3-dihydro-1H-inden-2-yl)-6-isopropyl-2,5-dioxopiperazin-1-yl]-2-(3-fluoro-4-methoxyphenyl)-N-isopropylethanamide |

| Eg No. | Regno | Mwt | Rt/ min | +ve ion | −ve ion | name |
|---|---|---|---|---|---|---|
| 120 | 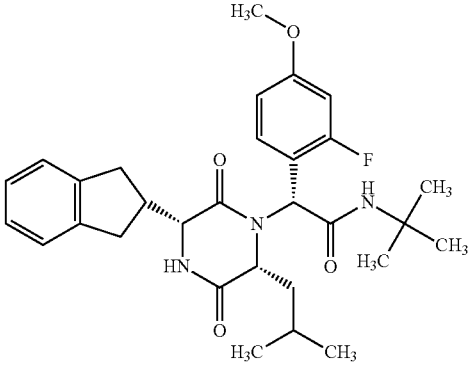 [SMILES: COc1ccc([C@H](C(=O)NC(C)(C)C)N2C(=O)[C@@H](C3Cc4ccccc4C3)NC(=O)[C@H]2CC(C)C)c(F)c1] | | 3.6 | 524 | 522 | (2R)-N-(tert-butyl)-2-[(3R,6R)-3-(2,3-dihydro-1H-inden-2-yl)-6-isobutyl-2,5-dioxopiperazin-1-yl]-2-(2-fluoro-4-methoxyphenyl)ethanamide |
| 121 | 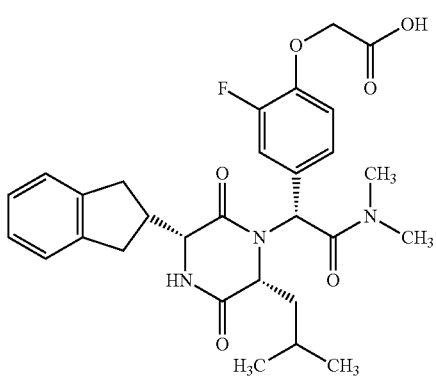 [SMILES: CC(C)C[C@@H]1C(=O)N[C@H](C2Cc3ccccc3C2)C(=O)N1[C@@H](C(=O)N(C)C)c1ccc(OCC(=O)O)c(F)c1] | | 3.1 | 540 | 538 | {4-[(1R)-1-[(3R,6R)-3-(2,3-dihydro-1H-inden-2-yl)-6-isobutyl-2,5-dioxopiperazin-1-yl]-2-(dimethylamino)-2-oxoethyl]-2-fluorophenoxy}acetic acid |
| 122 | 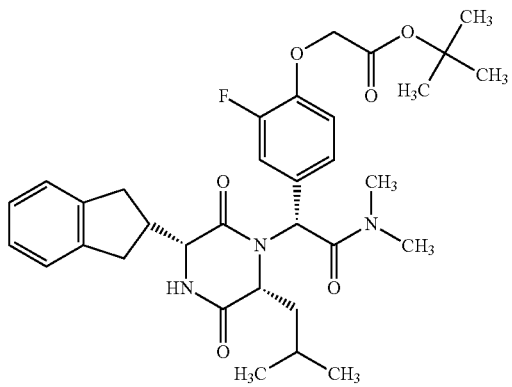 [SMILES: CC(C)C[C@@H]1C(=O)N[C@H](C2Cc3ccccc3C2)C(=O)N1[C@@H](C(=O)N(C)C)c1ccc(OCC(=O)OC(C)(C)C)c(F)c1] | | 3.6 | 596 | 594 | tert-butyl {4-[(1R)-1-[(3R,6R)-3-(2,3-dihydro-1H-inden-2-yl)-6-isobutyl-2,5-dioxopiperazin-1-yl]-2-(dimethylamino)-2-oxoethyl]-2-fluorophenoxy}acetate |
| 123 | 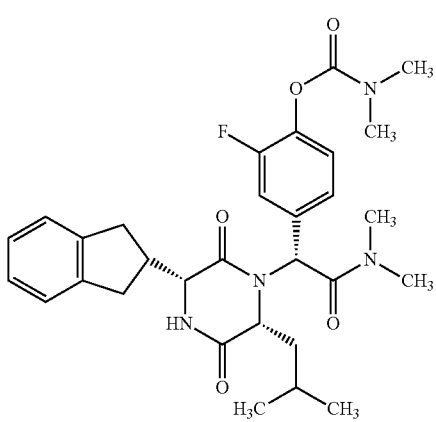 [SMILES: CC(C)C[C@@H]1C(=O)N[C@H](C2Cc3ccccc3C2)C(=O)N1[C@@H](C(=O)N(C)C)c1ccc(OC(=O)N(C)C)c(F)c1] | | 3.3 | 553 | none | 4-[(1R)-1-[(3R,6R)-3-(2,3-dihydro-1H-inden-2-yl)-6-isobutyl-2,5-dioxopiperazin-1-yl]-2-(dimethylamino)-2-oxoethyl]-2-fluorophenyl dimethylcarbamate |

| Eg No. | Regno | Mwt | Rt/ min | +ve ion | −ve ion | name |
|---|---|---|---|---|---|---|
| 124 | | | 3.5 | none | 552 | (2R)-N-(tert-butyl)-2-[(3R,6R)-3-(2,3-dihydro-1H-inden-2-yl)-6-isobutyl-2,5-dioxopiperazin-1-yl]-2-(2-fluoro-4,5-dimethoxyphenyl)ethanamide |
| 125 | | | 3.7 | 524 | 522 | (2R)-N-(tert-butyl)-2-[(3R,6R)-3-(2,3-dihydro-1H-inden-2-yl)-6-isobutyl-2,5-dioxopiperazin-1-yl]-2-(4-fluoro-3-methoxyphenyl)ethanamide |
| 126 | | | 3.8 | none | 570/572 | (2R)-2-(4-bromo-2-fluorophenyl)-N-(tert-butyl)-2-[(3R,6R)-3-(2,3-dihydro-1H-inden-2-yl)-6-isobutyl-2,5-dioxopiperazin-1-yl]ethanamide |
| 127 | | | 3.5 | 523 | 521 | (2R)-2-[(3R,6R)-3-(2,3-dihydro-1H-inden-2-yl)-6-isobutyl-2,5-dioxopiperazin-1-yl]-2-[4-(dimethylamino)-3-fluorophenyl]-N-isopropylethanamide |

| Eg No. | Regno | Mwt | Rt/min | +ve ion | −ve ion | name |
|---|---|---|---|---|---|---|
| 128 | | | 3.7 | 540 | 538 | (2R)-N-(tert-butyl)-2-(3-chloro-4-methoxyphenyl)-2-[(3R,6R)-3-(2,3-dihydro-1H-inden-2-yl)-6-isobutyl-2,5-dioxopiperazin-1-yl]ethanamide |
| 129 | | | 3.3 | 565 | 563 | (2R)-2-[(3R,6R)-3-(2,3-dihydro-1H-inden-2-yl)-6-isobutyl-2,5-dioxopiperazin-1-yl]-2-(3-fluoro-4-morpholin-4-ylphenyl)-N-isopropylethanamide |
| 130 | | | 3.2 | 579 | 577 | (2R)-2-[(3R,6R)-3-(2,3-dihydro-1H-inden-2-yl)-6-isobutyl-2,5-dioxopiperazin-1-yl]-2-[2-fluoro-4-(4-hydroxypiperidin-1-yl)phenyl]-N-isopropylethanamide |

| Eg No. | Regno | Mwt | Rt/ min | +ve ion | −ve ion | name |
|---|---|---|---|---|---|---|
| 131 | [structure] | | 3.3 | 587 | 585 | (2R)-N-(tert-butyl)-2-[(3R,6R)-3-(2,3-dihydro-1H-inden-2-yl)-6-isobutyl-2,5-dioxopiperazin-1-yl]-2-{2-fluoro-4-[(methylsulfonyl)amino]phenyl}ethanamide |

Hydroxylated metabolites of (2R)-2-(2,4-difluorophenyl)-2-[(3R,6R)-3-(2,3-dihydro-1H-inden-2-yl)-6-isobutyl-2,5-dioxopiperazin-1-yl]-N,N-dimethylethanamide were prepared as follows:

2 liters of growing cell cultures of *Streptomyces rimosus* BS33 was used to biotransform GW796679x. 500 mg of GW796679X was added after 3 days growth and the broth harvested after another 5 days incubation. At harvest, 2 liters of methanol was added, then the cells removed by centrifugation. Methanol was removed from the supernatant by evaporation. The compounds were then extracted with ethyl acetate, evaporated to dryness, and purified by preparative HPLC to give examples 132, 133, 134 and 135.

| Eg No. | Regno | Mwt | Rt/ min | +ve ion | −ve ion | name |
|---|---|---|---|---|---|---|
| 132 | [structure] | 485.5 | 2.9 | 486 | 484 | (2R)-2-(2,4-difluorophenyl)-2-{(3R,6R)-3-[(2S)-5-hydroxy-2,3-dihydro-1H-inden-2-yl]-6-isobutyl-2,5-dioxopiperazin-1-yl}-N-methylethanamide |
| 133 | [structure] | 485.5 | 2.9 | 486 | 484 | (2R)-2-(2,4-difluorophenyl)-2-{(3R,6R)-3-[(2R)-1-hydroxy-2,3-dihydro-1H-inden-2-yl]-6-isobutyl-2,5-dioxopiperazin-1-yl}-N-methylethanamide |

| | | | | | |
|---|---|---|---|---|---|
| 134 | [structure] | 485.5 | 2.9 | 486 | 484 | (2R)-2-(2,4-difluorophenyl)-2-{(3R,6R)-3-[(2R)-1-hydroxy-2,3-dihydro-1H-inden-2-yl]-6-isobutyl-2,5-dioxopiperazin-1-yl}-N-methylethanamide |
| 135 | [structure] | 485.5 | 3.1 | 486 | 530 (M + 45) | (2R)-2-(2,4-difluorophenyl)-2-[(3R,6R)-3-(2,3-dihydro-1H-inden-2-yl)-6-isobutyl-2,5-dioxopiperazin-1-yl]-N-(hydroxymethyl)ethanamide |

EXAMPLE 136

(2R)-2-(1-benzofuran-5-yl)-2-[(3R,6R)-3-(2,3-dihydro-1H-inden-2-yl)-6-isobutyl-2,5-dioxopiperazin-1-yl]-N-isopropylethanamide Benzofuran-5-carboxaldehyde (215 mg, 1.47 mmol) and D-leucine t-butyl ester hydrochloride (329 mg, 1.47 mmol) were dissolved in methanol (1.5 ml) and triethylamine (0.205 ml, 1.47 mmol) added. The mixture, a pale yellow solution, was left to stand at room temperature overnight (23.5 hours). Then Boc-D-indanylglycine (429 mg, 1.47 mmol) was added followed by isopropylisonitrile (0.138 ml, 1.51 mmol). The mixture, a yellow solution, was left to stand at room temperature overnight (23.5 hours) before the solvent was evaporated under reduced pressure to leave a yellow gum. The gum was dissolved in 4M hydrogen chloride in dioxan (3 ml, 12 mmol) and left to stand at room temperature for 7.5 hours before it was evaporated under reduced pressure to leave an orange/brown gum. The gum was dissolved in methanol (2 ml) and 4M hydrogen chloride in dioxan (1 ml, 4 mmol) added. The mixture was left to stand at room temperature for 5.5 hours before the solvent was removed by evaporation under reduced pressure. The residue was dissolved in dichloromethane (4 ml) and triethylamine (0.5 ml, excess) added. The mixture was stirred at room temperature overnight (18.3 hours) before the solvent was removed by evaporation under reduced pressure. The residue was loaded in dichloromethane onto a SPE column (10 g silica, Mega Bond Elut cartridge, pre-eluted with cyclohexane). The column was eluted stepwise (40-45 ml each step) with 100% chloroform, 3:1 cyclohexane:diethyl ether, 1:1 cyclohexane:diethyl ether, 1:3 cyclohexane:diethyl ether, 100% diethyl ether, 1:1 cyclohexane:ethyl acetate, 1:2 cyclohexane:ethyl acetate and 100% ethyl acetate. The 1:3 cyclohexane:diethyl ether to 1:2 cyclohexane:ethyl acetate fractions inclusive were combined to give a pale yellow solid (336 mg). The solid was loaded in dichloromethane onto 6 preparative chromatography plates (silica gel 60 plates, 20×20 cm$^2$). The plates were eluted four times with 30:1 dichloromethane:isopropanol. The required band was extracted with 9:1 ethyl acetate:methanol to give (2R)-2-(1-benzofuran-5-yl)-2-[(3R,6R)-3-(2,3-dihydro-1H-inden-2-yl)-6-isobutyl-2,5-dioxopiperazin-1-yl]-N-isopropylethanamide as a white solid (141 mg, 0.28 mmol)

HPLC Rt=3.46 minutes; m/z [M+H]$^+$=502.

$^1$H NMR δ 7.95 (d, 1H), 7.73 (d, 1H), 7.68 (d, 1H), 7.53 (d, 1H), 7.37 (dd, 1H), 7.16 (m, 4H), 6.79 (d, 1H), 5.79 (d, 1H), 5.37 (s, 1H), 4.11 (m, 1H), 4.03 (br dd, 1H), 3.99 (dd, 1H), 3.16-2.97 (m, 3H), 2.95-2.78 (m, 2H), 1.79 (m, 1H), 1.69 (m, 1H), 1.33 (m, 1H), 1.09 (t, 6H), 0.78 (d, 3H), 0.67 (d, 3H).

Similarly prepared

EXAMPLE 137

(2R)-2-(1,2,3-benzothiadiazol-6-yl)-N-(tert-butyl)-2-[(3R,6R)-3-(2,3-dihydro-1H-inden-2-yl)-6-isobutyl-2,5-dioxopiperazin-1-yl]ethanamide HPLC Rt=3.50 minutes; m/z [M+H]$^+$=534.

$^1$H NMR δ 8.66 (d, 1H), 7.82 (d, 1H), 7.67 (dd, 1H), 7.20 (m, 4H), 6.72 (br d, 1H), 6.13 (s, 1H), 5.19 (s, 1H), 4.06 (br dd, 1H), 4.00 (dd, 1H), 3.18 (m, 1H), 3.07 (m, 2H), 2.92 (m, 1H), 2.81 (m, 1H), 1.86 (m, 1H), 1.80 (m, 1H), 1.54 (m, 1H), 1.36 (s, 9H), 0.85 (d, 3H), 0.78 (d, 3H).

EXAMPLE 138

(2R)-2-(2,3-dihydro-1-benzofuran-5-yl)-2-[(3R,6R)-3-(2,3-dihydro-1H-inden-2-yl)-6-isobutyl-2,5-dioxopiperazin-1-yl]-N-isopropylethanamide HPLC Rt=3.34 minutes; m/z [M+H]$^+$=504.

$^1$H NMR δ 7.81 (br s, 1H), 7.18 (m, 5H), 6.79 (d, 1H), 6.44 (br d, 1H), 5.50 (d, 1H), 5.06 (s, 1H), 4.61 (t, 2H), 4.08 (m,

1H), 3.96 (m, 2H), 3.22 (t, 2H), 3.15 (m, 1H), 3.07 (d, 2H), 2.90 (m, 1H), 2.79 (dd, 1H), 1.82 (m, 1H), 1.71 (m, 1H), 1.42 (m, 1H), 1.12 (dd, 6H), 0.83 (d, 3H), 0.77 (d, 3H).

EXAMPLE 139

(2R)-2-(1,3-benzodioxol-5-yl)-N-(tert-butyl)-2-[(3R,6R)-3-(2,3-dihydro-1H-inden-2-yl)-6-isobutyl-2,5-dioxopiperazin-1-yl]ethanamide HPLC Rt=3.48; m/z [M+H]$^+$=520
$^1$H NMR (CDCl$_3$) δ 7.21 (m, 2H), 7.16 (m, 2H), 6.97 (d, 1H), 6.88 (dd, 1H), 6.82 (d, 1H), 6.58 (m, 1H), 6.06 (m, 2H), 5.64 (s, 1H), 5.02 (m, 1H), 3.95 (m, 2H), 3.16 (m, 1H), 3.07 (m, 2H), 2.89 (m, 1H), 2.77 (m, 1H), 1.82 (m, 1H), 1.71 (m, 1H), 1.41 (m, 1H), 1.32 (s, 9H), 0.83 (d, 3H), 0.79 (d, 3H)

EXAMPLE 140

(2R)-2-(benzofuran-5-yl)-2-[(3R,6R)-3-(2,3-dihydro-1H-inden-2-yl)-6-isobutyl-2,5-dioxopiperazin-1-yl]-N,N-dimethylethanamide Methyl N-[(1R)-2-{[2-(benzyloxy)phenyl]amino}-1-(benzofuran-5-yl)-2-oxoethyl]-L-leucinate To a suspension of L-leucine (2.62 g) in methanol (250 ml) at −30° C. under nitrogen was added a solution of benzofuran-5-carbaldehyde (2.92 g) in methanol (15 ml) and a suspension of 2-benzyloxyphenylisonitrile (4.19 g) in methanol (15 ml). The reaction was stirred at −30° C. for 2 hours and then allowed to warm to room temperature and stirred for a further 3 days. The solvent was removed in vacuo and the residue was passed through a Biotage™ column (3×90 g) eluting with cyclohexane:ethyl acetate (5:1) to afford after evaporation of the appropriate fractions methyl N-[(1R)-2-{[2(benzyloxy)phenyl]amino}-1-(benzofuran-5-yl)-2-oxoethyl]-L-leucinate (5.11 g).
HPLC Rt=3.97 minutes, m/z [M+H]$^+$=499

Methyl N-{(1R)-1-(benzofuran-5-yl)-2-[(2-hydroxyphenyl)amino]-2-oxoethyl}-L-leucinate A mixture of palladium on carbon (10%, 500 mg), methyl N-[(1R)-2-{[2-(benzyloxy)phenyl]amino}-1-(benzofuran-5-yl)-2-oxoethyl]-L-leucinate (5.1 g) and ethyl acetate (60 ml) was stirred under a hydrogen atmosphere for 5 hours. The reaction was then filtered through Celite and the filter pad was washed with further portions of ethyl acetate. The combined organic fractions were evaporated to give methyl N-{(1R)-1-(benzofuran-5-yl)-2-[(2-hydroxyphenyl)amino]-2-oxoethyl}-L-leucinate (3.429 g).
HPLC Rt=3.49 min, m/z [M+H]$^+$=411

Methyl N-[1-(benzofuran-5-yl)-2-(dimethylamino)-2-oxoethyl]-L-leucinate

A solution of methyl N-{(1R)-1-(benzofuran-5-yl)-2-[(2-hydroxyphenyl)amino]-2-oxoethyl}-L-leucinate (410 mg) and 1,1'-thiocarbonyldiimidazole (196 mg) in dichloromethane (5 ml) was left to stand for 18 hours. Water (20 l) was added to the reaction mixture and this was then stirred rapidly for 30 minutes. After this, 1H-Benzotriazolium, 1-[bis(dimethylamino)methylene]-, tetrafluoroborate (1-), 3-oxide (TBTU, 710 mg) and a solution of dimethylamine in tetrahydrofuran (3 ml of 2M solution) were added. The reaction mixture was stirred for a further 18 hours and was then passed down an SPE (5 g, silica) eluting with a gradient (3:1 to 1:2 cyclohexane:ethyl acetate). The required fractions were combined and evaporated to furnish methyl N-[1-(benzofuran-5-yl)-2-(dimethylamino)-2-oxoethyl]-L-leucinate (140 mg).
HPLC Rt=2.70 minutes m/z [M+H]$^+$=347

N-[1-(benzofuran-5-yl)-2-(dimethylamino)-2-oxoethyl]-L-leucine

To a solution of methyl N-[1-(benzofuran-5-yl)-2-(dimethylamino)-2-oxoethyl]-L-leucinate (520 mg) in methanol (5 ml) was added a solution of lithium hydroxide (91 mg) in water (3 ml). After stirring vigorously for 24 hours the solvent was removed in vacuo. The residue was diluted with water (10 ml) then neutralised with 2N hydrochloric acid. This solution was applied to an Oasis™ cartridge (2×6 g) and eluted with water (×2) and methanol (×2). The required fractions were combined and evaporated to afford N-[1-(benzofuran-5-yl)-2-(dimethylamino)-2-oxoethyl]-L-leucine (478 mg).
HPLC Rt=2.27 minutes m/z [M+H]$^+$=333

(2R)-2-(benzofuran-5-yl)-2-[(3R,6R)-3-(2,3-dihydro-1H-inden-2-yl)-6-isobutyl-2,5-dioxopiperazin-1-yl]-N,N-dimethylethanamide To a solution of (2R)-[(tert-butoxycarbonyl)amino](2,3-dihydro-1H-inden-2-yl)ethanoic acid (419 mg) in dry tetrahydrofuran (5 ml) at −20° C. under a nitrogen atmosphere was added N-methylmorpholine (158 μl) and a solution of isopropylchloroformate in toluene (1.0M, 1.44 ml). After 10 minutes, a solution of N-[1-(benzofuran-5-yl)-2-(dimethylamino)-2-oxoethyl]-L-leucine (478 mg) in dimethylformamide (5 ml) was added and the reaction was allowed to warm to room temperature. After 20 hours, the solvent was removed in vacuo and the residue was dissolved in 4N hydrochloric acid in dioxan (4 ml). After 4 hours methanol (13 ml) was added and the reaction was left to stand for a further 18 hours. The solvent was then removed in vacuo and the residue was separated between dichloromethane and saturated sodium bicarbonate solution. The organic phase was evaporated in vacuo and the residue was applied to an SPE (10 g, silica). The product was eluted using an ethyl acetate:methanol gradient (3:1 to 1:3) to afford (2R)-2-(benzofuran-5-yl)-2-[(3R,6R)-3-(2,3-dihydro-1H-inden-2-yl)-6-isobutyl-2,5-dioxopiperazin-1-yl]-N,N-dimethylethanamide (51 mg).
HPLC Rt=3.36 minutes, m/z [M+H]$^+$=488
$^1$H NMR (D$_6$-DMSO) δ 8.47 (d, 1H), 8.07 (d, 1H), 7.71 (m, 1H), 7.69 (d, 1H), 7.38 (dd, 1H), 7.21 (m, 2H), 7.12 (m, 2H), 7.03 (m, 1H), 6.47 (s, 1H), 3.88 (m, 1H), 3.69 (dd, 1H), 3.07-2.67 (m, 5H), 2.87 (s, 3H), 2.77 (s, 3H), 1.40-1.70 (m, 2H), 0.46 (m, 1H), 0.42 (d, 3H), 0.02 (d, 3H)

EXAMPLE 141

(2R)-2-[(3R,6R)-3-(2,3-dihydro-1H-inden-2-yl)-6-isobutyl-2,5-dioxopiperazin-1-yl]-N,N-dimethyl-2-(2-methyl-1-benzofuran-5-yl)ethanamide (2RS)-2-(2-methyl-1-benzofuran-5-yl)-2-[(3R,6R)-3-(2,3-dihydro-1H-inden-2-yl)-6-isobutyl-2,5-dioxopiperazin-1-yl]-N-(2-hydroxyphenyl)ethanamide A mixture of 2-methyl-5-formylbenzofuran (1.26 g), (D)-leucine methyl ester hydrochloride (1.57 g), triethylamine (1.2 ml) and methanol (20 ml) was stirred at room temperature for 6 hours and then left to stand for 19 hours. N-benzylcarbonyl-(D)-indanylglycine (2.80 g) and 2-benzyloxy-phenylisocyanide (1.89 g) were then added sequentially and the mixture stirred for 2 days. The reaction mixture was concentrated under reduced pressure and diluted with ethyl acetate. This was washed with 1N hydrochloric acid, saturated sodium bicarbonate solution and brine. The organic phase was dried over MgSO₄ and concentrated in vacuo. The residue was diluted with ethyl acetate (100 ml) and acetic acid (10 ml) and hydrogenated at atmospheric pressure over 10% palladium on activated carbon (1.5 g). After 4 hours the catalyst was removed by filtration through a pad of celite and washed with dichloromethane/methanol (500 ml of 1:1 v/v). The filtrate and washings were combined, evaporated under reduced pressure. The residue was separated between ethyl acetate and water. The organic phase was washed with water, saturated sodium bicarbonate solution and brine. The organic phase was dried over MgSO₄ and evaporated under reduced pressure. The residue was applied to a silica cartridge (100 g) and eluted with cyclohexane/ethyl acetate (500 ml of 3:1, 2:1, 1:1 v/v) and ethyl acetate (500 ml). The required fractions were combined and evaporated in vacuo to give (2RS)-2-(2-methylbenzofuran-5-yl)-2-[(3R,6R)-3-(2,3-dihydro-1H-inden-2-yl)-6-isobutyl-2,5-dioxopiperazin-1-yl]-N-(2-hydroxyphenyl)ethanamide (1.58 g).

HPLC Rt=3.60 minutes; m/z [M+H]⁺=566.

(2R)-2-[(3R,6R)-3-(2,3-dihydro-1H-inden-2-yl)-6-isobutyl-2,5-dioxopiperazin-1-yl]-N,N-dimethyl-2-(2-methyl-1-benzofuran-5-yl)ethanamide Carbonyldiimidazole (92 mg, 1.6 equiv.) was suspended in anhydrous dichloromethane (5 mL) and the suspension was left at room temperature for 15 minutes. (2RS)-2-(2-mrthyl-benzofuran-5-yl)-2-[(3R,6R)-3-(2,3-dihydro-1H-inden-2-yl)-6-isobutyl-2,5-dioxopiperazin-1-yl]-N-(2-hydroxyphenyl)ethanamide (200 mg) was then added and the mixture was stirred at room temperature for 5 hours. The resulting brown solution was then treated with a 2.0M solution of dimethylamine in tetrahydrofuran (1.06 mL, 6 equiv.) and the resulting mixture was stirred for 30 minutes and then left to stand at room temperature for 18 hours. The reaction mixture was diluted with dichloromethane (2 mL) and washed with 1M hydrochloric acid (2 mL). The organic phase was separated using a hydrophobic frit and was evaporated under reduced pressure to leave a brown gum. The crude product was applied to a silica cartridge (10 g). This was eluted with cyclohexane (100 ml), cyclohexane/ethyl acetate (100 ml of 2:1, 3:2, 1:1, 2:3 and 1:2 v/v), ethyl acetate (200 ml) and ethyl acetate/methanol (100 ml of 19:1 v/v). The required fractions were combined and evaporated in vacuo to give (2R)-2-[(3R,6R)-3-(2,3-dihydro-1H-inden-2-yl)-6-isobutyl-2,5-dioxopiperazin-1-yl]-N,N-dimethyl-2-(2-methyl-1-benzofuran-5-yl)ethanamide as an off-white solid (88 mg).

HPLC Rt=3.40 minutes; m/z [M+H]⁺=502.

¹H NMR (CDCl₃) δ 7.52 (d, 1H), 7.43 (d, 1H), 7.27-7.13 (m, 5H), 6.54 (s, 1H), 6.38 (m, 1H), 6.31 (d, 1H), 4.24 (m, 1H), 3.99 (dd, 1H), 3.22-3.05 (m, 3H), 2.99 (s, 3H), 2.86 (m, 1H), 2.82 (s, 3H), 2.75 (m, 1H), 2.48 (m, 3H), 1.45 (m, 1H), 1.36 (m, 1H), 0.57 (m, 1H), 0.51 (d, 3H), 0.19 (d, 3H).

Similarly prepared: —

EXAMPLE 142

(2R)-2-[(3R,6R)-3-(2,3-dihydro-1H-inden-2-yl)-6-isobutyl-2,5-dioxopiperazin-1-yl]-N-isopropyl-2-(2-methyl-1-benzofuran-5-yl)ethanamide HPLC Rt=3.40 minutes; m/z [M+H]⁺=516.
¹H NMR (CDCl₃) δ 7.57 (m, 1H), 7.41 (d, 1H), 7.28-7.11 (m, 5H), 6.61 (m, 1H), 6.37 (m, 1H), 5.49 (d, 1H), 5.23 (s, 1H), 4.11 (m, 1H), 4.02-3.93 (m, 2H), 3.19-3.05 (m, 3H), 2.92 (m, 1H), 2.77 (m, 1H), 2.48 (m, 3H), 1.79 (m, 1H), 1.70 (m, 1H), 1.38 (m, 1H), 1.10 (m, 6H), 0.78 (d, 3H), 0.69 (d, 3H).

EXAMPLE 143

(3R,6R)-3-(2,3-dihydro-1H-inden-2-yl)-6-isobutyl-1-[(1R)-1-(2-methyl-1-benzofuran-5-yl)-2-morpholin-4-yl-2-oxoethyl]piperazin-2,5-dione HPLC Rt=3.38 minutes; m/z [M+H]⁺=544.
¹H NMR (CDCl₃) δ 7.51 (d, 1H), 7.45 (d, 1H), 7.26-7.14 (m, 5H), 6.57 (s, 1H), 6.39 (m, 1H), 6.34 (m, 1H), 4.20 (m, 1H), 3.99 (m, 1H), 3.73-3.33 (6H), 3.22-3.03 (m, 5H), 2.88 (m, 1H), 2.75 (m, 1H), 2.49 (m, 3H), 1.45 (m, 1H), 1.37 (m, 1H), 0.54 (m, 1H), 0.51 (d, 3H), 0.20 (d, 3H).

EXAMPLE 144

(2R)-2-[(3R,6R)-3-(2,3-dihydro-1H-inden-2-yl)-6-isobutyl-2,5-dioxopiperazin-1-yl]-2-(2-fluoro-1-benzofuran-5-yl)-N,N-dimethylethanamide HPLC Rt=3.39 minutes; m/z [M+H]⁺=505.
¹H NMR (CDCl₃) δ 7.56 (d, 1H), 7.45 (d, 1H), 7.32 (dd, 1H), 7.23 (m, 2H), 7.16 (m, 2H), 6.55 (s, 1H), 6.23 (d, 1H), 5.89 (d, 1H), 4.22 (m, 1H), 3.99 (dd, 1H), 3.21-3.04 (m, 3H), 3.00 (s, 3H), 2.87 (m, 1H), 2.84 (s, 3H), 2.75 (m, 1H), 1.47 (m, 1H), 1.38 (m, 1H), 0.58-0.49 (m, 4H), 0.22 (d, 3H).

5-Bromo-2-fluoro-1-benzofuran

5-Bromobenzofuran-2-carboxylic acid (4.68 g) was suspended in carbon tetrachloride (150 ml) and water (50 ml). To this was added sodium bicarbonate (3.36 g), followed by Selectflor (7.1 g) and the reaction mixture was stirred rapidly for 20 hours. The reaction mixture was diluted with dichloromethane and 2N sodium hydroxide solution. The organic phase was separated, washed with brine and dried over anhydrous MgSO₄. The solvent was evaporated under reduced pressure at room temperature. The residue was applied to a silica cartridge (20 g) and eluted with diethyl ether. This gave 5-bromo-2-fluoro-1-benzofuran (1.4 g).

¹H NMR (CDCl₃) δ 7.61 (d, 1H), 7.36 (dd, 1H), 7.26 (d, 1H), 5.84 (dd, 1H).

2-Fluoro-5-formyl-1-benzofuran

A slurry of magnesium powder (219 mg) and iodine (cat) in dry tetrahydrofuran (3 ml) was heated at 50° C. under nitrogen for 20 minutes. 5-Bromo-2-fluoro-1-benzofuran (1.4 g) was dissolved in dry tetrahydrofuran (6 ml). A 1 ml portion of the solution was added to the slurry at 50° C. without stirring. After 30 minutes the rest of the solution was added slowly and the reaction was heated at reflux for 3 hours. The reaction was cooled in an ice/water bath and dimethylformamide (1 ml) was added dropwise maintaining the temperature below 10° C. After 1 hour a mixture of 2N hydrochloric acid (12.5 ml) and brine (12.5 ml) was added. The reaction mixture was extracted using ethyl acetate (3×25 ml). The combined organics were washed with brine and dried over anhydrous magnesium sulphate. The solvent was removed in vacuo and the residue applied to a silica cartridge (50 g). This was eluted with cyclohexane, cyclohexane/ethyl acetate (6:1, 5:1 v/v). This gave 2-fluoro-5-formyl-1-benzofuran (376 mg).

$^1$H NMR (CDCl$_3$) δ 10.05 (s, 1H), 8.04 (m, 1H), 7.83 (dd, 1H), 7.54 (d, 1H), 6.01 (dd, 1H).

EXAMPLE 145

(2R)-2-[(3R,6R)-3-(2,3-dihydro-1H-inden-2-yl)-6-isobutyl-2,5-dioxopiperazin-1-yl]-2-(2-fluoro-1-benzofuran-5-yl)-N-isopropylethanamide HPLC Rt=3.42 minutes; m/z [M+H]$^+$=520.
$^1$H NMR (CDCl$_3$) δ 7.61 (d, 1H), 7.42 (d, 1H), 7.31 (dd, 1H), 7.21 (m, 2H), 7.16 (m, 2H), 6.70 (d, 1H), 5.89 (d, 1H), 5.57 (d, 1H), 5.18 (s, 1H), 4.11 (m, 1H), 3.98 (m, 2H), 3.16 (m, 1H), 3.08 (m, 2H), 2.91 (m, 1H), 2.78 (m, 1H), 1.82 (m, 1H), 1.73 (m, 1H), 1.41 (m, 1H), 1.12 (d, 3H), 1.10 (d, 3H), 0.81 (d, 3H), 0.72 (d, 3H).

EXAMPLE 146

(3R,6R)-3-(2,3-dihydro-1H-inden-2-yl)-1-[(1R)-1-(2-fluoro-1-benzofuran-5-yl)-2-morpholin-4-yl-2-oxoethyl]-6-isobutylpiperazine-2,5-dione HPLC Rt=3.35 minutes; m/z [M+H]$^+$=548.
$^1$H NMR (CDCl$_3$) δ 7.55 (d, 1H), 7.47 (d, 1H), 7.31 (dd, 1H), 7.27-7.14 (m, 4H), 6.58 (s, 1H), 6.38 (d, 1H), 5.91 (d, 1H), 4.19 (m, 1H), 4.00 (dd, 1H), 3.73-3.50 (m, 5H), 3.39 (m, 1H), 3.23-3.04 (m, 5H), 2.87 (m, 1H), 2.76 (m, 1H), 1.47 (m, 1H), 1.40 (m, 1H), 0.53 (d, 3H), 0.51 (m, 1H), 0.24 (d, 3H).

EXAMPLE 147

(2R)-2-[(3R,6R)-3-(2,3-dihydro-1H-inden-2-yl)-6-isobutyl-2,5-dioxopiperazin-1-yl]-2-(1H-indol-6-yl)-N,N-dimethylethanamide HPLC Rt=3.38 minutes; m/z [M+H]$^+$=487.
$^1$H NMR (CDCl$_3$) δ 9.03 (s, 1H), 7.66 (d, 1H), 7.49 (d, 1H), 7.30 (m, 1H), 7.21 (m, 1H), 7.18-7.10 (m, 4H), 7.02 (m, 1H), 6.57 (s, 1H), 6.55 (m, 1H), 4.29 (m, 1H), 4.00 (dd, 1H), 3.22-3.03 (m, 3H), 3.00 (s, 3H), 2.92-2.73 (m, 5H), 1.40 (m, 1H), 1.33 (m, 1H), 0.57 (m, 1H), 0.45 (d, 3H), 0.06 (d, 3H).

EXAMPLE 148

(2R)-2-[(3R,6R)-3-(2,3-dihydro-1H-inden-2-yl)-6-isobutyl-2,5-dioxopiperazin-1-yl]-2-(1H-indol-6-yl)-N-methyl-N-[2-(methylsulphonyl)ethyl]ethanamide HPLC Rt=3.20 minutes; m/z [M+H]$^+$=579.
$^1$H NMR (CDCl$_3$) δ 9.62 (s, 1H), 7.64 (d, 1H), 7.41 (d, 1H), 7.30 (m, 1H), 7.26-7.10 (m, 6H), 6.51 (m, 1H), 6.48 (s, 1H), 4.18 (m, 1H), 4.05-3.90 (m, 2H), 3.68-3.50 (m, 2H), 3.28-3.01 (m, 4H), 2.96-2.69 (m, 8H), 1.41 (m, 2H), 0.65 (m, 1H), 0.47 (d, 3H), −0.10 (d, 3H).

EXAMPLE 149

(2R)-2-(1-benzothien-5-yl)-2-[(3R,6R)-3-(2,3-dihydro-1H-inden-2-yl)-6-isobutyl-2,5-dioxopiperazin-1-yl]-N,N-dimethylethanamide (2RS)-2-(1-benzothien-5-yl)-2-[(3R,6R)-3-(2,3-dihydro-1H-inden-2-yl)-6-isobutyl-2,5-dioxopiperazin-1-yl]-N-(2-benzyloxyphenyl)ethanamide A mixture of 5-formylbenzothiophene (2.0 g), (D)-leucine methyl ester hydrochloride (2.24 g), triethylamine (1.72 ml) and methanol (20 ml) was stirred at room temperature for 24 hours. N-tert-butoxycarbonyl-(D)-indanylglycine (3.59 g) and 2-benzyloxy-phenylisocyanide (2.58 g) were then added sequentially and the mixture stirred for 4 days. Then the solvent was removed under reduced pressure. The residue was taken up in dichloromethane (20 ml) and 4M hydrogen chloride in 1,4-dioxane (20 ml) and the mixture was stirred at room temperature for 2 hours. The solvent and hydrogen chloride were evaporated under reduced pressure. The crude material was dissolved in dichloromethane (30 ml) and triethylamine (10 ml) added. The mixture was stirred for 18 hours before the dichloromethane and excess of triethylamine were removed under reduced pressure. The crude product was dissolved in dichloromethane (100 ml) and washed with 1N hydrochloric acid (2×100 ml) and brine. The organic phase was dried over MgSO$_4$ and evaporated in vacuo to yield (2RS)-2-(1-benzothien-5-yl)-2-[(3R,6R)-3-(2,3-dihydro-1H-inden-2-yl)-6-isobutyl-2,5-dioxopiperazin-1-yl]-N-(2-benzyloxyphenyl)ethanamide as a brown foam (7.5 g).

HPLC Rt=3.88 minutes, m/z [M+H]$^+$=658.

(2RS)-2-(1-benzothien-5-yl)-2-[(3R,6R)-3-(2,3-dihydro-1H-inden-2-yl)-6-isobutyl-2,5-dioxopiperazin-1-yl]-N-(2-hydroxyphenyl)ethanamide (2RS)-2-(1-benzothien-5-yl)-2-[(3R,6R)-3-(2,3-dihydro-1H-inden-2-yl)-6-isobutyl-2,5-dioxopiperazin-1-yl]-N-(2-benzyloxyphenyl)ethanamide (1.0 g) was dissolved in dichloromethane (5 ml) and to this was added dropwise a 1.0M solution of BBr$_3$ in dichloromethane (2.0 ml). The reaction mixture was stirred at room temperature for 2 hours. To the reaction mixture was added 1N hydrochloric acid (30 ml) and dichloromethane (20 ml). The phases were separated and the organic phase was washed with 1N hydrochloric acid (30 ml) and brine (30 ml). The organic phase was dried over MgSO$_4$ and evaporated in vacuo. The residue was purified by Biotage™ flash column chromatography, eluting with 3:2 ethyl acetate:cyclohexane. The required fractions were combined and evaporated in vacuo to give (2RS)-2-(1-benzothien-5-yl)-2-[(3R,6R)-3-(2,3-dihydro-1H-inden-2-yl)-6-isobutyl-2,5-dioxopiperazin-1-yl]-N-(2-hydroxyphenyl)ethanamide (210 mg).

HPLC Rt=3.55 minutes, m/z [M+H]$^+$=568.

(2R)-2-(1-benzothien-5-yl)-2-[(3R,6R)-3-(2,3-dihydro-1H-inden-2-yl)-6-isobutyl-2,5-dioxopiperazin-1-yl]-N,N-dimethylethanamide Carbonyldiimidazole (100 mg) was suspended in anhydrous dichloromethane (1 mL) and the suspension was left at room temperature for 15 minutes. 2RS)-2-(1-benzothien-5-yl)-2-[(3R,6R)-3-(2,3-dihydro-1H-inden-2-yl)-6-isobutyl-2,5-dioxopiperazin-1-yl]-N-(2-hydroxyphenyl)ethanamide (200 mg) was then added and the mixture was stirred at room temperature for 5 hours 20 minutes. The resulting brown solution was then treated with a 2.0M solution of dimethylamine in tetrahydrofuran (1.0 mL, 6 equiv.) and the resulting mixture was stirred for 30 minutes and then left to stand at room temperature for 18 hours 15 minutes. The reaction mixture was evaporated under reduced pressure. The crude product was purified by silica column chromatography eluting with 1:1 v/v ethyl acetate:cyclohexane. The required fractions were combined and evaporated in vacuo to give (2R)-

2-(benzothien-5-yl)-2-[(3R,6R)-3-(2,3-dihydro-1H-inden-2-yl)-6-isobutyl-2,5-dioxopiperazin-1-yl]-N,N-dimethyl-ethanamide as a white solid (90 mg).

HPLC Rt=3.35 minutes, m/z [M+H]$^+$=504.

$^1$H NMR (CDCl$_3$) δ 7.94 (d, 1H), 7.89 (m, 1H), 7.70 (d, 1H), 7.54 (d, 1H), 7.41 (m, 1H), 7.35 (d, 1H), 7.23 (m, 1H), 7.13 (m, 3H), 6.63 (s, 1H), 4.25 (m, 1H), 4.02 (dd, 1H), 3.23-3.04 (m, 3H), 3.01 (s, 3H), 2.93-2.77 (m, 5H), 1.50-1.32 (m, 2H), 0.52 (m, 1H), 0.49 (d, 3H), 0.12 (d, 3H).

Compounds 150-169 and 174-175 were prepared via method 1. Compound 170 was prepared via method 2. Compounds 171, 172 and 173 were prepared via method 5.

| No. | Regno | MWt | Rt/min | MH+ | MH− | Name |
|-----|-------|-----|--------|-----|-----|------|
| 150 | 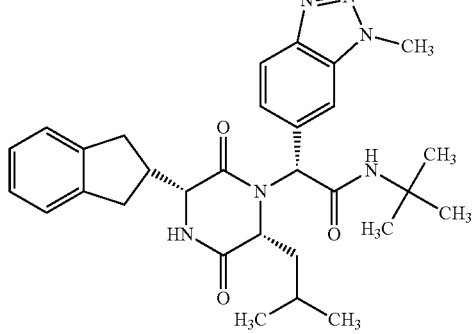 | 517.7 | 3.62 | 518 | 516 | (2R)-N-(tert-butyl)-2-(2,3-dihydro-1-benzofuran-5-yl)-2-[(3R,6R)-3-(2,3-dihydro-1H-inden-2-yl)-6-isobutyl-2,5-dioxopiperazin-1-yl]ethanamide |
| 151 | 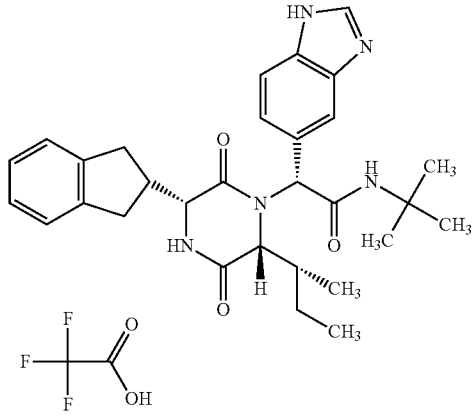 [SMILES: CC[C@@H](C)[C@@H]1C(=O)N[C@H](C2Cc3ccccc3C2)C(=O)N1[C@@H](C(=O)NC(C)(C)C)c1ccc2[nH]cnc2c1 ; O=C(O)C(F)(F)F] | 516.6 | 3.12 | 517 | 515 | 2-(1H-1,2,3-benzotriazol-5-yl)-N-(tert-butyl)-2-[(3R,6R)-3-(2,3-dihydro-1H-inden-2-yl)-6-isobutyl-2,5-dioxopiperazin-1-yl]acetamide |
| 152 | 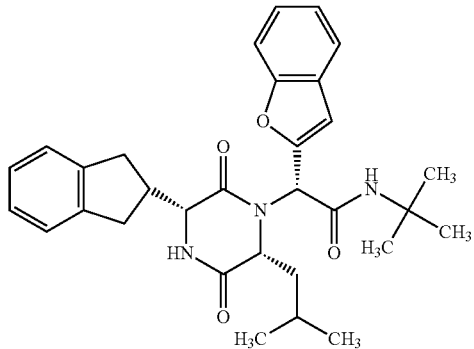 [SMILES: CC(C)C[C@@H]1C(=O)N[C@H](C2Cc3ccccc3C2)C(=O)N1[C@@H](C(=O)NC(C)(C)C)c1cc2ccccc2o1] | 533.7 | 3.42 | 534 | | (2R)-N-(tert-butyl)-2-(2,3-dihydro-1,4-benzodioxin-6-yl)-2-[(3R,6R)-3-(2,3-dihydro-1H-inden-2-yl)-6-isobutyl-2,5-dioxopiperazin-1-yl]ethanamide |

-continued

| No. | Regno | MWt | Rt/min | MH+ | MH− | Name |
|---|---|---|---|---|---|---|
| 153 | | 555.6 | 3.71 | 556 | 554 | (2R)-N-(tert-butyl)-2-(2,2-difluoro-1,3-benzodioxol-5-yl)-2-[(3R,6R)-3-(2,3-dihydro-1H-inden-2-yl)-6-isobutyl-2,5-dioxopiperazin-1-yl]ethanamide |
| 154 | | 532.7 | 3.32 | 533 | 531 | (2R)-2-(1,3-benzothiazol-6-yl)-N-(tert-butyl)-2-[(3R,6R)-3-(2,3-dihydro-1H-inden-2-yl)-6-isobutyl-2,5-dioxopiperazin-1-yl]ethanamide |
| 155 | | 530.7 | 3.18 | 531 | 529 | (2R)-N-(tert-butyl)-2-[(3R,6R)-3-(2,3-dihydro-1H-inden-2-yl)-6-isobutyl-2,5-dioxopiperazin-1-yl]-2-(1-methyl-1H-1,2,3-benzotriazol-5-yl)ethanamide |
| 156 | | 530.7 | 3.22 | 531 | 529 | (2R)-N-(tert-butyl)-2-[(3R,6R)-3-(2,3-dihydro-1H-inden-2-yl)-6-isobutyl-2,5-dioxopiperazin-1-yl]-2-(1-methyl-1H-1,2,3-benzotriazol-6-yl)ethanamide |

| No. | Regno | MWt | Rt/min | MH+ | MH− | Name |
|---|---|---|---|---|---|---|
| 157 | | 629.7 | 3.06 | | 514 | (2R)-2-(1H-benzimidazol-5-yl)-N-(tert-butyl)-2-{(3R,6R)-3-(2,3-dihydro-1H-inden-2-yl)-6-[(1R)-1-methylpropyl]-2,5-dioxopiperazin-1-yl}ethanamide trifluoroacetate |
| 158 | | 515.7 | 3.72 | 516 | 514 | (2R)-2-(1-benzofuran-2-yl)-N-(tert-butyl)-2-[(3R,6R)-3-(2,3-dihydro-1H-inden-2-yl)-6-isobutyl-2,5-dioxopiperazin-1-yl]ethanamide |
| 159 | | 530.7 | 3.3 | 531 | 529 | (2R)-N-(tert-butyl)-2-[(3R,6R)-3-(2,3-dihydro-1H-inden-2-yl)-6-isobutyl-2,5-dioxopiperazin-1-yl]-2-(2-methyl-1,3-benzoxazol-5-yl)ethanamide |
| 160 | | 530.7 | 3.35 | 531 | 529 | (2R)-N-(tert-butyl)-2-[(3R,6R)-3-(2,3-dihydro-1H-inden-2-yl)-6-isobutyl-2,5-dioxopiperazin-1-yl]-2-(2-methyl-1,3-benzoxazol-6-yl)ethanamide |

-continued

| No. | Regno | MWt | Rt/min | MH+ | MH− | Name |
| --- | --- | --- | --- | --- | --- | --- |
| 161 | | 519.7 | 3.37 | 520 | 518 | (2R)-2-(1,2,3-benzothiadiazol-6-yl)-2-[(3R,6R)-3-(2,3-dihydro-1H-inden-2-yl)-6-isobutyl-2,5-dioxopiperazin-1-yl]-N-isopropylethanamide |
| 162 | | 514.7 | 3.41 | 515 | | (2R)-2-[(3R,6R)-3-(2,3-dihydro-1H-inden-2-yl)-6-isobutyl-2,5-dioxopiperazin-1-yl]-N-isopropyl-2-(1-methyl-1H-indol-5-yl)ethanamide |
| 163 | | 529.6 | | | | (2R)-2-[(3R,6R)-3-(2,3-dihydro-1H-inden-2-yl)-6-isobutyl-2,5-dioxopiperazin-1-yl]-N-isopropyl-2-(2-oxo-2H-chromen-6-yl)ethanamide |
| 164 | | 517.7 | 3.53 | 518 | 516 | (2R)-2-(1-benzothien-5-yl)-2-[(3R,6R)-3-(2,3-dihydro-1H-inden-2-yl)-6-isobutyl-2,5-dioxopiperazin-1-yl]-N-isopropylethanamide |

-continued

| No. | Regno | MWt | Rt/min | MH+ | MH− | Name |
|---|---|---|---|---|---|---|
| 165 | | 501.6 | 3.42 | 502 | 500 | (2R)-2-(1-benzofuran-6-yl)-2-[(3R,6R)-3-(2,3-dihydro-1H-inden-2-yl)-6-isobutyl-2,5-dioxopiperazin-1-yl]-N-isopropylethanamide |
| 166 | | 500.6 | 3.35 | 501 | 499 | (2R)-2-[(3R,6R)-3-(2,3-dihydro-1H-inden-2-yl)-6-isobutyl-2,5-dioxopiperazin-1-yl]-2-(1H-indol-6-yl)-N-isopropylethanamide |
| 167 | | 515.7 | 4.88 | 516 | 514 | 2R-[(3R,6R)-3-(2,3-dihydro-1H-inden-2-yl)-6-isobutyl-2,5-dioxopiperazin-1-yl]-N-isopropyl-2-(1-methyl-1H-benzimidazol-2-yl)acetamide |
| 168 | | 515.7 | 4.32 | 516 | 514 | (2R)-2-[(3R,6R)-3-(2,3-dihydro-1H-inden-2-yl)-6-isobutyl-2,5-dioxopiperazin-1-yl]-N-isopropyl-2-(1-methyl-1H-benzimidazol-6-yl)ethanamide |

-continued

| No. | Regno | MWt | Rt/min | MH+ | MH− | Name |
|---|---|---|---|---|---|---|
| 169 | 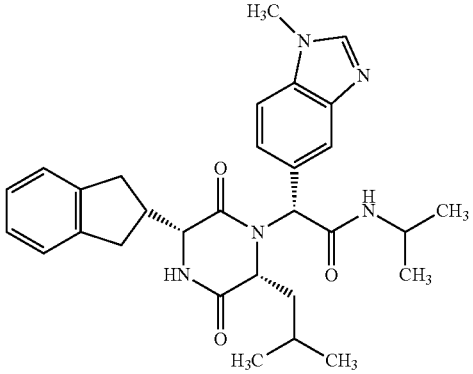 [SMILES: CC(C)C[C@@H]1C(=O)N[C@H](C2Cc3ccccc3C2)C(=O)N1[C@@H](C(=O)NC(C)C)c1ccc2c(c1)ncn2C] | 515.7 | 2.65 | 516 | 514 | (2R)-2-[(3R,6R)-3-(2,3-dihydro-1H-inden-2-yl)-6-isobutyl-2,5-dioxopiperazin-1-yl]-N-isopropyl-2-(1-methyl-1H-benzimidazol-5-yl)ethanamide |
| 170 | 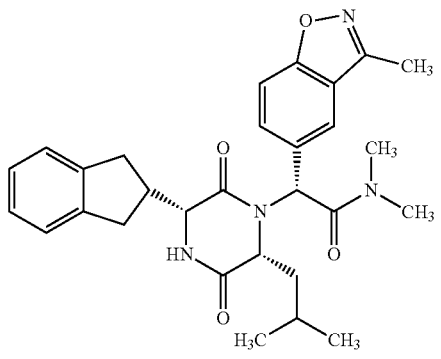 [SMILES: Cc1noc2ccc([C@H](C(=O)N(C)C)N3C(=O)[C@@H](C4Cc5ccccc5C4)NC(=O)[C@H]3CC(C)C)cc12] | 502.6 | 3.35 | 503 | 501 | (2R)-2-[(3R,6R)-3-(2,3-dihydro-1H-inden-2-yl)-6-isobutyl-2,5-dioxopiperazin-1-yl]-N,N-dimethyl-2-(3-methyl-1,2-benzisoxazol-5-yl)ethanamide |
| 171 | 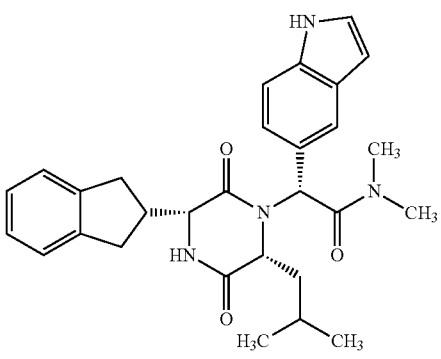 [SMILES: CC(C)C[C@@H]1C(=O)N[C@H](C2Cc3ccccc3C2)C(=O)N1[C@@H](C(=O)N(C)C)c1ccc2[nH]ccc2c1] | 486.6 | 3.07 | 487 | 485 | (2R)-2-[(3R,6R)-3-(2,3-dihydro-1H-inden-2-yl)-6-isobutyl-2,5-dioxopiperazin-1-yl]-2-(1H-indol-5-yl)-N,N-dimethylethanamide |
| 172 | 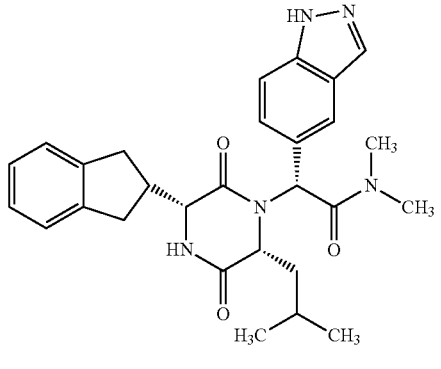 [SMILES: CC(C)C[C@@H]1C(=O)N[C@H](C2Cc3ccccc3C2)C(=O)N1[C@@H](C(=O)N(C)C)c1ccc2[nH]ncc2c1] | 487.6 | 2.94 | 488 |  | (2R)-2-[(3R,6R)-3-(2,3-dihydro-1H-inden-2-yl)-6-isobutyl-2,5-dioxopiperazin-1-yl]-2-(1H-indazol-5-yl)-N,N-dimethylethanamide |

-continued

| No. | Regno | MWt | Rt/min | MH+ | MH− | Name |
|---|---|---|---|---|---|---|
| 173 | | 487.6 | 2.99 | 488 | 486 | (2R)-2-[(3R,6R)-3-(2,3-dihydro-1H-inden-2-yl)-6-isobutyl-2,5-dioxopiperazin-1-yl]-2-(1H-indazol-6-yl)-N,N-dimethylethanamide |
| 174 | | 511.7 | 3.56 | 512 | | (2R,S)-[(3R,6R)-3-(2,3-dihydro-1H-inden-2-yl)-6-isobutyl-2,5-dioxopiperazin-1-yl]-N-isopropyl-2-(2-naphthyl)acetamide |
| 175 | | 512.7 | 3.19 | 513 | | (2R,S)-[(3R,6R)-3-(2,3-dihydro-1H-inden-2-yl)-6-isobutyl-2,5-dioxopiperazin-1-yl]-N-isopropyl-2-quinolin-6-ylacetamide |

EXAMPLE 176

(2R)-2-[(3R,6R)-3-(2,3-dihydro-1H-inden-2-yl)-6-isobutyl-2,5-dioxopiperazin-1-yl]-N-isopropyl-2-[5-(trifluoromethyl)-2-furyl]ethanamide To a solution of 5-trifluoromethyl-furan-2-carbaldehyde (140 mg)[prepared as in ref. Chem. Heterocycl. Compd. 13, 1977, 1280-1282 by R. V. Grigorash, V. V. Lyalin, L. A. Alekseeva and L. M. Yagupol'skii: 5-Trifluoromethylfuran Derivatives] in methanol (1.1 ml) was added triethylamine (118 µl) and (D)-leucine t-butyl ester hydrochloride (190 mg). The mixture was left to stand for 16.33 hours before (2R)-[(tert-butoxycarbonyl)amino](2,3-dihydro-1H-inden-2-yl)ethanoic acid (246 mg) and isopropylisocyanide (77.4 µl) were sequentially added. The mixture, a yellow solution, was left to stand for 24 hours before the solvent was removed in vacuo. The residue was dissolved in 4M hydrogen chloride in dioxane (3 ml) and left to stand for 6.75 hours at ambient temperature. After this time, the solvent was removed in vacuo. The residue was dissolved in methanol (4 ml) and treated with a solution of 4M hydrogen chloride in dioxane (0.2 ml) and was left to stand overnight. After this time, the solvent was removed in vacuo. The residue was stirred in dioxane (9.5 ml) containing triethylamine (0.5 ml) and dichloromethane (5 ml) for 4.75 hours. Then the mixture was evaporated in vacuo to leave a light brown solid. This crude material was purified by SPE column (10 g, silica Mega Bond Elut™) eluting stepwise with 100% chloroform, 4:1 cyclohexane:diethyl ether, 3:1 cyclohexane:diethyl ether, 2:1 cyclohexane:diethyl ether, 1:1 cyclohexane:diethyl ether, 1:2 cyclohexane:diethyl ether, 1:3 cyclohexane:diethyl ether, 100% diethyl ether, 1:1 ethyl acetate:cyclohexane, 2:1 ethyl acetate:cyclohexane, 3:1 ethyl acetate:cyclohexane, 100% ethyl acetate. The 1:2 cyclohexane:diethyl ether to 2:1 ethyl acetate:cyclohexane fractions inclusive were combined to give an orange gum (215 mg). The gum was purified further, to separate the isomers, by preparative plate chromatography. Whatman PK6F silicagel 60 plates 20×20 cm², eluted in 1:1 ethyl acetate:cyclohexane six times and extracted with 9:1 ethyl acetate:methanol to give (2R)-2-[(3R,6R)-3-(2,3-dihydro-1H-inden-2-yl)-6-isobutyl-2,5-dioxopiperazin-1-yl]-N-isopropyl-2-[5-(trifluoromethyl)-2-furyl]ethanamide (64 mg), HPLC Rt=3.59 minutes; m/z [M+H]$^+$=520.

$^1$H NMR (CDCl$_3$) δ 7.88 (d, 1H), 7.16 (m, 4H), 6.85 (d, 1H), 6.74 (d, 1H), 6.30 (d, 1H), 5.73 (s, H), 4.19 (dd, 1H), 4.08 (m, 1H), 3.97 (dd, 1H), 3.14 (m, 2H), 3.01 (m, 1H), 2.84 (m, 2H), 1.81 (m, 1H), 1.68 (m, 1H), 1.15 (d, 6H), 1.11 (m, 1H), 0.82 (dd, 6H).

Similarly prepared

EXAMPLE 177

(2S)-2-[(3R,6R)-3-(2,3-dihydro-1H-inden-2-yl)-6-isobutyl-2,5-dioxopiperazin-1-yl]-N-isopropyl-2-(5-methylthien-2-yl)ethanamide By the procedure of Example 176 but using 5-methylthiophene-2-carbaldehyde HPLC Rt=3.46 minutes; m/z [M+H]$^+$=482.

$^1$H NMR (CDCl$_3$) δ 7.21 (m, 2H), 7.16 (m, 2H), 6.94 (d, 1H), 6.67 (d, 1H), 6.63 (d, 1H), 5.73 (d, 1H), 4.94 (s, 1H), 4.07 (m, 1H), 3.93 (m, 2H), 3.16 (dd, 1H), 3.05 (m, 2H), 2.93 (m, 1H), 2.77 (m, 1H), 2.47 (s, 3H), 1.96 (m, 1H), 1.86 (m, 1H), 1.72 (m, 1H), 1.17 (d, 3H), 1.12 (d, 3H), 0.94 (d, 3H), 0.92 (d, 3H)

EXAMPLE 178

(2R)-2-[(3R,6R)-3-(2,3-dihydro-1H-inden-2-yl)-6-isobutyl-2,5-dioxopiperazin-1-yl]-N,N-dimethyl-2-[5-(trifluoromethyl)-2-furyl]ethanamide

N-[2-(benzyloxy)phenyl]-2-[(3R,6R)-3-(2,3-dihydro-1H-inden-2-yl)-6-isobutyl-2,5-dioxopiperazin-1-yl]-2-[5-(trifluoromethyl)-2-furyl]acetamide A mixture of 5-trifluoromethyl-furan-2-carbaldehyde (351 mg), (D)-leucine methyl ester hydrochloride (389 mg), triethylamine (0.298 ml) and methanol (2.2 ml) was stirred at room temperature for 4 hours and then left to stand for 19 hours. N-tert-butoxycarbonyl-(D)-indanylglycine (623 mg) and 2-benzyloxy-phenylisocyanide (448 mg) were then added sequentially and the mixture stirred for 7 hours before being left to stand at room temperature for 41 hours. Then the solvent was removed under reduced pressure to leave an orange/brown syrup. This was taken up in 4M hydrogen chloride in 1,4-dioxane (2.8 ml) and the mixture was stirred at room temperature for 2 hours. The solvent and hydrogen chloride were evaporated under reduced pressure. The crude material was dissolved in methanol (5 ml) and triethylamine (0.54 ml) added. The mixture was stirred for 18 hours before the methanol and excess of triethylamine were removed under reduced pressure. The crude product was purified by Biotage™ flash column chromatography (40 g silica cartridge eluted with 1:5 ethyl acetate:cyclohexane (600 ml), 1:3 ethyl acetate:cyclohexane (400 ml) and 1:2 ethyl acetate:cyclohexane (450 ml)) to yield N-[2-(benzyloxy)phenyl]-2-[(3R,6R)-3-(2,3-dihydro-1H-inden-2-yl)-6-isobutyl-2,5-dioxopiperazin-1-yl]-2-[5-(trifluoromethyl)-2-furyl]acetamide as an orange solid (472 mg).

HPLC Rt=4.04 minutes, m/z [M+H]$^+$=660.

2-[(3R,6R)-3-(2,3-dihydro-1H-inden-2-yl)-6-isobutyl-2,5-dioxopiperazin-1-yl]-N-(2-hydroxyphenyl)-2-[5-(trifluoromethyl)-2-furyl]acetamide N-[2-(benzyloxy)phenyl]-2-[(3R,6R)-3-(2,3-dihydro-1H-inden-2-yl)-6-isobutyl-2,5-dioxopiperazin-1-yl]-2-[5-(trifluoromethyl)-2-furyl]acetamide (469 mg) was dissolved in ethyl acetate (10 ml) and hydrogenated at atmospheric pressure over 10% palladium on activated carbon (100 mg). After 4 hours the catalyst was removed by filtration through glass fibre filters and washed with ethyl acetate. The filtrate and washings were combined, evaporated under reduced pressure and dried in vacuo at room temperature to leave a yellow/brown solid (400 mg). The solid was dried over P$_2$O$_5$ overnight to give 2-[(3R,6R)-3-(2,3-dihydro-1H-inden-2-yl)-6-isobutyl-2,5-dioxopiperazin-1-yl]-N-(2-hydroxyphenyl)-2-[5-(trifluoromethyl)-2-furyl]acetamide (365 mg).

HPLC Rt=3.64 minutes, m/z [M+H]$^+$=570.

(2R)-2-[(3R,6R)-3-(2,3-dihydro-1H-inden-2-yl)-6-isobutyl-2,5-dioxopiperazin-1-yl]-N,N-dimethyl-2-[5-(trifluoromethyl)-2-furyl]ethanamide Carbonyldiimidazole (78 mg, 1.6 equiv.) was suspended in anhydrous dichloromethane (1 mL) and the suspension was left at room temperature for 15 minutes. (R)—N-(2-Hydroxy-phenyl)-2-((3R,6R)-3-indan-2-yl-6-isobutyl-2,5-dioxo-piperazin-1-yl)-2-(5-trifluoromethyl-furan-2-yl)-acetamide (172 mg) was then added and the mixture was stirred at room temperature for 5 hours 20 minutes. The resulting brown solution was then treated with a 2.0M solution of dimethylamine in tetrahydrofuran (0.9 mL, 6 equiv.) and the resulting mixture was stirred for 30 minutes and then left to stand at room temperature for 18 hours 15 minutes. The reaction mixture was diluted with dichloromethane (2 mL) and washed with 1M hydrochloric acid (2 mL). The organic phase was separated using a hydrophobic frit and was evaporated under reduced pressure to leave a brown gum. The crude product was applied to 3 preparative chromatography plates, which were eluted with 1:1 v/v ethyl acetate:cyclohexane. The required band was extracted with ethyl acetate to give the (2R)-2-[(3R,6R)-3-(2,3-dihydro-1H-inden-2-yl)-6-isobutyl-2,5-dioxopiperazin-1-yl]-N,N-dimethyl-2-[5-(trifluoromethyl)-2-furyl]ethanamide as a pale yellow solid (87 mg).

HPLC Rt=3.51 minutes, m/z [M+H]$^+$=506.

$^1$H NMR (CDCl$_3$) δ 7.19 (m, 5H), 6.86 (dd, 1H), 6.64 (d, 1H), 6.61 (s, 1H), 4.25 (m, 1H), 3.97 (dd, 1H), 3.20-3.02 (m, 3H), 3.01 (s, 3H), 2.96 (s, 3H), 2.88 (m, 1H), 2.80 (m, 1H), 1.70 (m, 1H), 1.67 (m, 1H), 0.74 (d, 3H), 0.70 (m, 1H), 0.63 (d, 3H).

EXAMPLE 179

(2R)-2-[(3R,6R)-3-(2,3-dihydro-1H-inden-2-yl)-6-isobutyl-2,5-dioxopiperazin-1-yl]-N,N-dimethyl-2-(2-methyl-1,3-oxazol-4-yl)ethanamide By the procedure of Example 178, using (2R)-2-[(3R,6R)-3-(2,3-dihydro-1H-inden-2-yl)-6-isobutyl-2,5-dioxopiperazin-1-yl]-N-(2-hydroxyphenyl)-2-(2-methyl-1,3-oxazol-4-yl)ethanamide HPLC: Rt=2.88 minutes; m/z (M+H)$^+$=453

(2R)-2-[(3R,6R)-3-(2,3-dihydro-1H-inden-2-yl)-6-isobutyl-2,5-dioxopiperazin-1-yl]-N-(2-hydroxyphenyl)-2-(2-methyl-1,3-oxazol-4-yl)ethanamide A mixture of 2-methyl-oxazole-4-carbaldehyde[1] (340 mg), (D)-leucine methyl ester hydrochloride (568 mg), triethylamine (0.435 ml) and anhydrous methanol (20 ml) was stirred at room temperature for 18 hours. N-benzyloxycarbonyl-(D)-indanylglycine (1.015 g) and 2-benzyloxy-phenyl-isocyanide (648 mg) were then added sequentially and the mixture stirred for 12 days before being left to stand at room temperature for 10 days. The solvent was removed under reduced pressure to leave a dark orange gum which was dissolved in ethyl acetate (150 mL) and washed with 2M hydrochloric acid (100 mL), saturated sodium bicarbonate solution (100 mL) and saturated sodium chloride solution (50 mL) then dried over anhydrous magnesium sulphate and concentrated under reduced pressure to a volume of 5 mL. This crude solution was diluted with ethanol (80 mL) containing acetic acid (1.6 mL) and added under vacuum to 10% palladium on carbon (50% water, 425 mg). The resulting suspension was stirred under an atmosphere of hydrogen for 20 hours, filtered (celite filteraid) washed with ethanol (50 mL) and the filtrate added under vacuum to a second quantity of 10% palladium on carbon (50% water, 670 mg). The suspension was stirred under an atmosphere of hydrogen for 2 hours, the hydrogenation apparatus was then evacuated and refilled with hydrogen and the suspension stirred for a further 20 hours. The suspension was filtered (celite filteraid) washed with ethanol (200 mL) and the combined filtrates concentrated under reduced pressure. The residue was partitioned between saturated sodium bicarbonate solution (100 mL) and dichloromethane (60 mL), then the organic layer dried (hydrophobic frit) and the solvent removed under reduced pressure. Purification by Biotage flash chromatography (40 g silica) eluting with ethyl acetate:cyclohexane (3:1, 300 mL) ethyl acetate (300 mL) then ethyl acetate:methanol (20:1, 600 mL) gave (2R)-2-[(3R,6R)-3-(2,3-dihydro-1H-inden-2-yl)-6-isobutyl-2,5-dioxopiperazin-1-yl]-N-(2-hydroxyphenyl)-2-(2-methyl-1,3-oxazol-4-yl)ethanamide as a brown foam (197 mg).

HPLC: Rt=3.28 minutes; m/z (M+H)$^+$=517
Ref (1) CAS113732-84-6

EXAMPLE 180

(3R,6R)-3-(2,3-dihydro-1H-inden-2-yl)-6-isobutyl-1-[(1R)-1-(2-methyl-1,3-oxazol-4-yl)-2-morpholin-4-yl-2-oxoethyl]piperazine-2,5-dione By the procedure of Example 179, using morpholine
HPLC: Rt=2.89 minutes; m/z (M+H)$^+$=495

EXAMPLE 181

(2S)-2-[(3R,6R)-3-(2,3-dihydro-1H-inden-2-yl)-6-isobutyl-2,5-dioxopiperazin-1-yl]-N,N-dimethyl-2-(5-methylthien-2-yl)ethanamide By the procedure of Example 180, using 5-methyl-thiophene-2-carbaldehyde
HPLC Rt=3.25 minutes; m/z M$^+$=468.

EXAMPLE 182

(2S)-2-[(3R,6R)-3-(2,3-dihydro-1H-inden-2-yl)-6-isobutyl-2,5-dioxopiperazin-1-yl]-2-(3-fluoro-5-methylthien-2-yl)-N,N-dimethylethanamide By the procedure of Example 178, using 3-fluoro-5-methyl-thiophene-2-carbaldehyde
HPLC: Rt=3.20 minutes; m/z M$^+$=486

2-(3-Bromo-5-methyl-thiophen-2-yl)-[1,3]dioxane

3-Bromo-5-methyl-2-thiophenecarbaldehyde (1.00 g) was dissolved in dry 1,4-dioxane (8 ml). Molecular sieves (4 Angstrom, 2 g), 1,3-propandiol (9 ml), p-toluene sulphonic acid (362 mg) were added and the mixture was stirred under a nitrogen atmosphere, at room temperature, over night. Molecular sieves were removed by filtration and the filtrate evaporated. The residue was taken up with ethyl acetate and washed with saturated solution of sodium carbonate. The aqueous was extracted with more ethyl acetate and the combined layers washed with brine, dried over magnesium sulphate, filtrated and concentrated to a yellow oil (1 g).

Purification was performed by filtration on a SPE cartridge (Silica-10 g) using dichloromethane as eluent. The solution was eventually concentrated to yield 2-(3-bromo-5-methyl-thiophen-2-yl)-[1,3]dioxane as a yellow solid (1.18 g).

$^1$H-NMR (CDCl$_3$, 400 MHz): 6.60 ppm (s, 1H); 5.72 ppm (s, 1H); 4.23 ppm (m, 2H); 3.98 ppm (m, 2H); 2.44 ppm (d, 3H); 2.22 ppm (m, 1H); 1.42 ppm (m, 1H).

3-Fluoro-5-methyl-thiophene-2-carbaldehyde

To a solution of 2-(3-bromo-5-methyl-thiophen-2-yl)-[1,3]dioxane (1.16 g) in dry tetrahydrofuran (10 ml), under a nitrogen atmosphere, at −78° C., 1.6M n-butyl lithium in hexane (3.30 ml) was added dropwise. After 15 minutes stirring, N-fluoro-benzene-sulfonyl-imide (1.66 g) was added portionwise. The solution was stirred at −78° C. for further 10 minutes, allowed to warm to room temperature and then stirred for a further 60 minutes. The reaction was quenched with water (5 ml), diluted with diethyl ether (20 ml) and washed with 1N sodium hydroxide (30 ml). The aqueous was extracted with diethyl ether again (2×10 ml), the combined organic layers were dried over magnesium sulphate, filtrated and evaporated. The residue was redissolved in 1,4-dioxane (15 ml) and water (10), p-toluene sulphonic acid (837 mg) was added and the solution was stirrer at room temperature, over night. Neutralised with a saturated solution of sodium bicarbonate (10 ml), then extracted with ether twice. The organic was dried over magnesium sulphate and evaporated at reduced pressure (200 mbar). The residual dioxane was removed by distillation at reduced pressure, the residue further purified by flash chromatography (petroleum ether/dichloromethane 55/45), giving 3-fluoro-5-methyl-thiophene-2-carbaldehyde as a colourless oil (366 mg), approximately 70% pure.

$^1$H-NMR (CDCl$_3$, 400 MHz): δ 9.93 ppm (s, 1H); 6.62 ppm (s, 1H); 2.52 ppm (m, 3H).

Similarly prepared:

Compounds 183-206, 213, 215, 218, 222-225 were prepared via method 1. Compounds 207, 208, 216, were prepared via method 2. Compounds 209-212, 214, 217, 219-221 and 226 were prepared via method 5.

| Eg No. | Structure | MWt | Rt/ min | +ve ion | −ve ion | name |
|---|---|---|---|---|---|---|
| 183 | 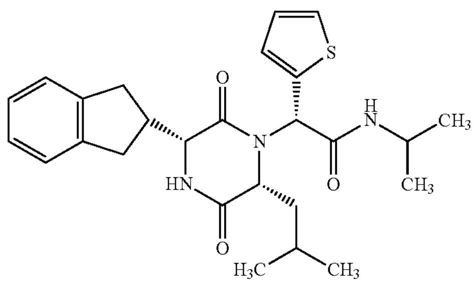 [SMILES: CC(C)C[C@@H]1C(=O)N[C@H](C2Cc3ccccc3C2)C(=O)N1[C@@H](C(=O)NC(C)C)c1cccs1] | 467.7 | 3.4 | 468 | 466 | (2S)-2-[(3R,6R)-3-(2,3-dihydro-1H-inden-2-yl)-6-isobutyl-2,5-dioxopiperazin-1-yl]-N-isopropyl-2-thien-2-ylethanamide |
| 184 | 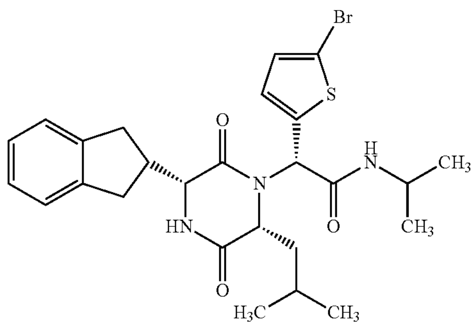 [SMILES: CC(C)C[C@@H]1C(=O)N[C@H](C2Cc3ccccc3C2)C(=O)N1[C@@H](C(=O)NC(C)C)c1ccc(Br)s1] | 546.6 | 3.6 | 546/548 | 546/544 | (2S)-2-(5-bromothien-2-yl)-2-[(3R,6R)-3-(2,3-dihydro-1H-inden-2-yl)-6-isobutyl-2,5-dioxopiperazin-1-yl]-N-isopropylethanamide |
| 185 | 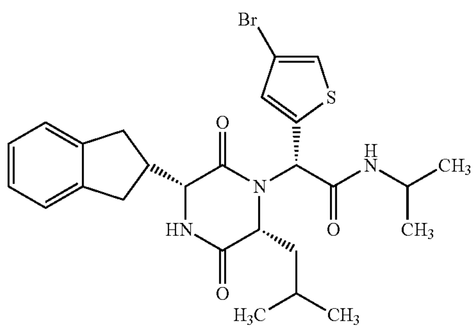 [SMILES: CC(C)C[C@@H]1C(=O)N[C@H](C2Cc3ccccc3C2)C(=O)N1[C@@H](C(=O)NC(C)C)c1cc(Br)cs1] | 546.6 | 3.6 | 546/548 | 544/546 | (2S)-2-(4-bromothien-2-yl)-2-[(3R,6R)-3-(2,3-dihydro-1H-inden-2-yl)-6-isobutyl-2,5-dioxopiperazin-1-yl]-N-isopropylethanamide |
| 186 | 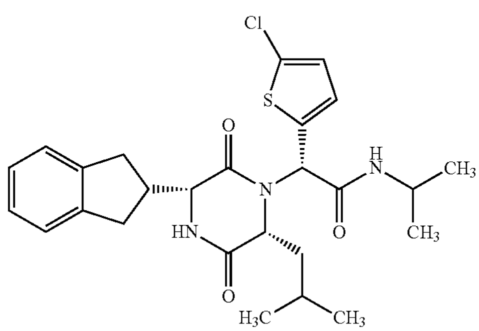 [SMILES: CC(C)C[C@@H]1C(=O)N[C@H](C2Cc3ccccc3C2)C(=O)N1[C@@H](C(=O)NC(C)C)c1ccc(Cl)s1] | 502.1 | 3.6 | 501-3 | 499-501 | (2S)-2-(5-chlorothien-2-yl)-2-[(3R,6R)-3-(2,3-dihydro-1H-inden-2-yl)-6-isobutyl-2,5-dioxopiperazin-1-yl]-N-isopropylethanamide |
| 187 | 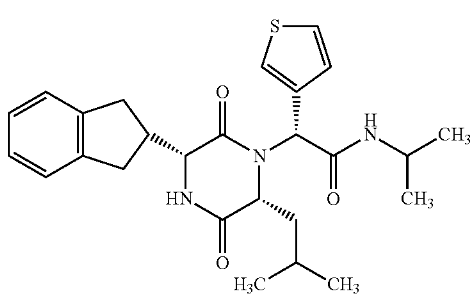 [SMILES: CC(C)C[C@@H]1C(=O)N[C@H](C2Cc3ccccc3C2)C(=O)N1[C@@H](C(=O)NC(C)C)c1ccsc1] | 467.7 | 3.3 | 468 | 466 | (2R)-2-[(3R,6R)-3-(2,3-dihydro-1H-inden-2-yl)-6-isobutyl-2,5-dioxopiperazin-1-yl]-N-isopropyl-2-thien-3-ylethanamide |

| Eg No. | Structure | MWt | Rt/min | +ve ion | −ve ion | name |
|---|---|---|---|---|---|---|
| 188 | 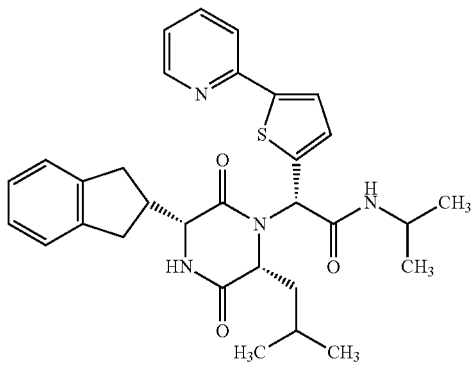 [SMILES: CC(C)C[C@@H]1C(=O)N[C@H](C2Cc3ccccc3C2)C(=O)N1[C@@H](C(=O)NC(C)C)c1ccc(-c2ccccn2)s1] | 544.8 | 3.4 | 545 | 543 | (2S)-2-[(3R,6R)-3-(2,3-dihydro-1H-inden-2-yl)-6-isobutyl-2,5-dioxopiperazin-1-yl]-N-isopropyl-2-(5-pyridin-2-ylthien-2-yl)ethanamide |
| 189 | 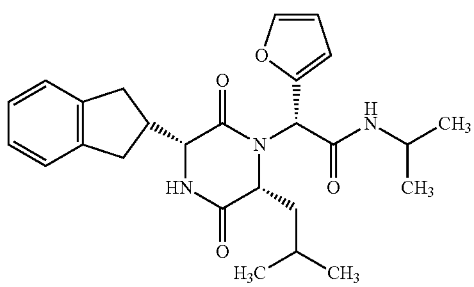 [SMILES: CC(C)C[C@@H]1C(=O)N[C@H](C2Cc3ccccc3C2)C(=O)N1[C@@H](C(=O)NC(C)C)c1ccco1] | 451.6 | 3.3 | 452 | 450 | (2R)-2-[(3R,6R)-3-(2,3-dihydro-1H-inden-2-yl)-6-isobutyl-2,5-dioxopiperazin-1-yl]-2-(2-furyl)-N-isopropylethanamide |
| 190 | 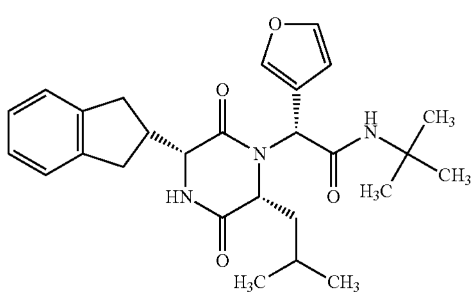 [SMILES: CC(C)C[C@@H]1C(=O)N[C@H](C2Cc3ccccc3C2)C(=O)N1[C@@H](C(=O)NC(C)(C)C)c1ccoc1] | 465.7 | 3.4 | 466 | 464 | (2R)-N-(tert-butyl)-2-[(3R,6R)-3-(2,3-dihydro-1H-inden-2-yl)-6-isobutyl-2,5-dioxopiperazin-1-yl]-2-(3-furyl)ethanamide |
| 200 | 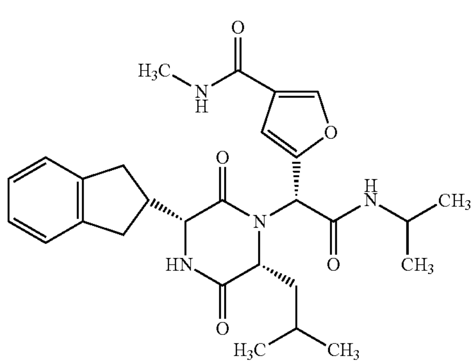 [SMILES: CNC(=O)c1coc([C@H](C(=O)NC(C)C)N2C(=O)[C@@H](C3Cc4ccccc4C3)NC(=O)[C@H]2CC(C)C)c1] | 508.7 | 2.9 | 509 | 507 | 5-[1-[(3R,6R)-3-(2,3-dihydro-1H-inden-2-yl)-6-isobutyl-2,5-dioxopiperazin-1-yl]-2-(isopropylamino)-2-oxoethyl]-N-methyl-3-furamide |

-continued

| Eg No. | Structure | MWt | Rt/ min | +ve ion | −ve ion | name |
|---|---|---|---|---|---|---|
| 201 | 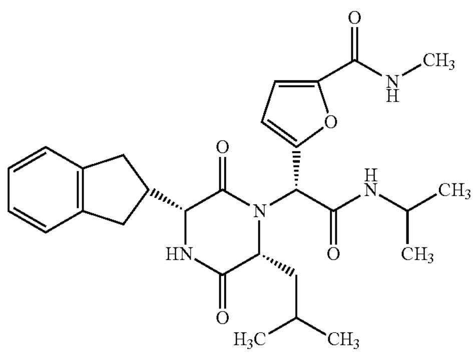 [SMILES: CNC(=O)c1ccc([C@H](C(=O)NC(C)C)N2C(=O)[C@@H](C3Cc4ccccc4C3)NC(=O)[C@H]2CC(C)C)o1] | 508.7 | 3 | 509 | 507 | 5-[(1R)-1-[(3R,6R)-3-(2,3-dihydro-1H-inden-2-yl)-6-isobutyl-2,5-dioxopiperazin-1-yl]-2-(isopropylamino)-2-oxoethyl]-N-methyl-2-furamide |
| 202 | 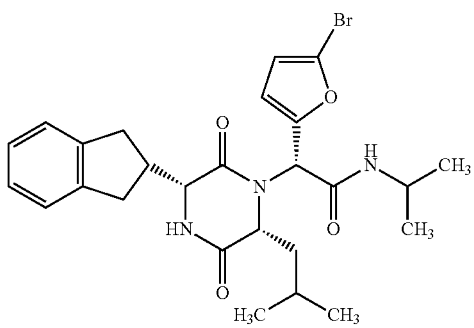 [SMILES: CC(C)C[C@@H]1C(=O)N[C@H](C2Cc3ccccc3C2)C(=O)N1[C@@H](C(=O)NC(C)C)c1ccc(Br)o1] | 530.5 | 3.5 | 529/531 | 527/529 | (2R)-2-(5-bromo-2-furyl)-2-[(3R,6R)-3-(2,3-dihydro-1H-inden-2-yl)-6-isobutyl-2,5-dioxopiperazin-1-yl]-N-isopropylethanamide |
| 203 | 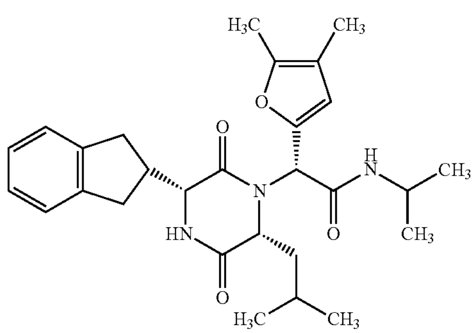 [SMILES: Cc1cc([C@H](C(=O)NC(C)C)N2C(=O)[C@@H](C3Cc4ccccc4C3)NC(=O)[C@H]2CC(C)C)oc1C] | 479.7 | 3.5 | 480 | 478 | (2R)-2-[(3R,6R)-3-(2,3-dihydro-1H-inden-2-yl)-6-isobutyl-2,5-dioxopiperazin-1-yl]-2-(4,5-dimethyl-2-furyl)-N-isopropylethanamide |
| 204 | 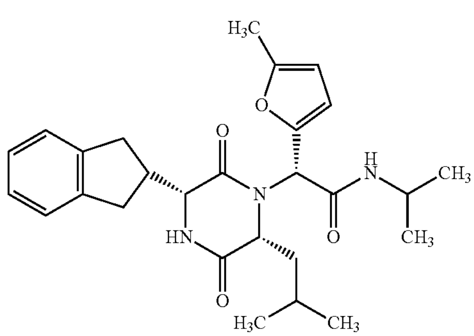 [SMILES: Cc1ccc([C@H](C(=O)NC(C)C)N2C(=O)[C@@H](C3Cc4ccccc4C3)NC(=O)[C@H]2CC(C)C)o1] | 465.7 | 3.4 | 466 | 464 | (2R)-2-[(3R,6R)-3-(2,3-dihydro-1H-inden-2-yl)-6-isobutyl-2,5-dioxopiperazin-1-yl]-N-isopropyl-2-(5-methyl-2-furyl)ethanamide |

-continued

| Eg No. | Structure | MWt | Rt/ min | +ve ion | −ve ion | name |
|---|---|---|---|---|---|---|
| 205 | 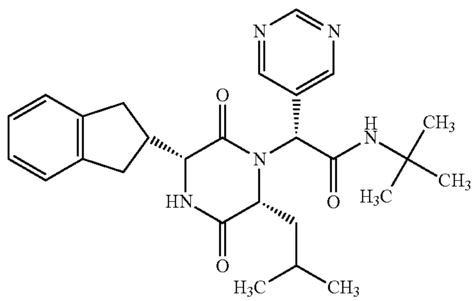 [SMILES: CC(C)C[C@@H]1C(=O)N[C@H](C2Cc3ccccc3C2)C(=O)N1[C@@H](C(=O)NC(C)(C)C)c1cncnc1] | 477.6 | 3.3 | 478 | 476 | (2R)-N-(tert-butyl)-2-[(3R,6R)-3-(2,3-dihydro-1H-inden-2-yl)-6-isobutyl-2,5-dioxopiperazin-1-yl]-2-pyrimidin-5-ylethanamide |
| 206 | 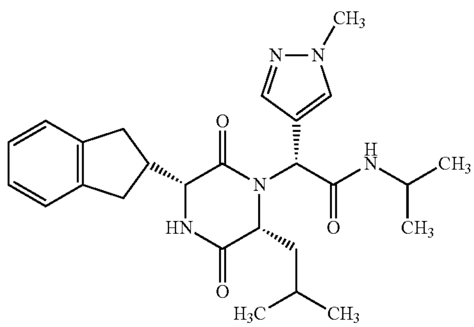 [SMILES: CC(C)C[C@@H]1C(=O)N[C@H](C2Cc3ccccc3C2)C(=O)N1[C@@H](C(=O)NC(C)C)c1cnn(C)c1] | 465.7 | 2.9 | 466 | 464 | (2R)-2-[(3R,6R)-3-(2,3-dihydro-1H-inden-2-yl)-6-isobutyl-2,5-dioxopiperazin-1-yl]-N-isopropyl-2-(1-methyl-1H-pyrazol-4-yl)ethanamide |
| 207 | 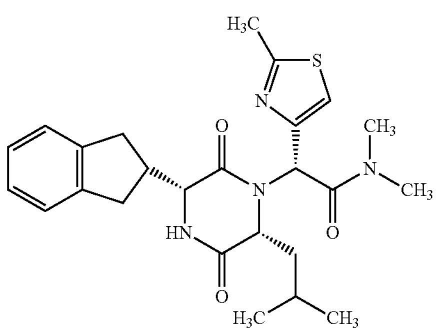 [SMILES: Cc1nc([C@H](C(=O)N(C)C)N2C(=O)[C@@H](C3Cc4ccccc4C3)NC(=O)[C@H]2CC(C)C)cs1] | 468.7 | 3 | 469 | none | (2R)-2-[(3R,6R)-3-(2,3-dihydro-1H-inden-2-yl)-6-isobutyl-2,5-dioxopiperazin-1-yl]-N,N-dimethyl-2-(2-methyl-1,3-thiazol-4-yl)ethanamide |
| 208 | 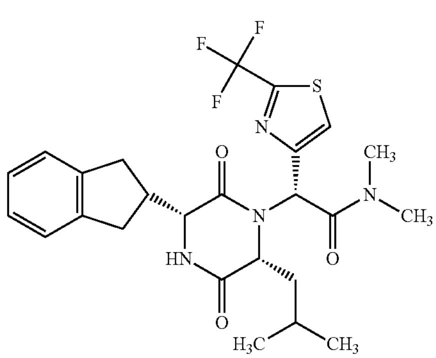 [SMILES: CC(C)C[C@@H]1C(=O)N[C@H](C2Cc3ccccc3C2)C(=O)N1[C@@H](C(=O)N(C)C)c1csc(C(F)(F)F)n1] | 522.6 | 3.4 | 523 | 521 | (2R)-2-[(3R,6R)-3-(2,3-dihydro-1H-inden-2-yl)-6-isobutyl-2,5-dioxopiperazin-1-yl]-N,N-dimethyl-2-[2-(trifluoromethyl)-1,3-thiazol-4-yl]ethanamide |

-continued

| Eg No. | Structure | MWt | Rt/ min | +ve ion | −ve ion | name |
|---|---|---|---|---|---|---|
| 209 | 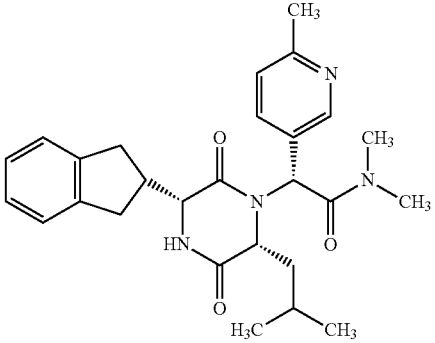 [SMILES: Cc1ccc([C@H](C(=O)N(C)C)N2C(=O)[C@@H](C3Cc4ccccc4C3)NC(=O)[C@H]2CC(C)C)cn1] | 462.7 | 3.1 | 463 | none | (2R)-2-[(3R,6R)-3-(2,3-dihydro-1H-inden-2-yl)-6-isobutyl-2,5-dioxopiperazin-1-yl]-N,N-dimethyl-2-(6-methylpyridin-3-yl)ethanamide |
| 210 | 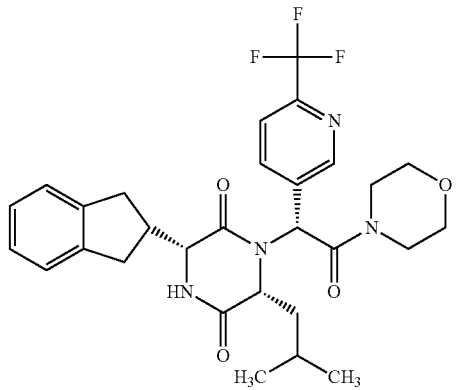 [SMILES: CC(C)C[C@@H]1C(=O)N[C@H](C2Cc3ccccc3C2)C(=O)N1[C@@H](C(=O)N1CCOCC1)c1ccc(C(F)(F)F)nc1] | 558.7 | 3.3 | 559 | 557 | (3R,6R)-3-(2,3-dihydro-1H-inden-2-yl)-6-isobutyl-1-{(1R)-2-morpholin-4-yl-2-oxo-1-[6-(trifluoromethyl)pyridin-3-yl]ethyl}-piperazine-2,5-dione |
| 211 | 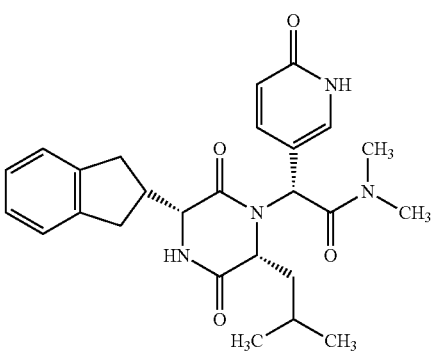 [SMILES: CC(C)C[C@@H]1C(=O)N[C@H](C2Cc3ccccc3C2)C(=O)N1[C@@H](C(=O)N(C)C)c1ccc(=O)[nH]c1] | 464.6 | 2.7 | 465 | 463 | (2R)-2-[(3R,6R)-3-(2,3-dihydro-1H-inden-2-yl)-6-isobutyl-2,5-dioxopiperazin-1-yl]-N,N-dimethyl-2-(6-oxo-1,6-dihydropyridin-3-yl)ethanamide |
| 212 | 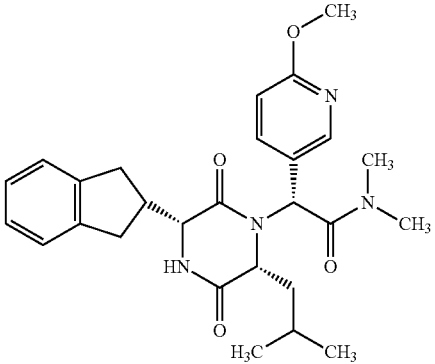 [SMILES: COc1ccc([C@H](C(=O)N(C)C)N2C(=O)[C@@H](C3Cc4ccccc4C3)NC(=O)[C@H]2CC(C)C)cn1] | 478.6 | 3.04 | 479.23 | 477.26 | (2R)-2-[(3R,6R)-3-(2,3-dihydro-1H-inden-2-yl)-6-isobutyl-2,5-dioxopiperazin-1-yl]-2-(6-methoxypyridin-3-yl)-N,N-dimethylethanamide |

-continued

| Eg No. | Structure | MWt | Rt/ min | +ve ion | −ve ion | name |
|---|---|---|---|---|---|---|
| 213 | 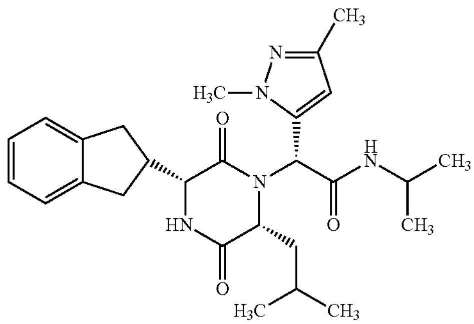 [SMILES: Cc1cc([C@H](C(=O)NC(C)C)N2C(=O)[C@@H](C3Cc4ccccc4C3)NC(=O)[C@H]2CC(C)C)n(C)n1] | 479.6 | 3.03 | 480 | 478 | (2R)-2-[(3R,6R)-3-(2,3-dihydro-1H-inden-2-yl)-6-isobutyl-2,5-dioxopiperazin-1-yl]-2-(1,3-dimethyl-1H-pyrazol-5-yl)-N-isopropylethanamide |
| 214 | 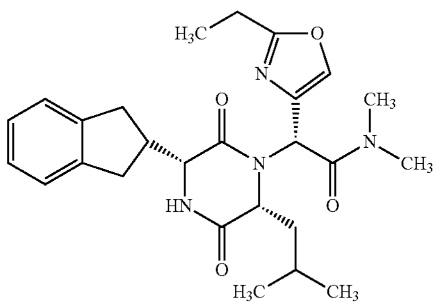 [SMILES: CCc1nc([C@H](C(=O)N(C)C)N2C(=O)[C@@H](C3Cc4ccccc4C3)NC(=O)[C@H]2CC(C)C)co1] | 466.56 | 3.1 | 467 | — | (2R)-2-[(3R,6R)-3-(2,3-dihydro-1H-inden-2-yl)-6-isobutyl-2,5-dioxopiperazin-1-yl]-2-(2-ethyl-1,3-oxazol-4-yl)-N,N-dimethylethanamide |
| 215 | 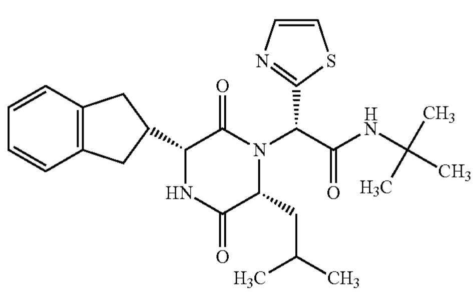 [SMILES: CC(C)C[C@@H]1C(=O)N[C@H](C2Cc3ccccc3C2)C(=O)N1[C@@H](C(=O)NC(C)(C)C)c1nccs1] | 482.6 | 3.58 | 483 | 481 | N-(tert-butyl)-2-[(3R,6R)-3-(2,3-dihydro-1H-inden-2-yl)-6-isobutyl-2,5-dioxopiperazin-1-yl]-2-(1,3-thiazol-2-yl)acetamide |
| 216 | 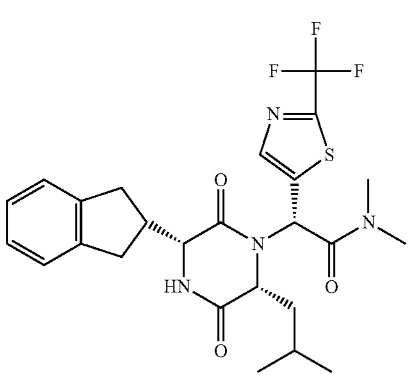 [SMILES: CC(C)C[C@@H]1C(=O)N[C@H](C2Cc3ccccc3C2)C(=O)N1[C@@H](C(=O)N(C)C)c1cnc(C(F)(F)F)s1] | 522.6 | 3.46 | 523 | 521 | 2-[(3R,6R)-3-(2,3-dihydro-1H-inden-2-yl)-6-isobutyl-2,5-dioxopiperazin-1-yl]-N,N-dimethyl-2-[2-(trifluoromethyl)-1,3-thiazol-5-yl]acetamide |

| Eg No. | Structure | MWt | Rt/ min | +ve ion | −ve ion | name |
|---|---|---|---|---|---|---|
| 217 | 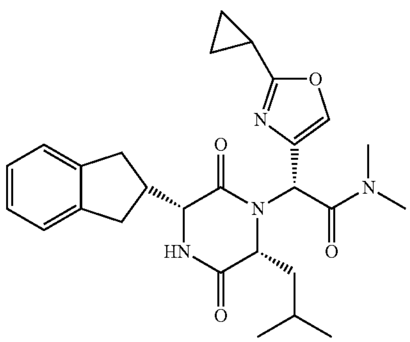 [SMILES: CC(C)C[C@@H]1C(=O)N[C@H](C2Cc3ccccc3C2)C(=O)N1[C@@H](C(=O)N(C)C)c1coc(C2CC2)n1] | 478.6 | 3.07 | 479 | 477 | (2R)-2-(2-cyclopropyl-1,3-oxazol-4-yl)-2-[(3R,6R)-3-(2,3-dihydro-1H-inden-2-yl)-6-isobutyl-2,5-dioxopiperazin-1-yl]-N,N-dimethylethanamide |
| 218 | 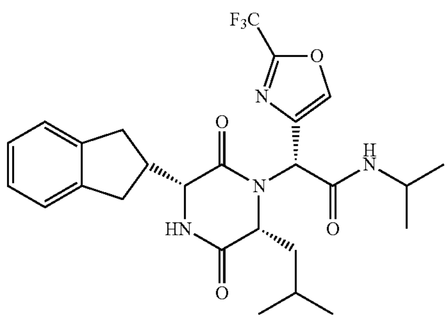 [SMILES: CC(C)C[C@@H]1C(=O)N[C@H](C2Cc3ccccc3C2)C(=O)N1[C@@H](C(=O)NC(C)C)c1coc(C(F)(F)F)n1] | 520.5 | 3.47 | 521 | 519 | (2R)-2-[(3R,6R)-3-(2,3-dihydro-1H-inden-2-yl)-6-isobutyl-2,5-dioxopiperazin-1-yl]-N-isopropyl-2-[2-(trifluoromethyl)-1,3-oxazol-4-yl]ethanamide |
| 219 | 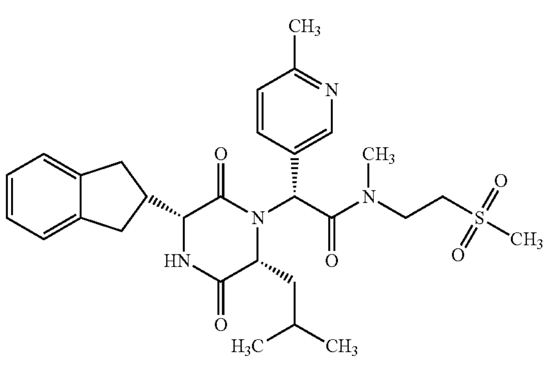 [SMILES: Cc1ccc([C@H](C(=O)N(C)CCS(C)(=O)=O)N2C(=O)[C@@H](C3Cc4ccccc4C3)NC(=O)[C@H]2CC(C)C)cn1] | 554.7 | 2.8 | 555 | 553 | (2R)-2-[(3R,6R)-3-(2,3-dihydro-1H-inden-2-yl)-6-isobutyl-2,5-dioxopiperazin-1-yl]-N-methyl-2-(6-methylpyridin-3-yl)-N-[2-(methylsulfonyl)ethyl]ethanamide |
| 220 | 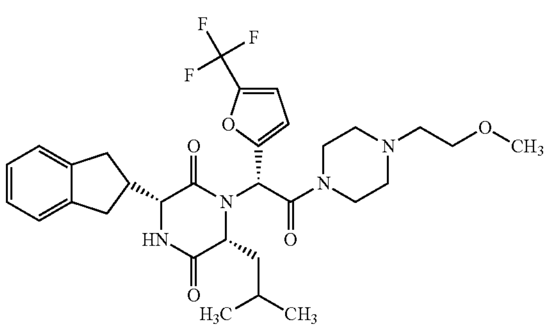 [SMILES: COCCN1CCN(C(=O)[C@@H](c2ccc(C(F)(F)F)o2)N2C(=O)[C@@H](C3Cc4ccccc4C3)NC(=O)[C@H]2CC(C)C)CC1] | 604.7 | 2.7 | 605 | 603 | (3R,6R)-3-(2,3-dihydro-1H-inden-2-yl)-6-isobutyl-1-{(1R)-2-[4-(2-methoxyethyl)piperazin-1-yl]-2-oxo-1-[5-(trifluoromethyl)-2-furyl]ethyl}piperazine-2,5-dione |

-continued

| Eg No. | Structure | MWt | Rt/ min | +ve ion | -ve ion | name |
|---|---|---|---|---|---|---|
| 221 | 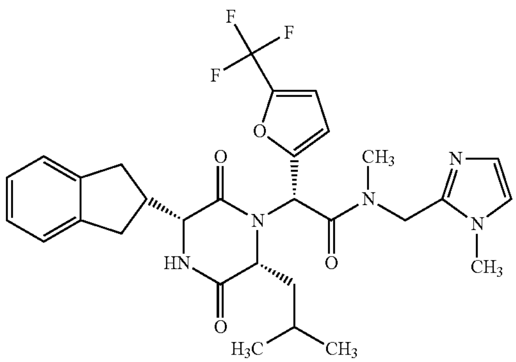 [SMILES: CC(C)C[C@@H]1C(=O)N[C@H](C2Cc3ccccc3C2)C(=O)N1[C@@H](C(=O)N(C)Cc1nccn1C)c1ccc(C(F)(F)F)o1] | 585.6 | 2.8 | 586 | 584 | (2R)-2-[(3R,6R)-3-(2,3-dihydro-1H-inden-2-yl)-6-isobutyl-2,5-dioxopiperazin-1-yl]-N-methyl-N-[(1-methyl-1H-imidazol-2-yl)methyl]-2-[5-(trifluoromethyl)-2-furyl]ethanamide |
| 222 | 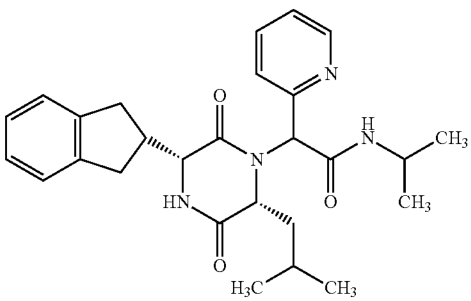 [SMILES: CC(C)C[C@@H]1C(=O)N[C@H](C2Cc3ccccc3C2)C(=O)N1C(C(=O)NC(C)C)c1ccccn1] | 462.6 | 3.29 | 463 | 461 | 2-((3R,6R)-3-Indan-2-yl-6-isobutyl-2,5-dioxo-piperazin-1-yl)-N-isopropyl-2-pyridin-2-yl-acetamide |
| 223 | 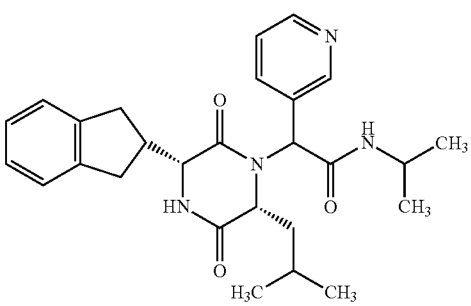 [SMILES: CC(C)C[C@@H]1C(=O)N[C@H](C2Cc3ccccc3C2)C(=O)N1C(C(=O)NC(C)C)c1cccnc1] | 462.6 | 3.09 | 463 | 461 | 2-((3R,6R)-3-Indan-2-yl-6-isobutyl-2,5-dioxo-piperazin-1-yl)-N-isopropyl-2-pyridin-3-yl-acetamide |
| 224 | 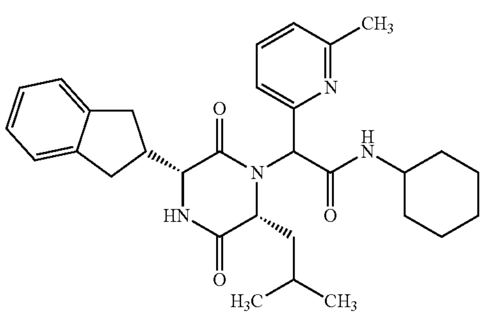 [SMILES: Cc1cccc(C(C(=O)NC2CCCCC2)N2C(=O)[C@@H](C3Cc4ccccc4C3)NC(=O)[C@H]2CC(C)C)n1] | 516.7 | 3.41 | 517 | 515 | N-Cyclohexyl-2-((3R,6R)-3-indan-2-yl-6-isobutyl-2,5-dioxo-piperazin-1-yl)-2-(6-methyl-pyridin-2-yl)-acetamide |

| Eg No. | Structure | MWt | Rt/min | +ve ion | −ve ion | name |
|---|---|---|---|---|---|---|
| 225 | 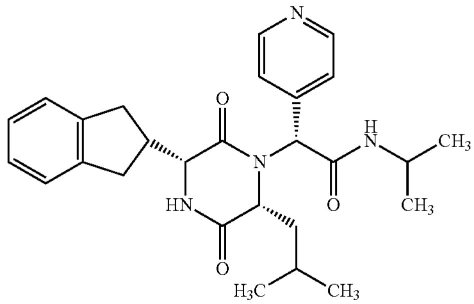 [SMILES: CC(C)C[C@@H]1C(=O)N[C@H](C2Cc3ccccc3C2)C(=O)N1[C@@H](C(=O)NC(C)C)c1ccncc1] | 462.6 | 2.93 | 463 | 461 | 2-((3R,6R)-3-Indan-2-yl-6-isobutyl-2,5-dioxo-piperazin-1-yl)-N-isopropyl-2-pyridin-4-yl-acetamide |
| 226 | 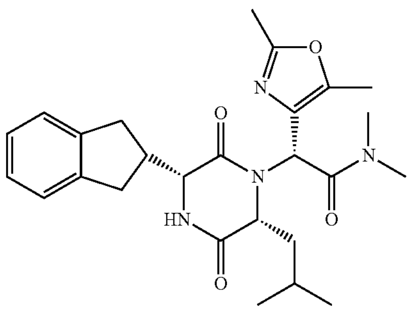 [SMILES: Cc1nc([C@H](C(=O)N(C)C)N2C(=O)[C@@H](C3Cc4ccccc4C3)NC(=O)[C@H]2CC(C)C)c(C)o1] | 466.6 | 3.06 | 467 | — | (R)-2-(2,5-Dimethyl-oxazol-4-yl)-2-((3R,6R)-3-indan-2-yl-6-isobutyl-2,5-dioxo-piperazin-1-yl)-N,N-dimethylacetamide |

EXAMPLE 227

(3R,6R)-1-[(1R)-1-(2,4-Difluorophenyl)-2-(3-fluoro-azetidin-1-yl)-2-oxoethyl]-3-(2,3-dihydro-1H-inden-2-yl)-6-isobutylpiperazine-2,5-dione The azetidinol (Example 15) (57 mg) in anhydrous dichloromethane (2 mL) was stirred at −5° C. and diethylaminosulfur trifluoride (50 µL, excess) was added in one portion. The mixture was left at room temperature overnight and saturated aqueous sodium hydrogen carbonate (3 mL) was added. The mixture was diluted with dichloromethane (10 mL) and the organic phase was separated using a hydrophobic frit and blown down with nitrogen. The crude reaction mixture was purified using the mass-directed autoprep system to give (3R,6R)-1-[(1R)-1-(2,4-difluorophenyl)-2-(3-fluoroazetidin-1-yl)-2-oxoethyl]-3-(2,3-dihydro-1H-inden-2-yl)-6-isobutylpiperazine-2,5-dione (26 mg) as a white solid.

HPLC Rt=3.34 minutes, m/z [M+H]$^+$=514

PHARMACY EXAMPLES

Tablets

| a) | Compound of the invention | 50.0 mg |
|---|---|---|
| | Lactose | 70.0 mg |
| | Microcrystalline Cellulose | 70.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | Compound of the invention | 50.0 mg |
|---|---|---|
| | Lactose | 120.0 mg |
| | Pregelatinised Starch | 20.0 mg |
| | Cross-linked polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

Capsules

| a) | Compound of the invention | 50.0 mg |
|---|---|---|
| | Lactose | 148.0 mg |
| | Magnesium Stearate | 2.0 mg |
| | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) | Compound of the invention | 50.0 mg |
| --- | --- | --- |
| | Lactose | 132.0 mg |
| | Polyvinylpyrrolidone | 8.0 mg |
| | Cross-linked polyvinylpyrrolidone | 8.0 mg |
| | Magnesium Stearate | 2.0 mg |
| | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

Injection Formulation

| | % w/v |
| --- | --- |
| Compound of the invention | 0.10 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 1 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.05, 0.20 and 0.5% w/v of the compound of the invention, so as to provide respectively 0.5, 2 and 5 mg/ml of the compound of the invention.

Measurement of Oxytocin Antagonist Activity

Assay Buffer used throughout the assay: 50 mM HEPES, 10 mM $MgCl_2$, 0.125 mg/ml BSA, pH adjusted to 7.4 with KOH.

hOT-CHO membranes were prepared at a concentration of 0.3 mg protein/ml in assay buffer. Test compounds were initially dissolved in DMSO (to 10 mM) and diluted in DMSO (Beckman Biomek FX). 1 µl of compound was transferred to black 384 assay plates (NUNC) using a Biomek FX. 20 µl of 1 nM Bodipy TMR Oxytocin (Perkin Elmer) in assay buffer was added to all wells (Labsystems Multidrop) then 20 µl membrane added to all wells (Multidrop). Plates were incubated at room temp for 60 min.

Polarisation was read on LJL Analyst (λEx=535 nm, λEm=580 nM, λDichroic=555 nm). Data were fitted to a 4 parameter logistic equation. An estimated Ki was calculated as IC50/5.

In the above test compounds of the invention in general have a pKi value within the range of 7 to 11. Thus the compounds of examples 1 to 227 have a pKi within the range 8.5 to 10.8.

The compounds of the invention are essentially non toxic at therapeutically active doses. Thus compound of the example 10 has been administered to rats at doses of up to 300 mg/kg p.o for 4 days. and no adverse toxicological effects were observed.

The invention claimed is:

1. A process for the preparation of compounds of formula (I):

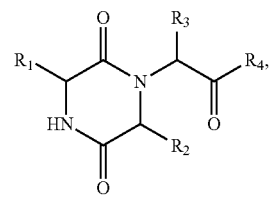

wherein $R_1$ is a 2-indanyl group;

$R_2$ represents $C_{3-6}$cycloalkyl, $C_{1-6}$alkyl optionally substituted by a $C_{1-2}$alkoxy, a $C_{1-2}$alkylthio, a di-$C_{1-2}$alkylamino or a $C_{3-6}$ cycloalkyl group, or a 5 or 6 membered heterocyclic group containing a single hetero atom selected from O, S or N, which nitrogen atom carries a hydrogen atom or a methyl or ethyl group;

$R_3$ represents an optionally substituted phenyl,
a 5 membered heteroaryl group which is unsubstituted or substituted by one or more groups selected from halogen, trifluoromethyl, $C_{1-4}$alkyl, cycloalkyl, heteroaryl, saturated heterocyclic, or phenyl,
a 6 membered heteroaryl group which is unsubstituted or substituted by 1 to 3 $C_{1-4}$alkyl, or trifluoromethyl, or alkoxy groups, or
a fused bicyclic ring system containing 9-10 ring members which ring system contains a benzene and which ring members include 0 to 3 heteroatoms selected from O, S or N;

$R_4$ represents $NR_5R_6$,
where,
$R_5$ represents hydrogen, $C_{1-6}$alkyl optionally substituted with $C_{1-4}$alkoxy, or $C_{3-7}$cycloalkyl,
$R_6$ represents hydrogen, methyl, $C_{1-4}$alkoxy, $C_{3-7}$cycloalkyl, $C_{2-4}$alkyl optionally substituted with one or more $R_{50}$, or $C_{2-4}$alkyl optionally substituted with one or more $R_{55}$,
or $R_6$ represents a phenyl or benzyl group optionally substituted by one or more methoxy or benzyloxy groups, an optionally substituted heteroarylmethyl group, a heteroaryl group, $C_{3-7}$ cycloalkyl, or the group $CH_2CONR_9R_{10}$,
or $R_5$ and $R_6$ together with the nitrogen to which they are attached form a 3 to 7 membered saturated heterocycle optionally substituted with one or more $R_{60}$ which heterocycle optionally contains an additional heteroatom selected from oxygen, sulphur and nitrogen, wherein the sulphur atom may be in an oxidised form and the additional nitrogen atom either carries a hydrogen atom or a $C_{1-4}$alkyl or a $C_{1-4}$alkanoyl group or a $C_{1-4}$alkylsulphonyl group or a $C_{1-3}$ alkoxy$C_{2-4}$ alkyl, where,
- $R_{50}$ is selected from the group consisting of: carboxyl, $C_{1-4}$alkylsulphonyl, or $C_{1-4}$alkoxycarbonyl, and
- $R_{55}$ is selected from the group consisting of: halogen, hydroxy, $C_{1-4}$alkoxy, or $NR_7R_8$, where,
- $R_7$ and $R_8$ independently represent hydrogen or $C_{1-4}$alkyl or together form a 3 to 7 membered saturated heterocyclic ring which optionally contains an additional heteroatom selected from O, S or N and which heterocyclic group may be substituted by 1 to 3 groups selected from $C_{1-3}$alkyl, hydroxy, $C_{1-3}$ alkoxy optionally substituted by $C_{3-6}$ cycloalkyl or optionally substituted phenyl, $C_{3-6}$cycloalkyl or $NR_cR_d$, wherein $R_c$ and $R_d$ each independently represent a group selected from $C_{1-3}$alkyl optionally substituted by $C_{3-6}$ cycloalkyl or optionally substituted phenyl, or $C_{3-6}$ cycloalkyl,
- $R_9$ represents hydrogen or $C_{1-4}$alkyl, and
- $R_{10}$ represents hydrogen, $C_{1-4}$alkyl optionally substituted by a 5 or 6 membered heteroaryl group, or $R_9$ and $R_{10}$ together form a 5 or 6 membered saturated heterocyclic ring and wherein the 6 membered heterocyclic group optionally contains an additional heteroatom selected from oxygen, sulphur or nitrogen and the additional nitrogen atom either carries a hydrogen atom or a $C_{1-4}$alkyl or $C_{1-4}$alkanoyl group, and
- $R_{60}$ is selected from the group consisting of: halogen, $C_{1-3}$alkyl, hydroxy, oxo, $C_{3-6}$cycloalkyl or $NR_eR_f$ wherein $R_e$ and $R_f$ each independently represent a group selected from $C_{1-3}$alkyl optionally substituted by $C_{3-6}$ cycloalkyl or optionally substituted phenyl or $C_{3-6}$ cycloalkyl, wherein the method comprises:

(a) cyclisation of the compound of formula (II)

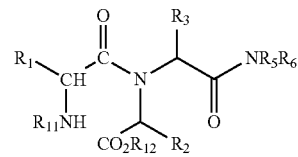

(II)

wherein $R_{11}$ is hydrogen and $R_{12}$ is a $C_{1-3}$alkyl group in a suitable solvent or (b) reacting a compound of formula (I) wherein $R_4$ is hydroxyl or an activated derivative thereof with the amine $NHR_5R_6$ wherein $R_5$ and $R_6$ have the meaning defined in formula (I);

(c) reacting a compound of formula (I) wherein $R_4$ is the group $NR_5R_6$ and $R_5$ is hydrogen and $R_6$ is 2-hydroxyphenyl with carbonyldiimidazole or thiocarbonyldiimidazole in a suitable solvent and subsequent reaction of the product thus formed with amine $NHR_5R_6$.

* * * * *